US012589099B2

(12) United States Patent
Kay

(10) Patent No.: US 12,589,099 B2
(45) Date of Patent: Mar. 31, 2026

(54) ALPHA-1062 FOR TREATING TRAUMATIC BRAIN INJURY

(71) Applicant: ALPHA COGNITION INC., Vancouver (CA)

(72) Inventor: Denis G. Kay, Charlottetown (CA)

(73) Assignee: Alpha Cognition Inc., Vancouver (CA)

( * ) Notice: Subject to any disclaimer, the term of this patent is extended or adjusted under 35 U.S.C. 154(b) by 155 days.

(21) Appl. No.: 18/549,309

(22) PCT Filed: Nov. 25, 2022

(86) PCT No.: PCT/CA2022/051730
§ 371 (c)(1),
(2) Date: Sep. 6, 2023

(87) PCT Pub. No.: WO2023/092231
PCT Pub. Date: Jun. 1, 2023

(65) Prior Publication Data

US 2024/0299407 A1 Sep. 12, 2024

(30) Foreign Application Priority Data

Nov. 26, 2021 (EP) .................................... 21210661
Feb. 21, 2022 (EP) .................................... 22157789
Jun. 10, 2022 (EP) .................................... 22178357

(51) Int. Cl.
*A61K 31/55* (2006.01)
*A61K 9/00* (2006.01)
*A61P 25/00* (2006.01)

(52) U.S. Cl.
CPC ............ *A61K 31/55* (2013.01); *A61K 9/0043* (2013.01); *A61P 25/00* (2018.01)

(58) Field of Classification Search
CPC ........ A61P 25/00; A61K 31/55; A61K 9/0043
See application file for complete search history.

(56) References Cited

U.S. PATENT DOCUMENTS 11,077,119 B2 8/2021 Maelicke

FOREIGN PATENT DOCUMENTS

WO WO 2014/016430 A1 1/2014

OTHER PUBLICATIONS

Bakker, C., et al., Safety, pharmacokinetics, and pharmacodynamics of Gln-1062, a prodrug of galantamine, Alzheimer's & Dementia, 6;e12093, DOI: 10,1002/trc2.12093; (Oct. 12, 2020) (Year: 2020).*
European Search Report in European Application No. 21210661.1 mailed on May 13, 2022, in 10 pages.
International Search Report in International Application No. PCT/CA2022/051730, mailed on Jan. 31, 2023, in 4 pages.
Bakker et al., "Safety, pharmacokinetics, and pharmacodynamics of Gln-1062, a prodrug of galantamine", Alzheimer's Dementia, 2020, 6: e12093 (in 10 pages).
Zhao et al., "Post-Injury Administration of Galantamine Reduces Traumatic Brain Injury Pathology and Improves Outcome", J. Neurotrauma, 35:362-274; Jan. 15, 2018.
Bengtsson et al., "Effects of Acetylcholinesterase Inhibitors on Cognitive Function in Patients with Chronic Traumatic Brain Injury: A Systematic Review", J. Rehabilitation Medicine, 48:1-5, 2016.
Tenovuo et al., "Central acetylcholinesterase inhibitors in the treatment of chronic traumatic brain injury—clinical experience in 111 patients", Progress in Neuro-Psychopharmacology & Biological Psychiatry, 29: 61-67, 2005.
Maelicke et al., "Memogain is a Galantamine Pro-drug having Dramatically Reduced Adverse Effects and Enhanced Efficacy". Journal of Molecular Neuroscience, vol. 40, No. 1- 2, Jan. 1, 2010, pp. 135-137.
Bakkman et al., "First in human study with a prodrug of galatamine: Improved benefit-risk ration?", Alzheimer's & Dementia: Translational Research & Clinical Interventions, vol. 2, No. 1, Jan. 1, 2016, pp. 13-22.
Kaletta et al., "Memogain, a novel high potency drug treatment for AD", Abstracts of the Annual Meeting of the Society for Neuroscience, Society for Neuroscience, US, vol. 40, Jan. 1, 2010.
Extended European Search Report for App. No. 22896916.8, dated Oct. 17, 2025 (in 66 pages).

* cited by examiner

*Primary Examiner* — Erich A Leeser
(74) *Attorney, Agent, or Firm* — Knobbe, Martens, Olson & Bear, LLP

(57) ABSTRACT

A pharmaceutical composition including a compound ALPHA-1062 or salt thereof, or a compound ALPHA-1062 or salt thereof, for use in the treatment of confirmed or suspected traumatic brain injury (TBI) in a subject. In embodiments, the composition is administered transmucosally, such as intranasally, and/or the composition is self-preserving and anti-microbial. Also disclosed is a multi-use dispenser configured for intranasal or transmucosal administration of a pharmaceutical composition including ALPHA-1062 or salt thereof. Also disclosed is a method of treating traumatic brain injury (TBI) in a subject including administering a therapeutically effective amount of a pharmaceutical composition including ALPHA-1062 or salt thereof.

27 Claims, 16 Drawing Sheets

Figure 1:
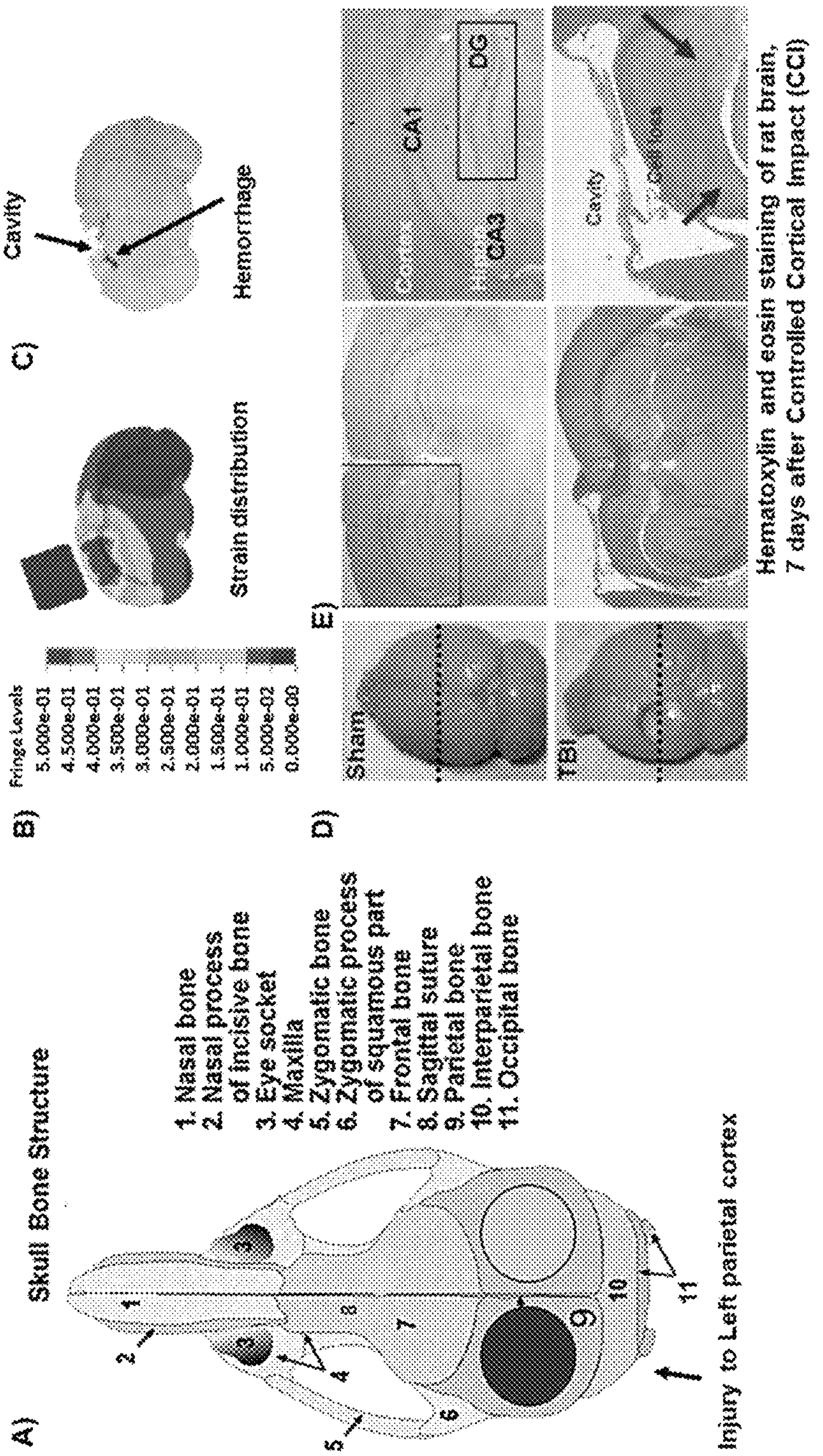

Scale bars = 25 μm.

ALPHA-1062 FOR TREATING TRAUMATIC BRAIN INJURY

The present invention is in the field of compositions, formulations and dispensing devices for pharmaceutical agents, in addition to medical methods.

The invention relates to a pharmaceutical composition comprising a compound ALPHA-1062 or salt thereof, or to a compound ALPHA-1062 or salt thereof, for use in the treatment of confirmed or suspected traumatic brain injury (TBI) in a subject. In embodiments, the composition is administered transmucosally, such as intranasally, and/or the composition is self-preserving and anti-microbial. The invention also relates to a multi-use dispenser configured for intranasal or transmucosal administration of a pharmaceutical composition comprising ALPHA-1062 or salt thereof. The invention further relates to a method of treating traumatic brain injury (TBI) in a subject comprising administering a therapeutically effective amount of a pharmaceutical composition comprising ALPHA-1062 or salt thereof.

BACKGROUND OF THE INVENTION

Traumatic brain injury (TBI) is a global public health problem and a leading cause of death and disability. TBI is clinically classified as mild, moderate, or severe at the time of injury, typically using a Glasgow Coma Scale (GCS). Severe TBI can result in mortality rates as high as 30-40%. Survivors experience a substantial burden of physical, psychiatric, emotional and cognitive disabilities which disrupt the lives of individuals and their families. Such disabilities are not restricted to severe cases, but also occur frequently after moderate or mild TBI.

The effects and outcome of TBI are not only influenced by the severity of injury but also by factors such as repetitive incidents and age. TBI is attributed to a variety of injury mechanisms, including falls, automobile or other types of traffic injuries, sports injuries, and interpersonal physical or other violence (e.g., explosion injury). In terms of age, TBI shows a bimodal distribution with the highest incidence in the youngest and oldest age groups. These age groups are likely to be more prone to TBI due to the increased risk of various causes of injury, such as falls in children under 4 years of age and in older people over 75 years of age, and motor vehicle accidents in adults.

Sport-related TBI is increasingly being described as a chronic health condition, as evidence suggests that the health effects of TBI can linger over time, especially in those who suffer from moderate to severe TBI. The majority of patients suffering a mild TBI (mTBI) recover quickly, but effects of mTBI can last for a year or more. Symptoms that are often associated with chronic effects include cognitive deficits, such as attention deficits, memory problems, and executive dysfunction or even social deficits. Long term effects of mTBI can range from impaired social inference—the interpretation of verbal and nonverbal social cues—to psychological symptoms such as anxiety, or physical symptoms such as fatigue, balance and coordination problems. mTBI can be associated with persistent headaches, vestibular dysfunction, depression, and cognitive complaints. The cumulative effects can lead to symptoms such as cognitive, behavioral, mood, and motor disorders.

Repeated injuries have been studied most thoroughly in contact sports such as American football, where the athletes have an increased risk of death from suicide, decreased cognitive functions, macrostructural, microstructural, functional and neurochemical changes and an increased risk of death from neurodegenerative causes such as dementia or Alzheimer's disease. Another cause for TBI can be blast-related TBI in military personnel (Haarbauer-Krupa et al., J Neurotrauma, 2021; Brazinova et al., J Neurotrauma, 2021; Center-TBI project; American Association of Neurological Surgions (AANS)).

As of today, no curative treatment for TBI itself is available. Current medications aim to reduce secondary brain damage occurring as downstream effects or symptoms of TBI. Such drugs comprise anti-seizure drugs for patients experiencing seizures after moderate or severe TBI, coma-inducing drugs, which aim to reduce the oxygen consumption of the damaged brain and diuretics that can reduce the pressure inside the brain. Other available treatment options for TBI are only surgical interventions, physical and mental rest or rehabilitation treatment targeting chronical effects of TBI.

Galantamine and derivatives thereof have been suggested for the treatment of neurodegenerative diseases, such as Alzheimer's and dementia. Unfortunately, similar to other cholinesterase inhibitors, galantamine has a clinically significant level of mechanism-based gastro-intestinal (GI) side effects, including nausea, vomiting and diarrhea (Loy C et al., Galantamine for Alzheimer's disease and mild cognitive impairment. Cochrane Database of Systematic Reviews 2006). To accommodate patients to these side effects, cholinesterase inhibitors usually are initially administered at a low (non-efficacious) dose, with the dose being carefully up-titrated to an efficacious one, within a period of four to six weeks. Moreover, the maintenance dose often is adjusted to what the patients experience as an acceptable level of GI side effects, making it likely that most, if not all, patients never achieve treatment with the most effective dose. Cholinesterase inhibitors such as galantamine are therefore considered suboptimal in addressing TBI, where immediate efficacious doses would be preferred.

To enhance the lipophilicity of acetylcholinesterase inhibitors and improve their passage through mucosal tissue, hydrophobic side chains have been appended to the basic alkaloid structures. Galantamine derivatives and pro-drugs are described in EP1940817, WO2009/127218 and US2009/0253654.

The galantamine pro-drug ALPHA-1062, is a benzoic acid or benzoate ester of galantamine ((4aS,6R,8aS)-5,6,9,10,11,12-hexahydro-3-methoxy-11-methyl-4aH-[1]benzofuro[3a,3,2-ef][2]benzazepin-6-ol benzoate). It was developed to enhance the hydrophobicity of galantamine. ALPHA-1062 exhibits essentially no pharmacological activity until it is cleaved by esterases, resulting in the release of galantamine.

WO 2014/016430 discloses transmucosal administration of ALPHA-1062 via intranasal, buccal or sublingual modes, in addition to various formulations and salts of ALPHA-1062, including for example lactate, gluconate, maleate and saccharate salts.

The first nasal spray pumps for intranasal administration of liquid compositions were developed approximately 50 years ago and replaced the previous step by step droppers and pipettes. Nasal spray pumps are now widely used to moisturize the nasal mucosa using saline solutions, as nasal preparations for the administration of topically acting drugs, e.g. nasal decongestants, or for the non-invasive administration of substances which need to reach systemic circulation, e.g. anti-migraine medication or hormones (Marx and Birkhoff, "Multi-Dose Container for Nasal and Ophthalmic Drugs: A Preservative Free Future?" in Drug Development-A Case Study Based Insight into Modern Strategies, ed. Chris Rundfeldt, 2011).

For many disease indications, multi-dose devices are cost effective and convenient means to provide the safety and precision in administration of active agents that regulatory bodies require. However, until now, most medications administered transmucosally, commonly as solutions, emulsions or suspensions, contain a preservative to support long storage times and proper in-use stability for multi-use or multi-dose dispensers. However, despite the advantages of nasal administration, the use of preservatives in nasal sprays is controversial. Reports suggest that preservatives in nasal sprays might increase the risk of adverse events for patients.

Tenovuo et al (Progress in Neuro-Psychopharmacology & Biological Psychiatry, vol. 29, no. 1, p. 61-67, 2005) teach oral administration of donepezil, galantamine or rivastigmine as a treatment of chronic stable TBI. The study was not placebo controlled, and no clinical examination was carried out after drug administration to verify the reported improvement of symptoms. Patients with chronic TBI reported a subjective improvement of TBI-related symptoms after treatment, although about half of all patients experienced disturbing adverse effects. Despite the study being conducted almost two decades ago, none of these drugs has been adopted as a standard of care in the management of either acute or chronic TBI.

Medicaments are therefore lacking for first-line treatment of TBI, especially in an acute setting, that could reduce or prevent secondary downstream injuries and short and/or long-term symptoms of TBI, such as cognitive and neurological impairments. The provision of effective treatments for TBI is urgently needed.

SUMMARY OF THE INVENTION

In light of the prior art the technical problem underlying the invention was the provision of improved or alternative means for treating traumatic brain injury (TBI). Another problem underlying the invention was the provision of a convenient, multi-use and preferably preservative-free formulation suitable for administering an efficacious amount of an active pharmaceutical agent in treating TBI.

This problem is solved by the features of the independent claims. Preferred embodiments of the present invention are provided by the dependent claims.

The invention therefore relates to a pharmaceutical composition comprising a compound ALPHA-1062 or salt thereof for use in the treatment of confirmed or suspected traumatic brain injury (TBI) in a subject.

In other embodiments or aspects, the invention relates to a compound ALPHA-1062 or salt thereof, for use in the treatment of confirmed or suspected traumatic brain injury (TBI) in a subject In other embodiments or aspects, the invention relates to a method of treating traumatic brain injury (TBI) in a subject comprising administering a pharmaceutically effective amount of a pharmaceutical composition comprising ALPHA-1062 or salt thereof The present invention is based on the finding that ALPHA-1062 shows efficacy in treating TBI. As discussed in more detail below, an exemplary 35-day study using a controlled cortical impact injury model was conducted, indicating the effectiveness of ALPHA-1062. The positive therapeutic effects on TBI may include, without limitation, improved functional and histological outcomes after traumatic brain injury (TBI).

One difference between the previously published work and the current ALPHA-1062 study was the extent of acute protection achieved via ALPHA-1062 administration, which appears to reduce the extent of functional deficit at 1 day post TBI, and the persistently improved speed and extent of recovery, all relative to vehicle treatment. Compared to the published literature, ALPHA-1062 treatment had a more potent effect than galantamine in terms of both functional recovery and decreased neuropathology. A skilled person would not have expected that ALPHA-1062 would enable these advantages over administration of galantamine.

The inventors surprisingly observed that ALPHA-1062 administration preserved brain structure, reduced neuronal cell loss and promoted neurogenesis following TBI. The inventors found that ALPHA-1062 treatment (in comparison to vehicle control treatment) after TBI preserved brain structure, such as hippocampal structure, and significantly enhanced neurogenesis including augmentation of neuroblasts (validated by tissue staining for the neurogenesis marker DCX or BrdU/NeuN+). ALPHA-1062 treatment also significantly reduced the lesion size measured at 35 days after TBI injury, and significantly reduced the neuronal cell loss in brain areas affected by the TBI, for example in the cortex and hippocampus regions of injured brains. Unexpectedly, the degree of neuroprotection was so potent, that neuron cell counts determined in these regions of animals subjected to a TBI and treated with ALPHA-1062 were indistinguishable from those determined for the sham treated [uninjured] animals.

Additionally, ALPHA-1062 treatment significantly reduced the accumulation of a form of pathologically phosphorylated Tau (AT-8 positive), which is known to accumulate in the brains of TBI and Alzheimer's patients. Without being bound by theory, the reduced p-Tau accumulation observed after ALPHA-1062 treatment of TBI in the rat study disclosed in detail below, may reduce the risk of TBI patients treated with ALPHA-1062 of later developing dementia. In some cases, even a single mild TBI-without loss of consciousness—can significantly increase the risk of dementia by about two-fold, as shown in cohort of American service personnel evaluated longitudinally (Barnes et al, Association of mild traumatic brain injury with and without loss of consciousness with dementia in US military veterans. JAMA neurology, 2018, 75(9), 1055-1061). In Alzheimer's disease, pathological-Tau accumulation precedes that of beta amyloid by several years. Pathologically phosphorylated Tau is thought to spread much like a prion protein, by 'seeding', with a relatively slow development, having a predicted doubling time of approximately 5 years. Considering that TBI can induce (or is associated with) an increased long-term risk of dementia, it appears plausible that ALPHA-1062 treatment, shown to reduce pathologically phosphorylated Tau, may also show benefits in reducing the risk of later-developing neurological defects. The observation of reduced p-Tau accumulation in the TBI model disclosed below is entirely novel, this technical effect has not been shown or suggested for galantamine previously.

In summary, the inventors found ALPHA-1062 treatment effective against moderate TBI and significantly improved recovery of brain tissue, sensory motor and cognitive functional skills when administered acutely following injury. To the knowledge of the inventors, the improvements observed could not have been predicted from the prior art with respect to the TBI experimental group.

In one embodiment the composition is in liquid form.

In embodiments, the liquid is a solution, emulsion or a suspension.

In another embodiment the composition is in solid form.

In embodiments, the solid form is a tablet, pill, film, lozenge or capsule.

The invention also relates to a pharmaceutical composition comprising a compound ALPHA-1062 or salt thereof for use in the treatment of confirmed or suspected traumatic brain injury (TBI) in a subject, wherein the composition is administered transmucosally.

In embodiments, the composition is administered intranasally.

In embodiments, the composition is administered to the oral cavity.

In embodiments, the composition is administered sublingually or buccally.

Advantageous transport properties can be achieved for pro-drugs when administered by intravenous injection, but less well, or only to a small extent, when they are administered orally, as e.g. tablets, for systemic administration. This is often because pro-drug esters are instable in acidic environments (such as exists in the stomach) and may be cleaved enzymatically in many tissues, including in the intestines and in the liver (first-pass effect).

In light of these findings and the problems of the administration methods of the prior art, and in order to take advantage of ALPHA-1062 in the treatment of CNS diseases, in some embodiments the invention makes use of administration routes that avoid the gastro-intestinal tract and the first-pass effect (loss of a certain percentage of a drug due to the metabolism in the gut and liver).

These routes of administration for ALPHA-1062 provide brain delivery of the active drug galantamine at similar levels as intravenous injection of ALPHA-1062. The invention therefore employs in some embodiments pharmaceutical formulations to be used for the selected routes of administration that optimize rapid absorption and uptake of ALPHA-1062.

Of note, is that transmucosal administration of galantamine, as in the prior art, provides no such enhancement, as galantamine is not susceptible to cleavage by endogenous esterases. A surprising concept of transmucosal administration of ALPHA-1062 in treating TBI is based on the avoidance of cleavage of the prodrug post-administration but before partition via the BBB, thereby enhancing brain transport and increased relative concentration of the active substance after cleavage, which under conditions of the proposed routes of administration and drug formulations, occurs significantly in the brain.

Hence, the invention provides improved means and formulations that can be administrated immediately after the occurrence of brain trauma, in an effective and easy-to-use form that shows low side effects and enables good patient compliance.

As shown in the Examples, the inventors developed application and treatment methods that surprisingly reduce the short- and long-term effects of TBI, such as impaired cognitive, neurological and motor functions. The formulations and compounds according to the invention show surprisingly beneficial effects in the treatment of subjects, which have suffered TBI or potentially other brain traumata. The treatment of subjects that have suffered a TBI event with formulations and compounds according to the present invention comprising ALPHA-1062 or salts thereof results in a better recovery of motor skills, and spatial and recognition memory, in comparison to vehicle treatment. The treatment of subjects suffering from TBI with ALPHA-1062 or salts thereof according to the present invention appears to cause superior restoration of motor and memory skills and other cognitive functions, which are comparable to skills in healthy individuals that did not suffer from TBI. This surprising effect is complemented by transmucosal administration of the compounds and compositions according to the invention, which facilitates not only improved patient compliance due to its easy administration and its reduced adverse effects, but also achieves a good efficacy of the compound due to the direct delivery of the compound to the brain (avoidance of first pass effect). This surprising effect may represent a significant improvement in the current treatment options for TBI and is evidenced by the experimental results shown in the Examples.

Accordingly, the present invention provides new and surprising solutions for treating, reducing and/or preventing (or reducing the risk of) TBI-related short and long-term symptoms, such as acute and/or chronic neurological and cognitive impairment.

The invention therefore relates in one embodiment to ALPHA-1062 for use as a medicament in the treatment of TBI as described herein, wherein transmucosal administration is configured to avoid and/or reduce immediate post-administration cleavage of the ester group of said substance by endogenous esterases, e.g. during and/or after absorption from the gastrointestinal tract.

This aspect of the present invention, namely addressing the relatively low stability of the ester moiety of ALPHA-1062 in the gastro-intestinal tract and liver, represents a novel technical effect in the treatment for TBI not previously disclosed or suggested in the art.

The avoidance of in vivo esterase cleavage—with regard to the improvements obtained by transmucosal administration and the enhanced delivery of the compounds and salts described herein—enables treatment of patients who would previously have avoided or discontinued treatment with AChE inhibitors due to strong gastro-intestinal side effects associated with oral administration of galantamine at an efficacious dose, without the typical 4 to 6 week up-titration period required for tolerability. The improved brain delivery via transmucosal administration, in particular of high concentration aqueous solutions of ALPHA-1062 salts administered nasally, permits dosage regimes which were previously challenging or impractical, with respect to galantamine (due to significant side effects) or ALPHA-1062 (due to in vivo degradation via the oral route).

The invention also relates to a pharmaceutical composition comprising a compound ALPHA-1062 or salt thereof for use in the treatment of confirmed or suspected traumatic brain injury (TBI) in a subject, wherein the composition is self-preserving and anti-microbial, wherein preferably the composition is essentially absent of additional antimicrobial preservatives.

As described in detail below, the invention is based on the surprising finding of beneficial effects of the use of ALPHA-1062 in the treatment of TBI. No indication is evident in the prior art prior that this agent (ALPHA-1062) has anti-microbial properties. As is described in the introduction, ALPHA-1062 was known to exhibit an effect against cognitive impairment by acting as a pro-drug of galantamine. No suggestion is evident in the art that galantamine or its prodrug ALPHA-1062 could exhibit the property of actively reducing CFU/mL of pathogenic bacteria, yeast and fungi, as demonstrated according to the USP 51 test.

The identification of this novel property (anti-microbial effect) of a known substance (ALPHA-1062) opens new clinical perspectives and creates a new clinical situation when considering either formulating or administering the substance. New patient populations have been enabled due 7
8 to the discovery of the novel properties, and new dosage regimes and formulation options may now be employed, based on the surprising property.

The provision of a self-preserving ALPHA-1062 composition, preferably as a liquid, or more preferably as an emulsion or solution, such as in the form of multi-use dispensers without additional preservatives, enables reduced side effects, for example side effects caused by nasal administration of a solution that comprises an additional preservative. Storage properties of any given formulation may now be improved, i.e. longer storage times may be evident due to the discovery of the anti-microbial properties.

In some embodiments, reduced side effects may be achieved. Such reduced side effects (i.e. as caused by preservatives) may relate to nasal irritation, such as but without limitation to, increased mucosal swelling and nasal hyper-reactivity, type IV hypersensitivity, decrease of muco-ciliary clearance, and nasal mucosa dysplasia.

In some embodiments, the composition of the invention does not comprise one or more, preferably does not comprise any, additional preservative(s), selected from the list consisting of benzalkonium (preferably benzalkonium chloride), benzyl alcohol, thimerosal (merthiolate), edetate disodium, monobasic sodium phosphate, providone, dibasic sodium phosphate, disodium eta, potassium phosphate monobasic, iodine, phenylcarbinol and sodium silicoaluminate.

Furthermore, the provision of a self-preserving ALPHA-1062 solution, such as in the form of multi-use dispensers without additional preservatives, enables good patient compliance compared to single-use or single-dose administration, as described in the art. The provision of a simple spray dispenser, capable of multiple uses, but without preservatives, is a simple and low side effect-option for patients. Firstly, low mucosal or nasal irritation should lead to enhanced patient compliance, as discomfort, e.g., in the nose and/or mouth, is reduced. Secondly, using an easy-to-use dispenser and keeping this single dispenser over time, for multiple uses, makes administration simpler for cognitive and/or neurologically impaired and/or elderly subjects, or if the treatment is administered to infants or children.

In contrast, the daily administration of tablets intended for swallowing or single-dose dispensers is associated with additional complication, requiring a patient, who is potentially a child or cognitively and/or neurologically impaired, to either swallow tablets or to continually open, apply and purchase single dose dispensers, leading to complications and delivery burden. Consequently, the herein described administration forms of the compositions and compounds according to the present invention reduce adverse effects and improve the patient compliance in the treatment of TBI, resulting in further improved treatment outcomes of TBI, as regular and/or long-term administration of the compounds according to the invention is ensured or at least supported.

The multi-use dispenser of the invention may therefore be maintained in first-aid kits, or the first response equipment of emergency medical personnel. The anti-microbial features of ALPHA-1062, in combination with its efficacious effect in treating TBI and/or symptoms thereof, enables a multi-use dispenser that does not require frequent replenishment or replacement, making it an ideal active agent in e.g. pre-prepared first aid medical kits.

In one embodiment, the pharmaceutical composition comprising a compound ALPHA-1062 or salt thereof for use in the treatment of confirmed or suspected traumatic brain injury (TBI) in a subject comprises a sufficient amount of ALPHA-1062 to have an anti-microbial effect. Such an antimicrobial effect may in some embodiments refer to an antimicrobial effect in the pharmaceutical formulation, such as in maintaining a relatively microbial free or low-microbe environment within the formulation, or to in vivo effects, post-administration, leading to a reduction of microbial load in the area of administration.

In one embodiment, the pharmaceutical composition comprising ALPHA-1062 or salt thereof for use in the treatment of confirmed or suspected traumatic brain injury (TBI) in a subject is characterized in that the compound ALPHA-1062 or salt thereof is present at a concentration of 1 to 200 mg/mL, preferably between 5 and 100 mg/mL.

In some embodiments, the ALPHA-1062 or salt thereof are present in the composition at a concentration of 1 to 500 mg/mL, preferably between 1 and 400 mg/mL, more preferably between 1 and 300 mg/mL, preferably between 1 and 200 mg/mL, preferably between 5 and 100 mg/mL.

In some embodiments, the ALPHA-1062 or salt thereof are present at about 5 mg/mL, or 10, 15, 20, 25, 30, 35, 40, 45, 50, 55, 60, 65, 70, 75, 80, 85, 90, 95, 100, 110, 120, 130, 140, or at about 150 mg/mL. Ranges constructed form any given of the afore-mentioned values are also contemplated.

In some embodiments, the ALPHA-1062 is present in the composition as a salt, preferably a lactate, gluconate, maleate or saccharate salt. Generation of ALPHA-1062 salts are described in the art, e.g. in WO 2014/016430, and can be carried out without undue burden.

In some embodiments, the salt comprises stoichiometric and/or non-stoichiometric salts and/or hydrates of the chemical substances according to ALPHA-1062, whereby the salt is preferably described as:

$$\text{ALPHA-1062} \cdot n \text{ HX} \cdot m \text{ H}_2\text{O},$$

wherein n and m=0-5, and n and m can be the same or different, and HX is an acid, selected preferably from lactic acid, gluconic acid, maleic acid or saccharic acid.

In some embodiments, other acids may be employed for the ALPHA-1062 salt formation.

Acids useful for preparing the pharmaceutically acceptable acid addition salts according to the invention include inorganic acids and organic acids, such as sulfamic, amidosulfonic, 1,2-ethanedisulfonic, 2-ethylsuccinic, 2-hydroxyethanesulfonic, 3-hydroxynaphthoic, acetic, benzoic, benzenesulfonic acid, carboxylic, ethylenediamine tetraacetic acid, camphorsulfonic, citric, dodecylsulfonic, ethanesulfonic, ethenesulfonic, ethylenediamine tetraacetic, fumaric, glubionic, glucoheptonic, gluconic, glutamic, hexylresorcinic, hydrobromic, hydrochloric, isethionoc, (bi)carbonic, tartaric, hydriodic, lactic, lactobionic, laevulinic, laurylsulfuric, lipoic, malic, maleic, malonic, mandelic, methanesulfonic, mucic, naphthalenesulfonic, nitric, oxalic, pamoic, pantothenic, perchloric, phosphoric, polygalacturonic, pectic, propionic, salicylic, succinic or sulfuric acid, p-tuluenesulfonic, wherein hydrochloric, hydrobromic, sulfuric, nitric, phosphoric and perchloric acids, as well as tartaric, citric, acetic, succinic, maleic, fumaric and oxalic acids.

It was surprising, that embodiments of the pharmaceutically applicable solutions of ALPHA-1062 salts fulfilled the criteria for appropriate stability, concentration, pH, osmolarity and nasal mucosal tolerance in solution, for intranasal application in the treatment of TBI.

In one embodiment of the invention the pharmaceutical composition comprises a crystalline solid form of ALPHA-1062 gluconate. In one embodiment, the crystalline solid form of ALPHA-1062 gluconate is Form A, as disclosed in WO 2022/150917.

Figure 6:
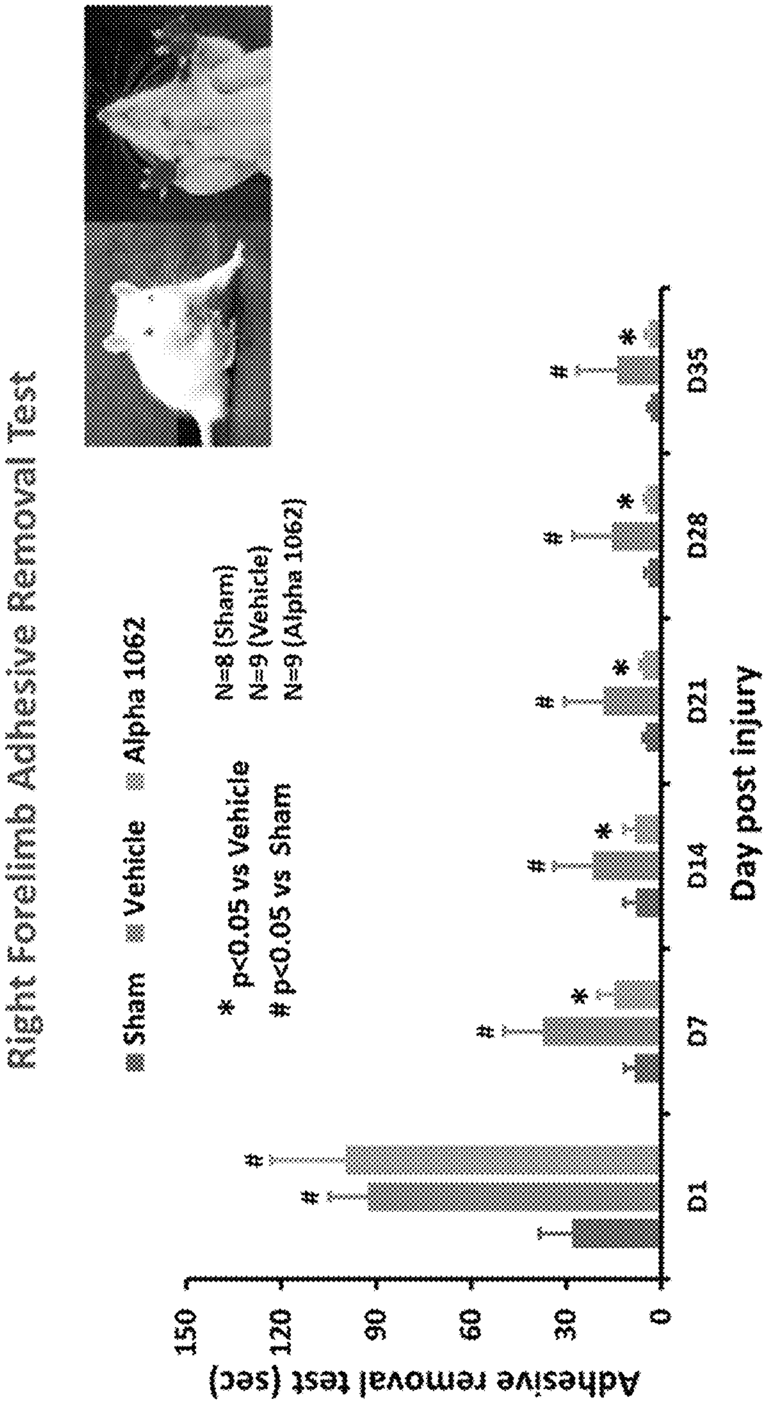

As described therein, polymorphic studies were conducted with ALPHA-1062 utilizing a variety of solvents and crystallization conditions (Table 5 of WO 2022/150917) and subsequent XRPD analyses. Seven unique crystalline materials were observed and isolated, and were designated as Forms A, B, C, D and Materials E, F and G (FIG. 6 of WO 2022/150917). Amorphous material was also observed. Form A of ALPHA-1062 is an anhydrous crystalline material with concomitant melt/decomposition onset near 117° C. Form A appears kinetically stable in the solid state at 43% RH (RT) and was sustained up to 5 days at that condition. Based upon WO 2022/150917, anhydrous Form A, stored under appropriate temperature and humidity conditions to maintain its Form and stability, appears best suited of the various ALPHA-1062 forms to be used in formulation and manufacture of drug products.

In one embodiment, the invention relates to a crystalline solid form of ALPHA-1062 gluconate (Form A), wherein said crystalline form has prominent peaks at 3.61, 10.98, 14.41 and 18.44 degrees 2-theta (±0.2) in a powder X-ray diffraction pattern.

In one embodiment, Form A has one or more additional prominent peaks at 15.20, 17.31, 17.79, 22.77, 23.64, 24.88 and 34.31 degrees 2-theta (±0.2) in a powder X-ray diffraction pattern. These peaks are selected from the prominent peak list presented in WO 2022/150917 and appear to exhibit no substantial overlap with prominent peaks in the XRPD patterns for Forms B-D, or Materials E-G. In one embodiment, Form A has at least five prominent peaks selected from the list consisting of 3.61, 10.98, 13.80, 14.41, 14.56, 15.08, 15.20, 17.02, 17.31, 17.79, 18.44, 19.24, 20.18, 20.91, 21.22 and 22.40 degrees 2-theta (±0.2) in a powder X-ray diffraction pattern.

The use of Form A of ALPHA-1062 represents a preferred embodiment of the invention, as polymorphic stability of Form A can be maintained after formulation during storage. Form A can also enable high drug solubility and effective therapeutic effect. Form A may therefore be used in the preparation of a solution to be administered to a subject or directly in a solid administration form.

In one embodiment, the ALPHA-1062 salt has solubility in water of at least 10%, preferably >20%, or more preferably >30% weight per volume (w/v). The high solubility enables higher concentrations of the compound to be administered in smaller volumes, thereby further enhancing administration via e.g. transmucosal administration.

The preferred embodiment of transmucosal administration represents a beneficial mode of delivery due to a combination of factors. The enhanced solubility of ALPHA-1062 salts allows higher concentrations of ALPHA-1062 to be administered, thereby enabling larger amounts of the active substance after cleavage (galantamine) to be active in the brain. In embodiments the prodrug properties of ALPHA-1062 are exploited and enhanced by the transmucosal application of the ALPHA-1062 salts.

The invention therefore also relates to a method for treating a confirmed or suspected brain injury associated with cognitive and/or neurological impairment in a subject, the method comprising administering a therapeutically effective amount of ALPHA-1062 or salt thereof to a subject in need thereof.

In one embodiment, the pharmaceutical composition of the invention has the compound ALPHA-1062 present as a gluconate salt, preferably at a concentration of 50-100 mg/mL, more preferably 70-90 mg/mL, or alternatively at a concentration disclosed herein. A skilled person is aware of varying the concentration of the active agent according to common practice.

In one embodiment, the pharmaceutical composition of the invention is characterized in that the compound ALPHA-1062 is present at a concentration sufficient to reduce $1\times10^4$ to $1\times10^6$ colony-forming units per mL (CFU/mL) of *Escherichia coli, Pseudomonas aeruginosa, Staphylococcus aureus, Candida albicans* and/or *Aspergillus brasiliensis* to <100 CFU/mL, preferably <10 CFU/mL, within 14 days treatment, according to the United States Pharmacopeia Chapter 51 preservative test (USP 51). ALPHA-1062 shows anti-microbial activity against both gram-positive and gram-negative bacteria, pathogenic yeasts and fungi, thereby indicating a broad-spectrum anti-microbial effect. As there is no suggestion in the prior art that ALPHA-1062 could exhibit such a broad and effective anti-microbial activity and that treatment of TBI could benefit from it, the exploitation of this property of ALPHA-1062 in the treatment of TBI represents therefore a surprising and unexpected finding with practical utility.

In some embodiments, the liquid composition is stable, i.e. exhibits sufficient drug or pro-drug stability and low microbial loads, over extended periods. In some embodiments, the extended period is for about 1 week, or 1, 2, 3, 4, 5, 6, 7, 8 weeks, or longer. In some embodiments, the composition is stable for about 1 month, or 2, 3, 4, 5, 6, 7, 8, 9, 10, 11, or 12 months. During this time, the composition may be administered via multi-use device of the invention, or in storage. In some cases, storage of the composition is possible (preferably without use by a subject) for about 1, 2, 3, 4 or 5 years.

In embodiments the composition is present in a multi-use dispenser configured for transmucosal administration.

In embodiments the composition is present in a single-use dispenser configured for transmucosal administration.

In embodiments the composition is present in a suitable metered dose device such as an atomizer, sprayer, pump spray, dropper, squeeze tube, squeeze bottle, pipette, ampule, nasal cannula, metered dose device, nasal spray inhaler, nasal continuous positive air pressure device, and/or breath actuated bi-directional delivery device.

In one embodiment, a therapeutically effective amount of the compound is administered using a suitable metered multi-use dose device or dispenser, such as a multi-use atomizer, multi-use sprayer, multi-use pump spray, multi-use dropper, multi-use squeeze tube or bottle multi-use metered dose device or multi-use nasal sprayer or inhaler.

In one embodiment, a therapeutically effective amount of the compound is administered using a suitable single-use dose device or dispenser. In embodiments the single-use dose device or dispenser is selected from the group comprising a single use dropper, a single-use squeeze tube or bottle, and a single dose powder dispenser.

In one embodiment, a therapeutically effective amount of the ALPHA-1062 or salt thereof is administered to the oral cavity.

In one embodiment, a therapeutically effective amount of the compound ALPHA-1062 or salt thereof is administered under the tongue (sub-lingual) by dispensing an amount of compound, preferably in the form of a solution or emulsion, from a multi-use dispenser, and/or by spraying the underside of the tongue with a preselected volume of a liquid composition, preferably a solution or emulsion, from a multi-use dispenser comprising the compound or salt thereof.

In one embodiment, a therapeutically effective amount of the compound or salt thereof is administered to the buccal vestibule inside the mouth between the cheek and the gums, preferably as a solution or emulsion, from a multi-use dispenser.

In a further aspect of the invention, in the non-limiting context of a multi-use dispenser, the invention combines the properties, features and advantages of multi-use transmucosal delivery devices with the anti-microbial property of ALPHA-1062 or salts thereof. Accordingly, the multi-use dispenser according to the invention configured for transmucosal administration of a pharmaceutical composition in the form of a liquid, comprises a self-preserving anti-microbial solution as described herein with ALPHA-1062 or salt thereof.

In one embodiment the administration to the oral cavity is carried out by placing one or more drops of a solution or emulsion to the oral cavity, by spraying a preselected volume of a liquid composition to the oral cavity, or by administering a sub-lingual tablet, film formulation, lozenge, orally disintegrating or orally dispersing tablet to the oral cavity.

In one embodiment, a therapeutically effective amount of the compound is administered to the buccal vestibule inside the mouth between the cheek and the gums, preferably as a solution or emulsion, from a multi-use dispenser.

In one embodiment, the multi-use dispenser is configured for intranasal administration.

In one embodiment, the multi-use dispenser is configured for administration to the oral cavity.

In one embodiment, the multi-use dispenser is configured for transmucosal administration.

In one embodiment, the multi-use dispenser as described herein is for use in the treatment of confirmed or suspected traumatic brain injury (TBI) in a subject (or for use in a corresponding method of treatment), wherein the treatment comprises administering multiple doses of the pharmaceutical composition, which is preferably self-preserving anti-microbial, as described herein, to the subject from the same dispenser.

Hence, in another aspect, the invention relates to a multi-use dispenser configured for intranasal administration of a pharmaceutical composition comprising ALPHA-1062 or salt thereof in the form of a liquid, for use in the treatment of confirmed or suspected traumatic brain injury (TBI) in a subject.

Hence, in another aspect, the invention also relates to a multi-use dispenser configured for administration to the oral cavity of a pharmaceutical composition comprising ALPHA-1062 or salt thereof in the form of a liquid, for use in the treatment of confirmed or suspected traumatic brain injury (TBI) in a subject.

In a further aspect, the invention relates to a single-use dispenser configured for intranasal administration of a pharmaceutical composition comprising ALPHA-1062 or salt thereof in the form of a liquid, for use in the treatment of confirmed or suspected traumatic brain injury (TBI) in a subject.

In another aspect, the invention also relates to a single-use dispenser configured for administration to the oral cavity of a pharmaceutical composition comprising ALPHA-1062 or salt thereof in the form of a liquid, for use in the treatment of confirmed or suspected traumatic brain injury (TBI) in a subject.

The following embodiments relate to both, the administration of a composition comprising a compound ALPHA-1062 or salt thereof as disclosed herein, as well as to the herein disclosed pharmaceutical composition, to the single- and the multi-use dispenser.

In one embodiment of the multi-use dispenser configured for intranasal administration of a pharmaceutical composition comprising ALPHA-1062 or salt thereof in the form of a liquid, for use in the treatment of confirmed or suspected traumatic brain injury (TBI) in a subject, the multi-use dispenser is a suitable metered multi-use dose device or dispenser, such as an inhaler, atomizer, sprayer, pump spray, dropper, squeeze tube, squeeze bottle, pipette, ampule, nasal cannula, metered dose device, nasal spray inhaler, nasal continuous positive air pressure device, breath actuated bi-directional delivery device a multi-use atomizer, multi-use sprayer, multi-use pump spray, multi-use dropper, multi-use squeeze tube or bottle, multi-use metered dose device and/or multi-use nasal sprayer.

In one embodiment of the multi-use dispenser configured for intranasal or transmucosal administration of a pharmaceutical composition comprising ALPHA-1062 or salt thereof in the form of a liquid, for use in the treatment of confirmed or suspected traumatic brain injury (TBI) in a subject, the multi-use dispenser dispenses in one dosing event volumes of between 10 μl to 200 μl.

In one embodiment of the multi-use dispenser the dispenser further comprises different actuators, and/or neck finishes known in the art, such as screw-on, snap-on and crimp-on.

Preferred dispensers of the invention relate to any of the above-mentioned multi-use devices. In some embodiments, the dispensers available for example from Nemera (La Verpillière, France) or Aptar Pharma (Illinois, USA) are preferred.

Nasal sprays can be contaminated through their drug delivery orifices, with bacterial contamination coming from the external environment or the patient, or from the air. Therefore, in some embodiments, to prevent contamination via air entering the device, nasal sprays may be employed in which a filter system is present that stops the entry of bacteria into the container.

Airborne bacteria are typically around 0.3 μm, therefore appropriately sized filters may be selected. Furthermore, recent studies have demonstrated that bacterial transfer through filter membranes takes place during filtration operations, even if the pore size is significantly smaller than the bacteria size. Therefore, in some embodiments, devices are employed that utilize a silicone membrane to filter the returning air.

In some embodiments, the multi-use dispenser employs a membrane (preferably of silicone) that prevents bacteria from entering the reservoir or pump device. In one embodiment of the multi-use dispenser according to the invention the multi-use dispenser comprises a spring-loaded tip seal mechanism, a filter membrane in the ventilation channel, a venting system with a silicone membrane, a permeable membrane and/or a silicone membrane to reduce the contamination of the composition comprised within the dispenser. In some embodiments, the multi-use dispenser employs a spring-loaded tip seal mechanism, thereby preventing microbes from entering the device between spray events. In some embodiments, the multi-use dispenser employs a metal-free fluid path, thereby preventing the oxidization of the formulation.

Instead of using preservatives, advanced spray dispenser technology represents an alternative way of keeping a nasal spray sterile, by preventing bacteria entering and contaminating the drug formulation. Such dispensers may also be employed in the present invention, thereby further reducing microbial burden in the multi-use dispenser. In combination, the anti-microbial properties of ALPHA-1062 or salts thereof with the "preservative-free" dispenser technology, as described herein, and as is known to a skilled person from e.g. Nemera or Aptar, lead to unexpectedly good shelf life (either in storage or during usage) of a liquid composition comprising ALPHA-1062 or salts thereof.

In one embodiment, the dispenser is configured for multiple individual spray events of 5 to 1000 μL, preferably 5 to 500 μL, more preferably 10 to 300 μL, more preferably 20 to 200 μL.

In one embodiment, the dispenser is configured for multiple individual spray events of about 5 μL, or 10, 15, 20, 25, 30, 35, 40, 45, 50, 55, 60, 65, 70, 75, 80, 85, 90, 95, 100, 120, 140, 160, 180, 200, 250, 300, 350, 400, 450 or 500 UL volume. Ranges constructed from any given of the afore-mentioned values are also contemplated.

In one embodiment, the dispenser comprises a total volume of composition of 1 to 500 mL, preferably 1 to 100 mL, more preferably 2 to 50 mL, such as for example about 5, 10 or 15 mL.

In one embodiment, the dispenser comprises about 1 mL, 2, 3, 4, 5, 6, 7, 8, 9, 10, 11, 12, 13, 14, 15, 16, 18, 20, 30, 40, 50, 60, 70, 80, 90, 100, 110, 120, 130, 140, 150, 160, 170, 180, 190, 200, 220, 240, 260, 280, 300, 350, 400, 450, or 500 mL volume. Ranges constructed from any given of the afore-mentioned values are also contemplated.

In some embodiments, the dispenser must comprise a sufficient amount of composition for administration of multiple doses. In some embodiments, the dispenser comprises a sufficient volume of composition for at least 2, or at least, or about 3, 4, 5, 6, 7, 8, 9, 10, 12, 14, 16, 18, 20, 25, 30, 35, 40, 45, 50, 60, 70, 80, 90 or about 100 individual doses, or more doses. Ranges constructed form any given of the afore-mentioned values are also contemplated.

In one embodiment, the dispenser is configured for multiple individual spray events of 20 to 200 μL, and wherein said dispenser comprises a total volume of solution of 2 to 50 mL.

In one embodiment, the multi-use dispenser is configured for and/or the ALPHA-1062 or salt thereof is administered at a dose of 1 to 100 mg, one to three times daily, preferably for multiple days.

In one embodiment, the multi-use dispenser is configured for and/or the ALPHA-1062 or salt thereof is administered at a dose of 2 to 40 mg, twice daily, preferably over multiple days.

In one embodiment, the multi-use dispenser is configured for and/or the ALPHA-1062 or salt thereof is administered at a dosage of from 0.1 to 200 mg, 1 to 100 mg, preferably 2 to 40 mg, preferably from one to three times daily, more preferably twice daily, and even more preferably only once daily, over multiple days.

In one embodiment, the ALPHA-1062 or salt thereof is administered intranasally as a 2 to 40% weight per volume (w/v) solution at an amount of 20 to 100 microliters in each of multiple nasal spray events, one to three times daily, over multiple days.

In one embodiment, the multi-use dispenser is configured for and/or the ALPHA-1062 or salt thereof is administered, preferably intranasally, as an about 10% weight per volume (w/v) solution at an amount of about 50 microliters in each of multiple administration events, one to three times daily, preferably over multiple days.

In one embodiment, the multi-use dispenser is configured for and/or the ALPHA-1062 or salt thereof is administered by intranasal, buccal or sublingual administration, preferably as a 2 to 40% weight per volume (w/v) solution, for example at an amount of 20 to 100 microliters, preferably multiple (intranasal or oral (sub-lingual/buccal)) administration events, for example from one to three times daily, preferably over multiple days.

In some embodiments, the liquid formulations are configured for any one or more of the above administration modes. A skilled person is aware of technical means employed in configuring compositions for specific modes of administration. For example, a composition configured for nasal administration may be formulated, packaged, or prepared in a different manner from compositions prepared for oral administration.

In embodiments of the invention the TBI is classified as mild TBI, moderate TBI, or severe TBI.

In the context of the use of ALPHA-1062 or salts thereof in the treatment of confirmed or suspected TBI, the composition or compound can be administered to subjects immediately after an acute TBI event as well as to subjects who suffered a suspected or confirmed TBI event in the past. Hence, the use of ALPHA-1062 or salts thereof refers in embodiments to the treatment and/or the prevention of acute and/or chronic symptoms and/or outcomes of TBI.

In embodiments, the invention therefore relates to a pharmaceutical composition comprising a compound ALPHA-1062 or salt thereof for use in the treatment of confirmed or suspected traumatic brain injury (TBI) in a subject, wherein the subject that has or is suspected to suffer from TBI shows one or more symptoms selected from the group consisting of dizziness, balance problems, headaches, nausea, vomiting, light sensitivity, impaired memory, sleep abnormalities, impaired concentration and impaired vision.

In embodiments, the invention also relates to a pharmaceutical composition comprising a compound ALPHA-1062 or salt thereof for use in the treatment of confirmed or suspected traumatic brain injury (TBI) in a subject, wherein the subject that has or is suspected to suffer from moderate or severe TBI shows one or more symptoms selected from the group consisting of weakness in arms and legs, balance and coordination problems, severe or increasing headaches, impaired sensory perception, impaired cognitive skills, impaired memory, impaired communication and learning, personality changes, behavior abnormalities and impaired vision and hearing.

In embodiments, the invention also relates to a pharmaceutical composition comprising a compound ALPHA-1062 or salt thereof for use in the treatment of confirmed or suspected traumatic brain injury (TBI) in a subject, wherein the subject that has or is suspected to suffer from severe TBI shows one or more symptoms selected from the group consisting of paralysis, coma, loss of consciousness, dilated pupils, loss of cerebrospinal fluid from the ears or nose, loss of bowel and/or bladder control, breathing problems, slow pulse, breathing problems, slow breathing rate with an increase in blood pressure and droopy eyelid or facial weakness.

In embodiments, the invention also relates to a pharmaceutical composition comprising a compound ALPHA-1062 or salt thereof for use in the treatment of confirmed or suspected traumatic brain injury (TBI) in a subject, wherein the traumatic brain injury (TBI) leads to or is accompanied by one or more injuries selected from the group consisting of a hematoma, contusion, intracerebral hemorrhage, subarachnoid hemorrhage, diffuse injuries, diffuse axonal injury, ischemia, primary brain injury and secondary brain injury.

The formulations and compounds according to the invention show the surprising beneficial effects in the treatment of TBI or potentially other brain traumata of reducing the severity and/or preventing (reducing the risk of) the occurrence of short and long-term symptoms of TBI. As shown in the Examples herein, the transmucosal administration of compositions comprising ALPHA-1062 or salts thereof, according to the present invention, to subjects suffering from TBI or other brain traumata results in an improved recovery of motor skills, memory and other cognitive functions, when compared to vehicle treatment after TBI.

In embodiments, the traumatic brain injury (TBI) is caused by a closed head injury.

In embodiments, the traumatic brain injury (TBI) is caused by a penetrating head injury.

In embodiments, the traumatic brain injury (TBI) is caused by a head injury resulting from an incident selected from the group consisting of a fall, a motor vehicle-related incident, a strike or blow to the head from or against an object, a sports-related incident, interpersonal physical violence or violence by other means. In embodiments, the traumatic brain injury (TBI) is caused by a contact sport, or an incident and/or accident occurring in contact sport, such as American football, rugby, soccer, martial arts, Australian rules football, hockey, basketball, and so forth. TBI may also, in embodiments, be caused by sports accidents induced by being struck by a ball, for example in baseball or cricket, or other sports.

In embodiments, the traumatic brain injury (TBI) is a blast related TBI, or military TBI, as may occur for example in civilian or military personnel due to an explosion in the vicinity of the subject. Head injuries caused by bullets, violent impact, or shock waves from explosive weapons are the main causes of military traumatic brain injury (TBI), which is a recognized medical neurological condition affecting large numbers of military personnel world-wide. As a result of armed conflict, head trauma from exposure to blasts is an increasing critical health issue, particularly among military service members. Frequently associated comorbidities are post-traumatic stress disorder, depression, anxiety, sleep disorders, attention disorders, and cognitive disorders.

In embodiments, the subject that has or is suspected to suffer from TBI is an infant under the age of 4 years.

In embodiments, the subject is under 12 months of age.

In embodiments, the subject that has or is suspected to suffer from TBI is a child from 4 to 12 years of age, In embodiments, the subject is an adolescent from 12 to 17 years of age.

In embodiments, the subject that has or is suspected to suffer from TBI is an adult, selected from an adult of between 18 and 65 years of age.

In embodiments, the subject is an (elderly) adult of over 65 years of age.

In embodiments, the invention relates to a pharmaceutical composition comprising a compound ALPHA-1062 or salt thereof for use in the treatment of confirmed or suspected traumatic brain injury (TBI) in a subject, wherein the traumatic brain injury (TBI) is associated with trauma to the nasal cavity.

In embodiments, the invention relates to treatment of traumatic brain injury (TBI) and concurrent treatment and/or prevention of microbial infection of the nasal cavity.

In embodiments, the invention also relates to a pharmaceutical composition comprising a compound ALPHA-1062 or salt thereof for use in the treatment of confirmed or suspected traumatic brain injury (TBI) in a subject, wherein the traumatic brain injury (TBI) is associated with disruption of the blood brain barrier.

In embodiments, the invention relates to treatment of traumatic brain injury (TBI) and concurrent treatment and/or prevention of microbial infection of the central nervous system.

The combination of therapeutic properties of ALPHA-1062 including both neurological brain function improving properties and antimicrobial properties relates to an unexpected combination of benefits that make the invention ideally suited for TBI treatment, in particular in situations where first-responders or emergency medical personnel must treat quickly post-injury, but also to ongoing use during recovery. In particular, any brain trauma combined with injury to the nasal or oral cavity may be effectively treated using this combination of properties.

The invention therefore also relates to a method as described herein of treating confirmed or suspected traumatic brain injury (TBI) in a subject, wherein said subject suffers additionally from a microbial infection, wherein said method comprises administering ALPHA-1062 or salt thereof to a subject in need thereof.

ALPHA-1062 exhibits a strong anti-microbial effect against various pathogenic microbes. As such, the compound appears ideally suited for the treatment of TBI in a subject, wherein said subject suffers additionally from a microbial infection. In some embodiments, the microbial infection is associated with the TBI. In some embodiments, the infection is unrelated to the TBI. In some embodiments, the infection is a microbial infection, wherein the microbial infection is preferably a pathogenic microbial infection in a subject.

According to the preferred modes of administration, described herein, the compound will come into contact with various mucosal surfaces, which may be subject to an unwanted infection i.e. by a pathogen. The anti-microbial activity of the compound therefore provides a beneficial effect upon administration to a subject.

In embodiments, the invention also relates to a method for reducing incidence of or treating a traumatic brain injury (TBI) in an individual, comprising administering to the individual an effective amount of a compound of ALPHA-1062 or a salt thereof.

In embodiments, the invention also relates to a method for reducing incidence of symptoms selected from the group consisting of dizziness, balance problems, headaches, nausea, vomiting, light sensitivity, impaired memory, sleep abnormalities, impaired concentration and impaired vision as a consequence of traumatic brain injury, or treating traumatic brain injury in a subject, comprising administering to the subject an effective amount of a compound of ALPHA-1062 or a salt thereof.

In embodiments, the invention also relates to a method for reducing incidence of symptoms selected from the group consisting of weakness in arms and legs, balance and coordination problems, severe or increasing headaches, impaired sensory perception, impaired cognitive skills, impaired memory, impaired communication and learning, personality changes, behavior abnormalities and impaired vision and hearing as a consequence of traumatic brain injury, or treating traumatic brain injury in a subject, comprising administering to the subject an effective amount of a compound of ALPHA-1062 or a salt thereof.

In embodiments, the invention relates to a method for reducing incidence of symptoms selected from the group consisting of paralysis, coma, loss of consciousness, dilated pupils, loss of cerebrospinal fluid from the ears or nose, loss of bowel and/or bladder control, breathing problems, slow pulse, breathing problems, slow breathing rate with an increase in blood pressure and droopy eyelid or facial weakness as a consequence of traumatic brain injury, or treating traumatic brain injury in a subject, comprising administering to the subject an effective amount of a compound of ALPHA-1062 or a salt thereof.

In embodiments, the invention relates to a pharmaceutical composition comprising a compound ALPHA-1062 or salt thereof and preferably one or more pharmaceutically acceptable carriers for use in the treatment of confirmed or suspected traumatic brain injury (TBI) in a subject, characterised in that the composition is suitable for intranasal, buccal and/or sublingual application. The invention therefore relates to nose drop, a nasal spray or under-the-tongue drops in the form of a liquid composition for transmucosal administration via nasal or buccal mucosa.

In embodiments, the invention relates to a pharmaceutical composition comprising a compound ALPHA-1062 or salt thereof for use in the treatment of confirmed or suspected traumatic brain injury (TBI) in a subject via transmucosal administration, wherein the composition is an aqueous solution, comprising 2 to 40%, preferably 5 to 15% and more preferably 10% weight per volume (w/v) of the chemical substance.

In embodiments, the invention relates to a pharmaceutical composition comprising a compound ALPHA-1062 or salt thereof for use in the treatment of confirmed or suspected traumatic brain injury (TBI) in a subject, wherein the compound ALPHA-1062 or salt thereof is present at a concentration of 1 to 500 mg/mL, preferably 1 to 200 mg/mL, more preferably at a concentration of 5 to 200 mg/mL, or 5 to 100 mg/mL. These dosage ranges are provided without limiting effect on the scope of the invention. In other embodiments, efficacious doses may also be greater than can be delivered in 100 microliters in a 200 milligram per ml solution.

In embodiments, the invention relates to a pharmaceutical composition comprising a compound ALPHA-1062 or salt thereof for use in the treatment of confirmed or suspected traumatic brain injury (TBI) in a subject, wherein the compound ALPHA-1062 is present from a gluconate salt, preferably at a concentration of 50 to 100 mg/mL.

In embodiments, the invention relates to a pharmaceutical composition comprising a compound ALPHA-1062 or salt thereof for use in the treatment of confirmed or suspected traumatic brain injury (TBI) in a subject, wherein the composition is administered at a dose of 0.1 to 200 mg, preferably 1 to 100 mg, more preferably 2 to 40 mg, one to three times daily.

In embodiments, the invention relates to a pharmaceutical composition comprising a compound ALPHA-1062 or salt thereof for use in the treatment of confirmed or suspected traumatic brain injury (TBI) in a subject, wherein the composition is administered intranasally as a 2 to 40% weight per volume (w/v) solution of ALPHA-1062, at an amount of 20 to 100 microliters, preferably in a single spray event, preferably one to three times daily, preferably over a period of five to 30 days after the TBI.

In embodiments, the invention relates to a pharmaceutical composition comprising a compound ALPHA-1062 or salt thereof for use as a medicament for stimulation and/or enhancement of neurogenesis and/or neuronal recovery in the brain of a subject that is confirmed or suspected to have suffered traumatic brain injury (TBI).

In embodiments, the invention relates to a pharmaceutical composition comprising a compound ALPHA-1062 or salt thereof for use as a medicament for prevention, inhibition and/or reduction of neuronal cell loss in the brain of a subject that is confirmed or suspected to have suffered traumatic brain injury (TBI).

In embodiments, the invention relates to a pharmaceutical composition comprising a compound ALPHA-1062 or salt thereof for use as a medicament for the reduction of the size of one or more lesions and/or injuries in the brain of in a subject that is confirmed or suspected to have suffered traumatic brain injury (TBI).

In embodiments, the invention relates to a pharmaceutical composition comprising a compound ALPHA-1062 or salt thereof for use as a medicament for the preservation of brain tissue and/or neuronal tissue in the brain of in a subject that is confirmed or suspected to have suffered traumatic brain injury (TBI).

In embodiments, the invention relates to a pharmaceutical composition comprising a compound ALPHA-1062 or salt thereof for use as a medicament for reducing and/or preventing the levels and/or formation of pathological p-Tau in the brain of a subject that is confirmed or suspected to have suffered traumatic brain injury (TBI).

In embodiments, the invention relates to a pharmaceutical composition comprising a compound ALPHA-1062 or salt thereof for use as a medicament in preventing, reducing the risk of and/or slowing or reducing the development of neurodegeneration a subject that is confirmed or suspected to have suffered traumatic brain injury (TBI).

In embodiments, the invention relates to a pharmaceutical composition comprising a compound ALPHA-1062 or salt thereof for use as a medicament in preventing, reducing the risk of and/or slowing or reducing the development of neurodegeneration a subject that is confirmed or suspected to have suffered traumatic brain injury (TBI), wherein ALPHA-1062 is administered in the acute phase of TBI, or within the first 6 months after TBI or suspected TBI, preferably within 2 months, within 1 month, within 3 weeks, 2 weeks, 1 week, or within 6, 5, 4, 3 or 2 days after TBI or suspected TBI.

In embodiments, the invention relates to a pharmaceutical composition comprising a compound ALPHA-1062 or salt thereof for use as a medicament in preventing, reducing the risk of and/or slowing or reducing the development of neurodegeneration a subject that is confirmed or suspected to have suffered traumatic brain injury (TBI) by preventing, reducing levels of and/or slowing or reducing the development of pathological p-Tau.

In some of the aforementioned embodiments the confirmed or suspected traumatic brain injury (TBI) is a moderate traumatic brain injury. In some of the afore mentioned embodiments the confirmed or suspected traumatic brain injury (TBI) is a mild traumatic brain injury.

In preferred embodiments ALPHA-1062 or salt thereof is administered acutely after TBI, such as no later than 48 hours, more preferably no later than 24 hours, more preferably no later than 12, 10, 8, 6, 4, or 2 hours, after TBI. This period may be referred to as an acute phase of TBI.

In embodiments, the composition is administered to the oral cavity as a 2 to 40% weight per volume (w/v) solution of ALPHA-1062, at an amount of 20 to 100 microliters, preferably in a single spray event, preferably one to three times daily, preferably over a period of five to 30 days after the TBI.

In embodiments, the invention relates to a pharmaceutical composition comprising a compound ALPHA-1062 or salt thereof for use in the treatment of confirmed or suspected traumatic brain injury (TBI) in a subject, wherein the composition is administered intranasally, buccally or sublingually, as an about 10% weight per volume (w/v) solution at an amount of 20-100 microliters, e.g. about 50 microliters, in 1-3 administration events, preferably in a single administration event, twice daily, preferably over multiple days.

In embodiments, the pharmaceutical composition is an aqueous solution, comprising 2 to 20% weight per volume (w/v), preferably 5 to 15% weight per volume (w/v), more preferably 10% weight per volume (w/v) of the chemical substance.

To be suitable for transmucosal delivery in the oral or nasal cavity, in some embodiments the composition is formulated as high-concentration aqueous salt solutions, or as emulsions, or as selfmicroemulsifying drug delivery systems (SMEDDs) or as micronized powder formulations.

In embodiments, the dosage regimes described herein are employed using a multi-use dispenser, as described herein. Features disclosed with respect to the dispenser are also considered disclosed with respect to the dosage regime, and vice versa.

In embodiments, the concentrations of ALPHA-1062 or salt thereof employed, preferably in the aforementioned dosage regimes, are preferably in solution or as emulsions, at about 1%, 2, 3, 4, 5, 6, 7, 8, 9, 10, 11, 12, 13, 14, 15, 16, 17, 18, 19, 20, 25, 30, 35, 40, 45, or 50 wt %, or more. Dosage regimes disclosing administration of about 10 wt %, preferably 10% solutions or emulsions, may be employed alternatively at any of the aforementioned concentrations, or values similar thereto. Concentration ranges constructed form any given of the aforementioned values are also contemplated.

In some embodiments, it is intended to use ALPHA-1062 or salts thereof in manner that enables distribution of the substance in a patient after administration at a brain-to-blood concentration ratio of more than 5, preferably more than 10, more preferably between 15 and 25.

The invention also relates to a pharmaceutical composition comprising a compound ALPHA-1062 or salt thereof for use in the treatment of confirmed or suspected traumatic brain injury (TBI) in a subject, wherein the composition is administered within 24 hours of injury.

In another embodiment the composition is administered within 1 hour of injury.

In embodiments, the administration subsequent to TBI with at little delay as possible, is preferred, such as within 1 week, 6 days, 5 days, 4 days, 3 days, 2 days, or within 1 day of TBI. In embodiments, the administration is carried out within 24 hours, 12 hours, 8 hours, 6, 5, 4, 3, 2 or within 1 hour of TBI.

In embodiments, the administration subsequent to TBI is carried out within 1, 2 or 3 weeks, within 1 month or within 1 year of TBI. In embodiments, the administration is carried out within 48, 36, 24 months, 12 months, 6 months, 5, 4, 3, 2 or within 1 month of TBI. Preferably, administration of ALPHA-1062 in the acute phase of TBI, or shortly after the TBI, such as within 3, 2 or 1 month of TBI, shows beneficial effects.

The dosage regimes as described herein according to some embodiments represent novel and surprisingly beneficial developments in comparison to the prior art with respect to effective galantamine treatment. The biological and medical effect of galantamine has never previously been tested with regard to the potential effect generated by administration at high doses. Many patients in need of galantamine treatment have not been able to be treated due to the significant side effects that occur with efficacious doses of galantamine. In order to obtain meaningful levels of galantamine in the brain of subjects, the prior art teaches high but often highly intolerable doses. Because only a small fraction of orally or intranasally administered galantamine drug reaches the brain, the dose required to show an effect during treatment of brain disease is often intolerably high due to the large amount of galantamine in other tissues of the body, thereby causing unwanted side effects.

Embodiments and features of the invention described with respect to the pharmaceutical composition, the substance and salts thereof, the multi-use dispenser, and various methods described herein, are considered to be disclosed with respect to each and every other aspect of the disclosure, such that features characterizing the methods, or dispenser, may be employed to characterize the composition, or the substance and vice-versa. The various aspects of the invention are unified by, benefit from, are based on and/or are linked by the common and surprising finding of the beneficial and curative effect of the use of ALPHA-1062 in the treatment of TBI, especially when administered via the transmucosal route.

DETAILED DESCRIPTION OF THE INVENTION

The present invention relates to pharmaceutical compositions comprising a compound ALPHA-1062 or salt thereof, or to the compound ALPHA-1062 or salt thereof, for use in the treatment of confirmed or suspected traumatic brain injury (TBI) in a subject. The invention also relates to a single- or multi-use dispenser configured for intranasal or transmucosal administration of the compounds or compositions of the invention as well as to various treatment methods of TBI comprising administering a composition comprising ALPHA-1062 or salt thereof.

The preferred molecule of the present invention is ALPHA-1062, also known formerly as GLN-1062 or Memogain®. The form employed in the examples of the invention, and in one preferred embodiment of the invention, is the gluconic acid salt of ALPHA-1062 (ALPHA-1062 gluconate). For the sake of completeness, the compound ALPHA-1062 is a galantamine pro-drug, which exhibits no or negligible activity as a cholinesterase inhibitor or nicotinic modulator prior to cleavage. Upon esterase cleavage active galantamine is released.

The term “active agent” or “active pharmaceutical ingredient” (API) may however be used for ALPHA-1062, as in some embodiments it is the preferred compound of the present invention. In other embodiments, the compound galantamine may also be considered an active agent or relevant drug molecule.

The chemical name (IUPAC) of ALPHA-1062 is (4aS, 6R,8aS)-5,6,9,10,11,12-hexahydro-3-methoxy-11-methyl-4aH-[1]benzofuro[3a,3,2-ef][2]benzazepin-6-ol benzoate.

Molecular formula of free base: $C_{24}H_{25}NO_4$; Molecular formula of gluconic acid: $C_6H_{12}O_7$; Molecular weight of free base: 391.47 g/mol; Molecular weight of ALPHA-1062 gluconate: 587.61 g/mol; Conversion factor: 1 mg base=1.501 mg salt.

Chemical Structure of ALPHA-1062:

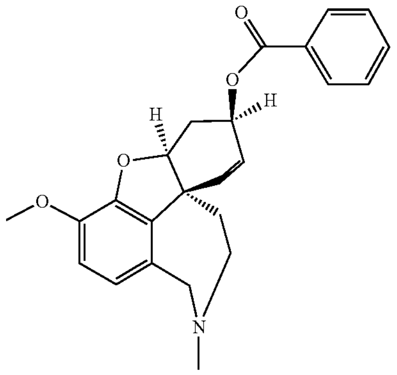

Galantamine has a formula of $C_{17}H_{21}NO_3$, and a molar mass of 287.359 g·mol$^{-1}$, and a structure of:

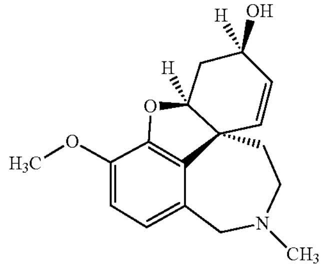

The chemical structure of the ALPHA-1062 gluconate is as follows:

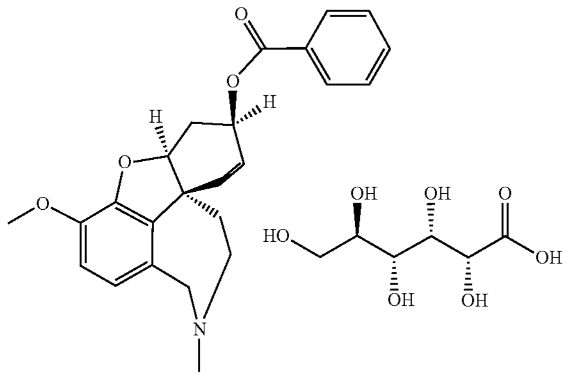

$C_{30}H_{37}NO_{11}$
Mol. Wt.: 587.61

By way of example, the gluconate salt of ALPHA-1062 can be created according to the following established general scheme:

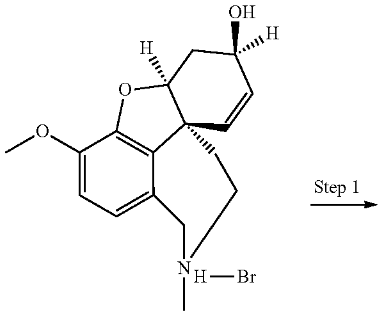

Galantamine Hydrobromide
C-022355, M012859
$C_{17}H_{22}BrNO_3$, 368.27

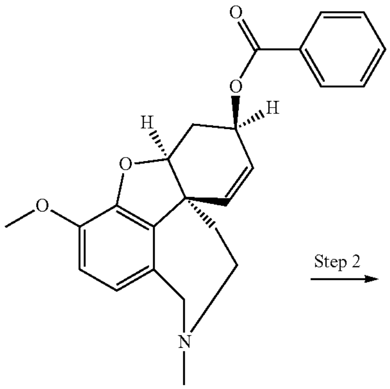

Galantaminebenzoylester
C-022356, M013080
$C_{24}H_{25}NO_4$, 391.46

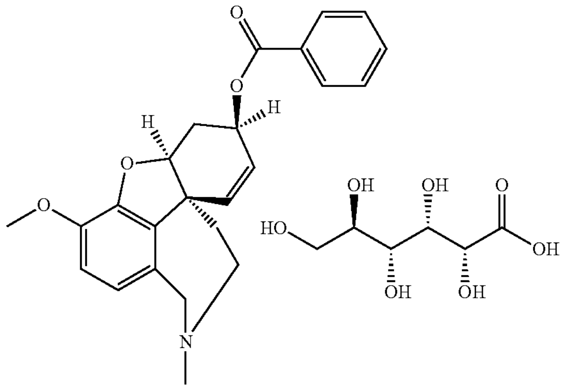

Memogain Gluconate
C-024338, M018730
$C_{30}H_{37}NO_{11}$, 587.61

In one embodiment, the composition comprises a crystalline solid form of ALPHA-1062 gluconate (Form A), wherein said crystalline form has prominent peaks at 3.61, 10.98, 14.41 and 18.44 degrees 2-theta (±0.2) in a powder X-ray diffraction pattern.

These 4 peaks are selected from the prominent peak list provided below and appear to exhibit no substantial overlap with prominent peaks in the XRPD patterns for Forms B-D, or Materials E-G, as disclosed in WO 2022/150917. In one embodiment, Form A can therefore be reliably distinguished using one or more prominent peaks, for example as mentioned above, upon comparison of the corresponding powder X-ray diffraction patterns. In one embodiment, the presence of these peaks in a powder X-ray diffraction pattern may be used to identify Form A and/or distinguish Form A from the solid forms described previously in the art, for example those described in WO2014/016430.

In one embodiment, Form A has one or more additional prominent peaks at 15.20, 17.31, 17.79, 22.77, 23.64, 24.88 and 34.31 degrees 2-theta (±0.2) in a powder X-ray diffraction pattern. These peaks are selected from the prominent peak list and appear to exhibit no substantial overlap with prominent peaks in the XRPD patterns for Forms B-D, or Materials E-G.

In one embodiment, Form A has at least five prominent peaks selected from the list consisting of 3.61, 10.98, 13.80, 14.41, 14.56, 15.08, 15.20, 17.02, 17.31, 17.79, 18.44, 19.24, 20.18, 20.91, 21.22 and 22.40 degrees 2-theta (±0.2) in a powder X-ray diffraction pattern.

Typically, not all peaks from this list need be detected in order to determine the presence of Form A in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form A, is achieved when the presence of at least three or four prominent peaks can be determined based on XRPD comparisons.

Typically, prominent XRPD peaks are the strongest low angle, non-overlapping peaks observed in a XRPD pattern. In some embodiments, the "prominent peaks" have preferably a ≥20% relative intensity, preferably ≥30% relative intensity, more preferably ≥40% relative intensity, in a powder X-ray diffraction pattern. The values of relative intensity may however vary depending on device or analysis mode and are not inherently limiting to the solid forms described herein.

In one embodiment, Form A has peaks at 7.25 and/or 12.67 degrees 2-theta (±0.2) in a powder X-ray diffraction pattern. These peaks are of relatively low intensity compared to the peaks outlined above as predominant peaks. However, peaks at 7.25 and/or 12.67 degrees 2-theta appear to be absent in all other patterns for Forms B-D or Materials E-G.

In one embodiment, the peaks are determined using powder X-ray diffraction analysis in transmission mode.

In one embodiment, Form A has at least three peaks selected from the list consisting of 10.98, 14.41, 17.31, 18.44 and 22.40 degrees 2-theta (±0.2) in a powder X-ray diffraction pattern. In one embodiment, said three peaks are within the five peaks with the highest relative intensity in a powder X-ray diffraction pattern obtained using analysis in transmission mode. In one embodiment, these five peaks are the most intense peaks in the XRPD pattern using transmission mode, as outlined in the examples below.

In one embodiment, the peaks are determined using powder X-ray diffraction analysis in reflectance mode.

In one embodiment, Form A has at least three peaks selected from the list consisting of 3.61, 7.25, 10.98, 14.56 and 22.40 degrees 2-theta (±0.2) in a powder X-ray diffraction pattern. In one embodiment, said three peaks are preferably within the five peaks with the highest relative intensity in a powder X-ray diffraction pattern obtained using analysis in reflectance mode. In one embodiment, these five peaks are the most intense peaks in the XRPD pattern using reflectance mode, as outlined in the example below.

In one embodiment, Form A has one or more peaks selected from the list consisting of 3.61, 7.25, 10.98, 14.56, 22.40 degrees 2-theta (±0.2) in a powder X-ray diffraction pattern. These peaks are also observable from the XRPD pattern using reflectance mode.

In one embodiment, Form A has one or more doublets selected from the list consisting of 14.41 and 14.56, 15.08 and 15.20, and 24.88 and 25.09 degrees 2-theta (+0.2) in a powder X-ray diffraction pattern. These doublets may be used to identify Form A, and optionally distinguish the Form from other forms.

Provided below is a Table of the typically observed XRPD pattern peaks for Form A collected in transmission mode.

Peak list Form A: Peak list determined from the powder X-ray diffraction pattern of Form A, according to FIG. 8. Accuracy of degrees 2-theta is provided at 2 decimal points, some variation dependent on batch or device may be evident.

| 2θ (°) | d (Å) | I (%) |
|---|---|---|
| 3.61* | 24.5 | 47 |
| 7.25 | 12.2 | 18 |
| 10.52 | 8.40 | 14 |
| 10.98* | 8.05 | 100 |
| 11.71 | 7.55 | 4 |
| 12.67 | 6.98 | 23 |
| 13.46 | 6.57 | 10 |
| 13.80* | 6.41 | 45 |
| 14.41* | 6.14 | 71 |
| 14.56* | 6.08 | 52 |
| 15.08* | 5.87 | 40 |
| 15.20* | 5.82 | 46 |
| 16.16 | 5.48 | 25 |
| 16.44 | 5.39 | 22 |
| 17.02* | 5.20 | 46 |
| 17.31* | 5.12 | 66 |
| 17.79* | 4.98 | 41 |
| 18.24 | 4.86 | 8 |
| 18.44* | 4.81 | 67 |
| 19.24* | 4.61 | 56 |
| 19.43 | 4.56 | 10 |
| 19.80 | 4.48 | 24 |
| 20.18* | 4.40 | 40 |
| 20.91* | 4.24 | 64 |
| 21.22* | 4.18 | 57 |
| 21.54 | 4.12 | 19 |
| 22.09 | 4.02 | 19 |
| 22.40* | 3.97 | 86 |
| 22.77* | 3.90 | 41 |
| 23.64* | 3.76 | 39 |
| 24.30 | 3.66 | 13 |
| 24.88* | 3.58 | 41 |
| 25.09* | 3.55 | 44 |
| 25.44 | 3.50 | 9 |
| 25.76 | 3.46 | 15 |
| 25.89 | 3.44 | 25 |
| 26.37 | 3.38 | 12 |
| 26.62 | 3.35 | 5 |
| 26.91 | 3.31 | 5 |
| 27.19 | 3.28 | 17 |
| 27.37 | 3.26 | 19 |
| 27.82 | 3.20 | 23 |
| 27.99 | 3.18 | 35 |
| 28.95 | 3.08 | 14 |
| 29.34 | 3.04 | 11 |
| 29.83 | 2.99 | 21 |
| 30.37 | 2.94 | 15 |
| 30.92 | 2.89 | 17 |
| 31.68 | 2.82 | 6 |
| 32.44 | 2.76 | 9 |
| 33.39 | 2.68 | 5 |
| 34.31 | 2.61 | 34 |

*Peaks may in some embodiments be considered as prominent peaks observed in the XRPD pattern.

In one embodiment, Form A exhibits an onset of melting at a temperature of 116-120° C., preferably at about 117° C., when assessed using differential scanning calorimetry (DSC).

In one embodiment, Form A exhibits a weight loss of <1%, preferably <0.5%, more preferably less than <0.3%, or <0.2%, prior to the onset of melt using DSC when assessed using Thermo-Gravimetric Analysis (TGA).

As used herein, crystalline preferably means a material that has an ordered, long range molecular structure. The degree of crystallinity of a crystal form can be determined by many techniques including, for example, powder X-ray diffraction, moisture sorption, differential scanning calorimetry, solution calorimetry, and dissolution properties.

Crystalline organic compounds consist of a large number of atoms that are arranged in a periodic array in three-dimensional space. The structural periodicity normally manifests distinct physical properties, such as sharp, explicit spectral features by most spectroscopic probes (e.g., X-ray diffraction, infrared and solid-state NMR). X-ray diffraction (XRD) is acknowledged to be one of the most sensitive methods to determine the crystallinity of solids. Crystals yield explicit diffraction maxima that arise at specific angles consistent with the lattice interplanar spacings, as predicted by Bragg's law. On the contrary, amorphous materials do not possess long-range order. They often retain additional volume between molecules, as in the liquid state. Amorphous solids normally unveil a featureless XRD pattern with broad, diffuse halos because of the absence of the long-range order of repeating crystal lattice.

Crystalline forms are preferred in many pharmaceutical applications. Crystalline forms are generally thermodynamically more stable than amorphous forms of the same substance. This thermodynamic stability is preferably reflected in the improved physical stability of the crystalline form. The regular packing of the molecules in the crystalline solid preferably denies the incorporation of chemical impurities. Hence crystalline materials generally possess higher chemical purity than their amorphous counterparts. The packing in the crystalline solid generally constrains the molecules to well defined lattice positions and reduces the molecular mobility that is the prerequisite for chemical reactions. Hence, crystalline solids, with very few notable exceptions, are chemically more stable than amorphous solids of the same molecular composition. Preferably, the crystalline forms of the ALPHA-1062 gluconate disclosed in the present application possess one or more of the advantageous chemical and/or physical properties disclosed herein.

As used herein, the term stable may relate to either chemical stability or to polymorph stability. Polymorph stability refers to the likelihood of a polymorph form remaining in its specific crystalline state under suitable storage conditions. For example, a stable polymorph form will maintain at least about 95% by weight, preferably at least about 98% by weight, and more preferably at least about 99% by weight or more of the crystalline form, in other words the form remains unchanged after storage under the indicated conditions for the indicated time. In the context of the present invention, Form A of the ALPHA-1062 gluconate appears to show good stability for example under conditions of storage at room temperature, and at low water activities, such at or under about 43% RH or of less than 0.12 $a_w$, for multiple months. In some embodiments, Form A shows good chemical stability. In other words, ALPHA-1062 gluconate as Form A shows low, negligible or no conversion to distinct chemical structures, after storage under the appropriate conditions.

Powder X-ray diffraction (PXRD) measures the diffraction pattern of a crystalline material. Each active pharmaceutical ingredient (API) will produce a specific pattern depending on the structure of its crystal lattice. Each polymorph, pseudopolymorph, polymorph salt, or co-crystalline material will have its own specific pattern. For this reason, PXRD of an API can be carried out in controlled conditions to assess the presence or absence of crystalline material and any form conversions.

PXRD can also be used to determine if any change in crystalline form in the drug product has occurred during e.g. storage or stability studies. The identification of a crystalline form therefore relies on the presence of detectable diffraction peaks for any given crystalline form. In addition, the API peaks must be distinguishable from any crystalline excipient peaks, should a composition be assessed post-formulation. PXRD can also be used as a qualitative and sometime quantitative assessment of the degree of crystallinity of a pure API. A skilled person can assess PXRD patterns and identifying the presence and/or absence of suitable peaks that can be employed to characterize any given crystalline form of an API without undue effort.

In some embodiments, the peaks determined by a PXRD analysis are essentially the same as those presented in the examples below. The term "essentially the same" with reference to PXRD means that variabilities in peak positions and relative intensities of the peaks are to be taken into account. For example, a typical precision of the 2-Theta values is in the range of ±0.2° 2-Theta.

As used herein, characteristic XRPD peaks are a subset of the representative peaks from XRPD patterns of a crystalline form of a material that statistically can be proven to differentiate it from the other crystalline forms of that material. Not all crystalline polymorphs of a material necessarily have characteristic peaks.

As used herein, prominent XRPD peaks are typically the strongest low angle, non-overlapping peaks observed in the XRPD pattern. In some embodiments, the "prominent peaks" have preferably a ≥20% relative intensity, preferably ≥30% relative intensity, more preferably ≥40% relative intensity, in a powder X-ray diffraction pattern.

As used herein, representative XRPD Peaks are peaks from XRPD patterns of a crystalline form of a material that statistically show no bias from particle size/shape or preferred orientation during repeated samples and measurements.

As used herein, preferred orientation is phenomena observed in XRPD analyses where due to size/shape of the particles and the pattern collection technique employed it is very difficult or impossible to randomly orient the particles of the material during collection to achieve a pattern with statistically consistent intensities.

With respect to the relative intensities and the prominent peaks of the powder X-ray diffraction patterns mentioned above, the provided values of relative intensity are not intended as limiting for the identification of the prominent or characteristic peaks mentioned. As is known to a skilled person, the relative peak intensities will show some inter-apparatus variability, batch-to-batch variability, as well as variability due to degree of crystallinity, preferred orientation, sample preparation, and as such are provided as an indication and as a qualitative measure only, but not a limiting definition, of the intensities of the peaks in the powder X-ray diffraction patterns.

The term "prominent peak" in the context of defining the present invention is therefore not limited to the respective relative intensities provided above, and any one or more of the respective peaks may be determined as a prominent peak for any given form of ALPHA-1062 gluconate. Preferably at least 1, 2, 3 or 4 prominent peaks are used to characterize a crystalline form, in other embodiments, at least 5, 6, 7, 8 9 or 10 prominent peaks may be employed. A prominent peak is therefore also not limited to a peak unique to any given crystal form, rather the peak can, optionally in combination with a number of other peaks from the PXRD pattern, be used to identify a crystal form. In the context of the present invention, crystal Forms A-D may share multiple prominent peaks, but also exhibit peaks distinct from one another that can be used to differentiate between any two forms. In some embodiments, the prominent peaks mentioned in the embodiments of the invention may also be characteristic peaks and/or representative peaks.

As used herein, the term "self-preserving" is a description of an anti-microbial property of a compound, namely of ALPHA-1062 or salt thereof, or a composition comprising such an agent, that does not require the presence of an additional antimicrobial preserving agent.

In preferred embodiments, a self-preserving liquid composition maintains the absence of, has low or negligible numbers, or relatively slow rates of growth, of viable microbes present in the composition, or reduces the numbers of viable microbes in the composition. In some embodiments, the property "self-preserving" indicates that the rate of microbial expansion (cell growth or division) in the composition over time is lower than in the absence of the relevant compound (ALPHA-1062). As used herein, a "self-preserving" liquid composition will therefore exhibit lower numbers of viable microbes in comparison to a composition without such "self-preserving" properties. In some embodiments, a "self-preserving" composition comprises no additional anti-microbial preservatives and shows no or negligible increase in the numbers of viable microbes in the composition for an extended period, preferably at least 14 days, or for at least 28 days.

As used herein, the term "anti-microbial" describes the property of a compound or composition to reduce numbers of viable microbes or show no or a negligible increase in the numbers of viable microbes in the composition for at least 14 days, or for at least 28 days. In some embodiments of the invention, pathogenic fungi, gram-negative and/or gram-positive bacteria can be killed or inhibited in growth by ALPHA-1062 or salts thereof. In some embodiments, the term "anti-microbial" is defined according to the guidelines set out for preservatives in the USP 51 test. The term may therefore depend on the type of microbe and duration of test. The concentration of an added antimicrobial preservative is usually kept at a minimum, or avoided completely, especially if the active ingredients of the formulation possess an intrinsic antimicrobial activity, as is the case with ALPHA-1062 or salts thereof. Antimicrobial effectiveness, whether inherent in the product or whether produced because of the addition of an antimicrobial preservative, must commonly be demonstrated for multiple-dose topical and oral dosage forms and for other dosage forms such as ophthalmic, optic, nasal, irrigation, and dialysis fluids. As described herein, the agent ALPHA-1062 exhibits anti-microbial preservative properties, inherent in the molecule, and therefore requires little, or no additional usage of additional preservatives in the composition of the invention.

"Traumatic Brain Injury" (TBI) is a disruption in the normal function of the brain that can be caused by a blow, bump or jolt to the head, the head suddenly and violently hitting an object or when an object pierces the skull and enters brain tissue. Observing one of the following clinical signs constitutes alteration in the normal brain function: Loss of or decreased consciousness, loss of memory for events before or after the event (amnesia), focal neurological deficits such as muscle weakness, loss of vision, change in speech, alteration in mental state such as disorientation, slow thinking or difficulty concentrating Symptoms of a TBI can be mild, moderate, or severe, depending on the extent of damage to the brain. Mild cases may result in a brief change in mental state or consciousness. Severe cases may result in extended periods of unconsciousness, coma, or even death.

Symptoms of TBI can vary greatly depending on the severity of the head injury and may comprise vomiting, lethargy, headache, confusion, paralysis, coma, unconsciousness, dilated pupils, visual disturbances (blurred or double vision, intolerance to bright light, loss of eye movements, blindness) dizziness and imbalance, difficulty swallowing, numbness or tingling sensation, drooping eyelids or weak face, loss of bowel or bladder control.

Short and long term symptoms of TBI can further comprise one or more of the symptoms selected from the group comprising dizziness, balance problems, headaches, nausea, vomiting, light sensitivity, impaired memory, sleep abnormalities, impaired concentration and impaired vision, weakness in arms and legs, balance and coordination problems, severe or increasing headaches, impaired sensory perception, impaired cognitive skills, impaired memory, impaired communication and learning, personality changes, behavior abnormalities, impaired vision and hearing, paralysis, coma, loss of consciousness, dilated pupils, loss of cerebrospinal fluid from the ears or nose, loss of bowel and/or bladder control, breathing problems, slow pulse, breathing problems, slow breathing rate with an increase in blood pressure, droopy eyelid or facial weakness, hematoma, contusion, intracerebral hemorrhage, subarachnoid hemorrhage, diffuse injuries, diffuse axonal injury, ischemia, primary brain injury and/or secondary brain injury.

As used herein, "primary brain injuries", i.e. such as skull fractures, localized injuries or diffuse axonal injury, occur at the time of the initial brain injury, i.e. a TBI event, and cannot be prevented, but only addressed by subsequent treatment. One goal of the treatment of an initial brain injury is to prevent or reduce further, or "secondary brain injuries". The term "secondary brain injury" typically refers to the changes that evolve after the initial injury, usually within minutes, hours, days or sometimes even months. It comprises an entire series of events or stages of cellular, chemical, tissue, or blood vessel changes in the brain that contribute to further destruction of brain tissue.

TBI can cause "mass lesions," an area of localized injury such as bruises and bruises that increase pressure in the brain. Secondary injuries caused by TBI or accompanying TBI can comprise one or more of the following injuries: hematoma, (brain) bruises, intracerebral hemorrhage, subarachnoid hemorrhage, diffuse Injuries, diffuse axon injury, ischemia and/or skull fractures.

In embodiments of the invention "hematoma" refers to a blood clot in the brain or on its surface that can appear anywhere in the brain. An epidural hematoma is a collection of blood between the dura mater (the protective covering of the brain) and the inside of the skull. A subdural hematoma is a collection of blood between the dura mater and the arachnoid layer that is located on the surface of the brain.

In embodiments of the invention "bruise" or "brain bruise" may refer to a bruise of the brain tissue that is pathologically comparable to bruises on other parts of the body. A brain bruise consists of areas of injured or swollen brain mixed with blood that has leaked from arteries, veins, or capillaries. The most common bruises are at the base of the front parts of the brain, but they can appear anywhere.

In embodiments of the invention "intracerebral hemorrhage" (ICH) refers to hemorrhages in the brain tissue that can be related to other brain injuries, especially bruises. Depending on the size and location of the bleeding it could be surgically removed.

In embodiments of the invention "subarachnoid hemorrhage" (SAH) is caused by bleeding into the subarachnoid space. It appears as diffuse blood that spreads thinly over the surface of the brain and is common after TBI. Most cases of SAH related to head trauma are mild. Hydrocephalus can result from severe traumatic SAH.

In embodiments of the invention "diffuse Injuries" describes microscopic changes that do not appear on CT scans and are scattered throughout the brain, which can occur as a result of TBI. This category of injury, known as diffuse brain injury, can occur with or without an associated mass lesion.

In embodiments of the invention "diffuse axon injury" refers to impaired function and gradual loss of axons. These long extensions of nerve cells enable them to communicate with one another. If enough axons are damaged in this way, the ability of nerve cells to communicate with one another and integrate their function can be lost or severely impaired, which can lead to severe disabilities for the patient.

In embodiments of the invention "ischemia" describes another type of diffuse injury, or an insufficient blood supply to certain parts of the brain. A high percentage of TBI patients experience a decrease in blood supply to very low levels. This is crucial because a brain that has just suffered a traumatic injury is particularly sensitive to mild reductions in blood flow. Changes in blood pressure in the first few days after a head injury can also have an adverse effect. Ischemia is also considered to be a major cause of secondary brain injury.

In embodiments of the invention "skull fractures" refer to linear skull fractures or simple fractures in the skull that can accompany TBI.

Potential forces strong enough to cause a fractured skull can damage the brain below. Skull fractures can be alarming when discovered during a patient exam. Fractures at the base of the skull are problematic because they can injure nerves, arteries, or other structures. If the fracture extends into the sinuses, a leakage of cerebrospinal fluid from the nose or ears can occur. Depressed skull fractures, in which part of the bone presses on or into the brain, can also occur.

In embodiments of the invention, ALPHA-1062 administration may induce preventing, reducing the risk of, reducing the levels of and/or slowing or reducing the development of pathological p-Tau. As used herein, "p-Tau" refers to phosphorylated Tau protein. The tau proteins comprise six soluble protein isoforms produced by alternative splicing from the gene MAPT (microtubule-associated protein tau). They have roles primarily in maintaining the stability of microtubules in axons and are abundant in neurons of the central nervous system (CNS). The accumulation of pathologically phosphorylated Tau in neurons is typically associated with neurofibrillary degeneration and is observed in various neurodegenerative diseases. Pathologies and dementias of the nervous system such as Alzheimer's disease and Parkinson's disease are associated with phosphorylated Tau proteins that have become insoluble aggregates called neurofibrillary tangles. The mechanism of tau aggregation is still not completely elucidated, but several factors including tau phosphorylation appear to be associated with and/or induce this process. Thus, pathological p-Tau is often considered both a marker for neurodegeneration and a causative factor in neurodegeneration.

A "pro-drug" in general describes a medication or compound that, after administration, is metabolized within the body into a pharmacologically active drug. A prodrug can be administered instead of its corresponding drug compound to improve the absorption, distribution, metabolism, and/or excretion of the corresponding drug. The use of prodrugs with improved bioavailability is especially advantageous, if the corresponding drug is poorly absorbed, e.g., through the gastrointestinal route. The administration of a prodrug may reduce adverse or undesired side-effects of a corresponding drug and/or improve the drugs bioavailability and/or absorption.

"Pro-drugs" are typically per se therapeutically inactive agents that are predictably transformed in specific locations in the body to active metabolites. In this sense, pro-drugs are inactive precursors of parent drugs that undergo transformation into active agents in vivo by enzymatic cleavage or chemical spontaneous process(es) in a predictable fashion. In the pro-drugs according to some embodiments discussed herein, there exists preferably a covalent ester linkage between the parent drug and the selected pro-moiety, and upon cleavage of this ester bond, ideally in the target organ brain, the inactive pro-drug releases the active parent drug at or close to its target sites in the CNS.

Herein, a "pro-drug" may refer to ALPHA-1062 or salts thereof, without being limited thereto. In some embodiments of the invention the administration of the pro-drug ALPHA-1062 or salts thereof is intended to reduce or prevent (partially or entirely) galantamine-related adverse effects and/or improve the transmucosal absorption of galantamine compounds.

A goal of some embodiments according to the present invention is therefore to present novel CNS therapeutics for the treatment of TBI having optimal brain bioavailability due to being formulated as lipophilic pro-drugs and administered via transmucosal absorption pathways in the oral or nasal cavity.

The ALPHA-1062 pro-drugs disclosed herein are passively transported through the blood-brain barrier (BBB) into the brain. These ALPHA-1062 pro-drugs are essentially pharmacologically inactive and hence do not produce any significant GI or other side effects, as long as they remain un-cleaved in the particular tissue. After enzymatic cleavage, from each molecule of pro-drug one molecule of parent drug is formed, thereby producing the full pharmacological effect of the drug. If cleavage is preferentially in the brain, due to enhanced distribution into this organ, and the availability of suitable endogenous enzyme(s) therein, a persistently higher concentration of drug at the target sites in the CNS and consequently larger medically beneficial effects may be achieved. Preferential transport to the target organ brain is further optimized in a surprising and beneficial manner by transmucosal routes of administration in the oral or nasal cavity.

In summary, these features of the formulations of ALPHA-1062 or salts thereof described for some embodiments herein, foster delivery to the brain of more persistent and higher concentrations of pro-drug than can be achieved by oral administration in form of tablets of the unmodified drug. The improved distribution of the drug to the brain dramatically reduces all locally produced side effects in the GI tract, thereby permitting immediate efficacious dosing of the drug at its CNS-located target molecules, e.g. nicotinic receptors and acetyl cholinesterase.

As the "blood-brain barrier" (BBB), located at the level of the brain capillaries, is the major barrier to the passage of drugs from the blood compartment to the brain, initial focus on optimizing penetration of the pro-drugs through the BBB yielded promising results. The brain microvessel endothelial cells forming the BBB have as typical morphological characteristics tight junctions between cells, absence of fenestrations and diminished pinocytotic activity. A variety of enzymes further contributes to the restrictive nature of the BBB. The ability of drugs to cross the BBB mostly depends on their physicochemical properties, such as their lipophilicity. Consequently, the compounds considered in the present disclosure all are pro-drugs with improved lipophilicity, in comparison to their parent compounds.

The "BBCR" is to be understood as the brain-to-blood drug concentration ratio after transport equilibrium via the BBB has been achieved.

The term "transmucosal administration" relates to the transport of a pharmaceutical agent through, or across, a mucous membrane. The transmucosal routes of administration of the present invention are defined as intranasal, buccal and/or sublingual.

"Nasal or intranasal administration" relates to any form of application of the prodrug or pharmaceutical composition thereof to the nasal cavity. The nasal cavity is covered by a thin mucosa which is well vascularised. Therefore, a drug molecule can be transferred quickly across the single epithelial cell layer without first-pass hepatic and intestinal metabolism. Intranasal administration is therefore used as an alternative to oral administration of for example tablets and capsules, which lead to extensive degradation in the gut and/or liver.

"Buccal administration" relates to any form of application that leads to absorption across the buccal mucosa, preferably pertaining to adsorption at the inside of the cheek, the surface of a tooth, or the gum beside the cheek.

"Sublingual administration" refers to administration under the tongue, whereby the pro-drug comes in contact with the mucous membrane beneath the tongue and diffuses through it.

Rapid absorption in the oral cavity is best achieved by sublingual administration, as the mucosal thickness in this area is lower than in other buccal areas, in addition to being significantly less keratinized (Shojaei A (1998) Buccal mucosa as a route for systemic drug delivery: a review. J Pharm Pharmaceut Sci 1: 15-30). Fast dissolving sublingual formulations according to some embodiments of the invention, such as rapidly degrading tablets or liquid-filled capsules, can additionally help reducing enzymatic degradation of pro-drug in saliva. The nasal cavity also provides a promising starting point for alternative administration regimes, with its large surface area, high vasculature and low enzymatic environment. Intranasal delivery according to some embodiments of the invention is capable of providing a similarly high level of bioavailability as intravenous administration with the advantages of non-invasiveness, ease of self-administration, patient comfort and patient compliance in comparison to the latter. These advantages may have been known generally by practitioners of the art; however, significant hurdles remain for developing such application routes. For chronic systemic delivery, the problems of epithelial damage and toxicity need to be solved, and that for sufficient bioavailability high concentrations of drug in small volumes of vehicle are provided. This requires first selection of suitable chemical compounds that enable the required formulations and concentrations, in addition to finding appropriate methods for administration and finally developing preferred salts and/or solutions thereof that allow optimal administration of effective substance to the brain.

Pharmaceutical compositions suitable for buccal and/or sub-lingual administration may comprise in some embodiments additional "pharmaceutically acceptable carriers", for example a buccal dosage unit may comprise the active agent to be administered in addition to a polymeric carrier that bioerodes and provides for delivery of the active agent over a predetermined time period, and, preferably, a lubricant, such as magnesium stearate. Additional carrier agents are known to one in the art. This active agent can be physically compounded with materials of some or all of classes of ingredients that function as pH controls, preservative agents, viscosity control agents, absorption enhancers, stabilizing agents, solvents, and carrier vehicles. Such agents may in some embodiments of the invention be present in either solid or liquid forms of the pharmaceutical composition.

A "self-microemulsifying drug delivery system" (SMEDDS) may be present in said pharmaceutical composition in some embodiments, meaning a drug delivery system that uses a microemulsion achieved by chemical rather than mechanical means. That is, by an intrinsic property of the drug formulation, rather than by special mixing and handling. It employs the familiar effect displayed by anethole in many anise-flavored liquors. Microemulsions have significant potential for use in drug delivery, and SMEDDS (including so-called "U-type" microemulsions) are the best of these systems identified to date. SMEDDS are of particular value in increasing the absorption of lipophilic drugs taken by mouth. SMEDDS in may include in a non-limiting manner include formulations of the drugs anethole trithione, oridonin, curcumin, vinpocetine, tacrolimus, berberine hydrochloride, nobiletin and/or piroxicam. Other emulsions are generated by mechanical means, such as mixing, sonicating, vortexing or homogenizing. The first drug marketed as a SMEDD was cyclosporin, and it had significantly improved bioavailability compared with the conventional solution. SMEDDS offer numerous advantages: spontaneous formation, ease of manufacture, thermodynamic stability, and improved solubilization of bioactive materials. Improved solubility contributes to faster release rates and greater bioavailability. For many drugs taken by mouth, faster release rates improve the drug acceptance by consumers. Greater bioavailability means that less drug need be used; this may lower cost and does lower the stomach irritation and toxicity of drugs taken by mouth. For oral use according to some embodiments, SMEDDS may be formulated as liquids, and are applicable for transmucosal administration.

The pharmaceutical composition may in some embodiments include one or more pharmaceutically acceptable carriers, or excipients. The term "excipient" means a pharmacologically inactive component such as a diluent, disintegrant, carrier, and the like, of a pharmaceutical product. The excipients that are useful in preparing a pharmaceutical composition are generally safe, non-toxic and are acceptable for veterinary as well as human pharmaceutical use. Reference to an excipient includes both one excipient and more than one excipient. The excipients are described herein in some embodiments according to "wt %", or "percentage by weight".

"Administration" or "treatment," as it applies to an animal, human, experimental subject, cell, tissue, organ, or biological fluid, refers to contact of a pharmaceutical, therapeutic, diagnostic agent, compound, or composition to the animal, human, subject, cell, tissue, organ, or biological fluid. "Administration" and "treatment" can refer in some embodiments, e.g., to therapeutic, placebo, pharmacokinetic, diagnostic, research, and experimental methods. "Treatment," as it applies to a human, veterinary, or research subject, refers to therapeutic treatment, prophylactic or preventative measures, to research and diagnostic applications. As used herein, "administer" or "administration" refers to the delivery of the drug or agent of the present invention or a pharmaceutical composition thereof to an organism for the purpose of prevention or treatment of a brain disease associated with cognitive impairment. Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, sublingual, buccal or intraocular injections. The preferred route of administration is transmucosal.

In some embodiments, the liquid formulations are configured for any one or more of the above administration modes. A skilled person is aware of technical means employed in configuring compositions for specific modes of administration. For example, a composition configured for nasal administration may be formulated, packaged, or prepared in a different manner from compositions prepared for oral administration.

Pharmaceutical compositions of the present invention may be manufactured in some embodiments by processes well known in the art, e.g., by means of conventional mixing, dissolving, micronizing, granulating, dragee-making, levigating, emulsifying, encapsulating, entrapping, dissolving or lyophilizing processes. Pharmaceutical compositions for use in accordance with the present invention may in some embodiments be formulated in conventional manner using one or more physiologically acceptable carriers including excipients and auxiliaries that facilitate processing of crystals or other forms of the present invention into preparations that can be used pharmaceutically. Proper formulation is dependent upon the route of administration chosen.

In some embodiments for injection or transmucosal administration, a compound of the present invention or a pharmaceutical composition thereof may be formulated in aqueous solutions, preferably in physiologically compatible buffers such as Hanks' solution, Ringer's solution, or physiological saline buffer. For transmucosal administration according to some embodiments, penetrants appropriate to the barrier to be permeated are used in the formulation. Such penetrants are generally known in the art.

In some embodiments for oral administration, a compound of the present invention or a pharmaceutical composition thereof can be formulated by combining a compound of the present invention with pharmaceutically acceptable carriers well known in the art. Such carriers enable compounds of the present invention in some embodiments to be formulated as tablets, pills, lozenges, dragees, capsules, liquids, gels, syrups, slurries, suspensions and the like, for oral ingestion by a patient. Pharmaceutical preparations for oral use can be made in some embodiments using a solid excipient, optionally grinding the resulting mixture, and processing the mixture of granules, after adding other suitable auxiliaries if desired, to obtain tablets or dragee cores. Useful excipients are, in particular, fillers such as sugars, starch and other materials. If desired, disintegrating agents may be added.

"Effective amount" also relates to an amount of the prodrug substance or pharmaceutical composition thereof, sufficient to allow or facilitate the amelioration and/or diagnosis of a symptom or sign of a disorder, condition, or pathological state. The term "effective amount" or "therapeutically effective amount" used interchangeably, is defined to mean the amount or quantity of the compound (e.g. ALPHA-1062 or salts thereof), which is sufficient to elicit an appreciable biological response when administered to the patient in some embodiments. It will be appreciated that the precise therapeutic dose will depend on the age and condition of the patient, nature of the condition to be treated and will be at the ultimate discretion of the attendant physician. The election of dose in this case will relate to both therapeutic effect on the treatment of neurological disease, in addition to an effective amount with respect to the antimicrobial effect. Both amounts may be assessed and determined by a skilled person.

The invention encompasses in some embodiments administration of an effective amount of chemical substance as described herein to a patient or subject in need thereof. "Effective amount" or "therapeutically effective amount" means an amount sufficient to ameliorate a symptom or sign of a disorder or physiological condition or an amount sufficient to permit or facilitate a diagnosis of the disorder or physiological condition. An effective amount for a particular patient or veterinary subject may vary depending on factors such as the condition being treated, the overall health of the patient, the method route and dose of administration and the severity of side effects. An effective amount can be the maximal dose or dosing protocol that avoids significant side effects or toxic effects. The effect will result in an improvement of a diagnostic measure, parameter, or detectable signal by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject.

Herein, the terms "subject", "patient" or "individual" may be used interchangeably. In preferred embodiments of the invention a subject may be an animal, a mammal or a human, even more preferably a human.

As used herein, the term "liquid" refers to its common meaning, including compositions with nearly incompressible fluid that conforms to the shape of its container but retains a (nearly) constant volume independent of pressure.

As used herein "pharmaceutical compositions in liquid form" are liquids comprising one or more pharmaceutically active agents, suitable for administration to a subject, preferably a mammal, more preferably human subject. Liquid dosage forms are typically pharmaceutical products which involve a mixture of drug components and nondrug components (excipients). Liquid dosage forms are prepared: a) by dissolving the active drug substance in an aqueous or non-aqueous solvent (e.g. water, glycerin, ether, alcohol), or b) by suspending the drug in appropriate medium, or c) by incorporating the drug substance into an oil or water phase, such as suspensions, emulsions, syrups or elixirs. The solutions described herein are characterized by good solubility in water, as is evident for the salts of ALPHA-1062.

"Emulsions" may also be produced and employed for transmucosal administration, as disclosed in the art. An "emulsion" is a mixture of two or more liquids that are normally immiscible (unmixable or unblendable). Emulsions are part of a more general class of two-phase systems of matter called colloids. Although the terms colloid and emulsion are sometimes used interchangeably, emulsion should be used when both phases, dispersed and continuous, are liquids. In an emulsion, one liquid (the dispersed phase) is dispersed in the other (the continuous phase). Examples of emulsions include creams, ointments, liniments (balms), pastes, films, or liquids, depending mostly on their oil-to-water ratios, other additives, and their intended route of administration. Many are topical dosage forms and may be used on the surface of the skin, transdermally, transmucosally, ophthalmically, rectally or vaginally. A highly liquid emulsion may also be used orally, intranasally or may be injected in some cases.

Pharmaceutical compositions of the present invention may be manufactured by processes well known in the art, e.g., by means of conventional mixing, dissolving, granulating, micronizing, emulsifying, encapsulating, entrapping, dissolving or lyophilizing processes. Pharmaceutical compositions for use in accordance with the present invention may be formulated in conventional manner using one or more physiologically acceptable carriers including excipients and auxiliaries that facilitate processing the API into preparations that can be used pharmaceutically. Proper formulation is dependent upon the route of administration chosen.

For injection or transmucosal administration, the API or a pharmaceutical composition thereof may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the API the present invention or a pharmaceutical composition thereof can in some embodiments be formulated by combining the API with pharmaceutically acceptable carriers well known in the art. Such carriers enable substances, such as in crystal form, of the present invention to be formulated as tablets, pills, lozenges, capsules, liquids, gels, syrups, slurries, suspensions, solutions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

A composition of the present invention may in some embodiments also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulating materials such as suspending, stabilizing, and/or dispersing agents.

Various liquid compositions comprising ALPHA-1062 or salt thereof, in addition to solutions, are contemplated, such as emulsions, suspensions, and the like. In one embodiment, the liquid pharmaceutical composition comprising ALPHA-1062 or salt thereof comprises a sufficient amount or volume of composition for multiple administration events (doses) to a subject. The invention therefore also relates to pharmaceutical compositions comprising ALPHA-1062 or salt thereof in a solution configured for multi-dose administration to a subject in need thereof.

Pharmaceutical compositions for parenteral (any route that is not gastrointestinal) administration include aqueous solutions of a water-soluble form of the API. Additionally, suspensions of drug or pro-drug of the present invention or pharmaceutical compositions thereof may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds of the present invention or a pharmaceutical composition thereof to allow for the preparation of highly concentrated solutions.

In some embodiments, the composition comprising active ingredient may be in powder form. For example, the powder may be prepared for constitution with a suitable vehicle, e.g., sterile, pyrogen-free water, before use. In some embodiments, the powder formulation is for administration to a subject. For example, powder formulations, such as micronized powder formulations, may be administered intranasally, or via other methods, such as via transmucosal administration, by spraying or otherwise applying the powder formulation to a subject, preferably to a mucosal surface of a subject.

The antimicrobial properties of ALPHA-1062 as described herein are beneficial for not only liquid formulations, such as solutions, suspensions and emulsions, but also to solid or powder formulations. Powder formulations suitable for transmucosal administration also benefit from the antimicrobial properties of ALPHA-1062 and the absence of additional antimicrobial preservatives, made possible by the finding that ALPHA-1062 is itself antimicrobial. Similarly, solid compositions may also benefit from the antimicrobial properties of ALPHA-1062 and the absence of additional antimicrobial preservatives, leading potentially to reduced microbial contamination and longer storage times for any given ALPHA-1062 composition.

Determination of a therapeutically effective amount and suitable mode of administration is within the capability of those skilled in the art, especially in light of the detailed disclosure provided herein. The amount of a composition administered will, of course, be dependent on the subject being treated, the severity of the affliction, the manner of administration, the judgment of the prescribing physician, etc.

The compositions may, if desired, be presented in a pack or dispenser device, such as an EMA and/or FDA approved kit, which may contain dosage forms containing the active ingredient. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labelling approved by the European Medicines Agency (EMA) and/or U.S. Food and Drug Administration (FDA) for prescription drugs or of an approved product insert.

Compositions including a compound of the present invention formulated in a compatible pharmaceutical carrier may also be prepared, placed in an appropriate container, and labelled for treatment of an indicated condition.

"Multi-use dispensers" are known to those skilled in the art and may come in the form of any device suitable for multiple doses or multiple applications of the compound. In other words, herein it is preferred that a multi-use device does not require opening or re-filling between multiple administration events and is typically stable, with sufficient API stability and low microbial loads, over extended periods. In some embodiments, the dispenser may be suitable for administration of any given liquid formulation, preferably a solution, although emulsions and suspensions, and the like, are contemplated.

"Liquid formulations" are known to the skilled person and are common in pediatric or geriatric patient populations. A liquid formulation typically requires a stable, dissolved, or suspended form of the compound that meets release, bioavailability, and taste/irritation requirements. Both immediate and sustained release liquid products are contemplated. Liquid formulation strategies typically include direct incorporation of an active drug or pro-drug in a dissolved or suspended or emulsified state. Alternative states include incorporation of an active drug or pro-drug in the form of a suspended drug-ion exchange resin complex, or incorporation of drug or pro-drug in the form of a dissolved or suspended drug-cyclodextrin inclusion complex, or in an emulsified state.

"Dispensers" configured for transmucosal administration are also known in the art, as are transmucosal administration routes, which relate preferably to oral, nasal, vaginal, and urethral modes. Mucosal membranes are relatively permeable, have a rich blood supply and hence allow the rapid uptake of a drug into systemic circulation to avoid first pass metabolism. The oral transmucosal delivery preferably relates to the buccal and sublingual routes. This route of drug delivery offers a number of benefits over other drug delivery approaches and allows drugs to circumvent some of the body's natural "defense mechanisms" like first pass metabolism, the harsh stomach environment, and potentially metabolism in the intestines due to exposure to microbial populations present in the intestines. By way of example, several approaches have been used like drug delivery through the nasal route by using sprays, pumps and gels while the mucoadhesive, quick dissolve tablets and solid lozenge formulations are suitable for the oral mucosal route, also, vaginal or urethral routes can be explored using mucoadhesive suppositories, in-situ gel and foam formulations.

Preferred dispensers or multi-use dose devices according to the invention relate to any of the above-mentioned multi-use devices. In some embodiments, the dispensers available for example from Nemera (La Verpillière, France) or Aptar Pharma (Illinois, USA) are preferred. For example, Nemera provides Advancia® nasal spray dispensers, which are high-performing pumps with excellent dose consistency and prime retention, anti-clogging actuators, no metal contacting the formulation and hygienic anti-actuation snap-on overcaps. As a further example, Aptar Pharma's nasal pump technology removes the need for drug manufacturers to add preservatives to nasal spray formulations. The Advanced Preservative Free (APF) systems use a tip-seal and filter technology to prevent contamination of the formulation. A spring-loaded tip seal mechanism is employed with a filter membrane in the ventilation channel. The Nemera and Aptar technology, amongst others, offers a number of benefits, such as a metal-free fluid path thereby preventing the oxidization of the formulation, a preservative-free system and therefore an anti-microbial dispenser employing a purely mechanical barrier.

According to Advancia (Nemera) technology, the intake of air into the dispenser takes place via a venting system with a silicone membrane. This technology, and technology similar thereto, has a continuous barrier of homogenous material which allows air to diffuse through the silicone, which acts as a permeable membrane. Consequently, the continuous barrier ensures the microbial integrity of the drug. The venting system filters the intake of air using a very fine membrane manufactured from silicone polymer. The silicone membrane is a solid, non-porous material. The membrane is homogenous and does not contain any holes. The membrane's intermolecular distance is of the order of nanometers-allowing the passage of air through the membrane but completely preventing the passage of any liquid or solid particle, including bacteria, due to the silicone membrane structure. The function of the silicone membrane can be compared to an inflated balloon. The balloon is a continuous, waterproof material yet gas slowly passes through the wall of the balloon until the pressures inside and outside reach equilibrium. Moreover, Advancia® PF offers a patented anti-clogging actuator in the upper part of the system, called closing tip. This mechanism ensures that no contamination can enter through the actuator orifice, which therefore provides protection from crystallization and clogging issues, and avoids evaporation to guarantee good prime retention.

Additional technology from Nemera is also contemplated, such as SP270+ and SP370+, which enable very good dose consistency, wide range of dose volumes: 50 μl to 200 μl with different actuators, various neck finishes: screw-on, snap-on and crimp-on, and are suitable for liquid solutions and suspensions. For unregulated markets alternative technology from Nemera is contemplated, such as SP27 and SP37. Alternatively, continuous valves for nasal and dermal delivery may be employed, such as Nemera solutions employing pressurized delivery with a neutral propellant agent (nitrogen) or liquid gases, such as CV20 for liquids, Valve 6668 for viscous products or Valve 6685 for powders. Additional Nemera dispensing devices are disclosed, for example, in U.S. Pat. No. 9,238,532, which discloses a tip for dispensing liquid for mounting on a container. A valve includes at least two elements that are mobile in relation to one another, each mobile element including a bearing zone against the other mobile element. One of the mobile elements bears anti-microbial material on or in the immediate proximity of a part of its bearing zone forming a blocking barrier and all surfaces of the dispensing tip in contact with the inside are free of anti-microbial material. As a further example, U.S. Pat. No. 9,345,616 discloses a liquid dispenser device with air intake that reliably guarantees the sterility of the content of a reservoir. The function of taking in air and blocking air-borne micro-organisms s performed, not by an air filter, but by using the gas diffusing properties of certain materials. Thus, a member of a type other than a filter is used, namely a member made of non-porous polymer material. Such a member presents the advantage of passing non-contaminated air in a manner that is more reliable than a filter, which is porous by definition. Other technologies are disclosed in US20150043958, U.S. Pat. Nos. 8,827,124, 8,986,266, and US20140231536A1. All cited patent documents are hereby incorporated in their entirety by reference. As further examples, Nemera provides various nasal administration technologies, such as advanced preservative free nasal pumps, classic technology platforms and VP3, VP6 and VP7 technologies.

As a further example, the nasal spray technology from Aptar provides excellent spray performance, is suitable for solutions, suspensions and viscous drug formulations including gels, is suitable for gamma-irradiation sterilization, and allows wide range of dose volumes from 45 µl to 1,000 µl, and offers a wide range of closures, actuators and accessories. As a further example, the CPS technology from Aptar is a highly versatile spray pump designed for the multi-dose delivery of preserved or non-preserved drug formulations for the nasal route. CPS can be used for a range of other applications which include intra-nasal vaccination. Various benefits include wide range of dose volumes: 50 µl to 140 µl, no re-priming needed even when not used regularly, can be sterilized by irradiation. The CPS systems use anti-clogging tip seal technology to minimize crystallization with high-viscosity and high-volatile formulations, proven CPS filter technology avoids entrance of contaminated air into the container, fully validated and tested microbiological integrity, no anti-microbial additives within the pump components, and metal-free fluid pathway components. For example, U.S. Pat. No. 9,095,864 from Aptar discloses a fluid dispenser unit and spray devices, in particular of the nasal type, and preferably applies to sprays incorporating a closure member for closing the dispenser orifice. The device mechanics disclosed therein relates to closing the dispenser orifice completely when the pump is not in use, wherein the closure member can come to co-operate directly with the dispenser orifice by being brought elastically by the return spring of the pump towards its closed position, thereby preventing any germs or bacteria penetrating inside the device between two actuations, and thereby significantly minimizing the risks of contaminating the composition to be dispensed. As another example, US20090294347 discloses a dispensing device for a liquid medium, having a medium reservoir for accommodating the medium, having a dispensing opening for dispensing the medium from the medium reservoir, and having a pressure-equalizing channel which opens out into the medium reservoir and has a microbiologically active filter arrangement inserted therein. All cited patent documents are hereby incorporated in their entirety by reference.

The compositions according to the invention may, if desired, be presented in a pack or dispenser device, such as an FDA approved kit, which may contain dosage forms containing the active ingredient. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert.

Compositions including a compound of the present invention formulated in a compatible pharmaceutical carrier may also be prepared, placed in an appropriate container, and labeled for treatment of an indicated condition.

Suitable conditions are brain injuries associated with neurological and/or cognitive impairment, preferably those disclosed herein, in particular TBI or other brain traumata or concussions.

FIGURES

The invention is further described by the figures. These are not intended to limit the scope of the invention.

SHORT DESCRIPTION OF THE FIGURES

FIG. 1: Location and effects of a controlled cortical impact (CCI) on the brain of rats.

Figure 2:
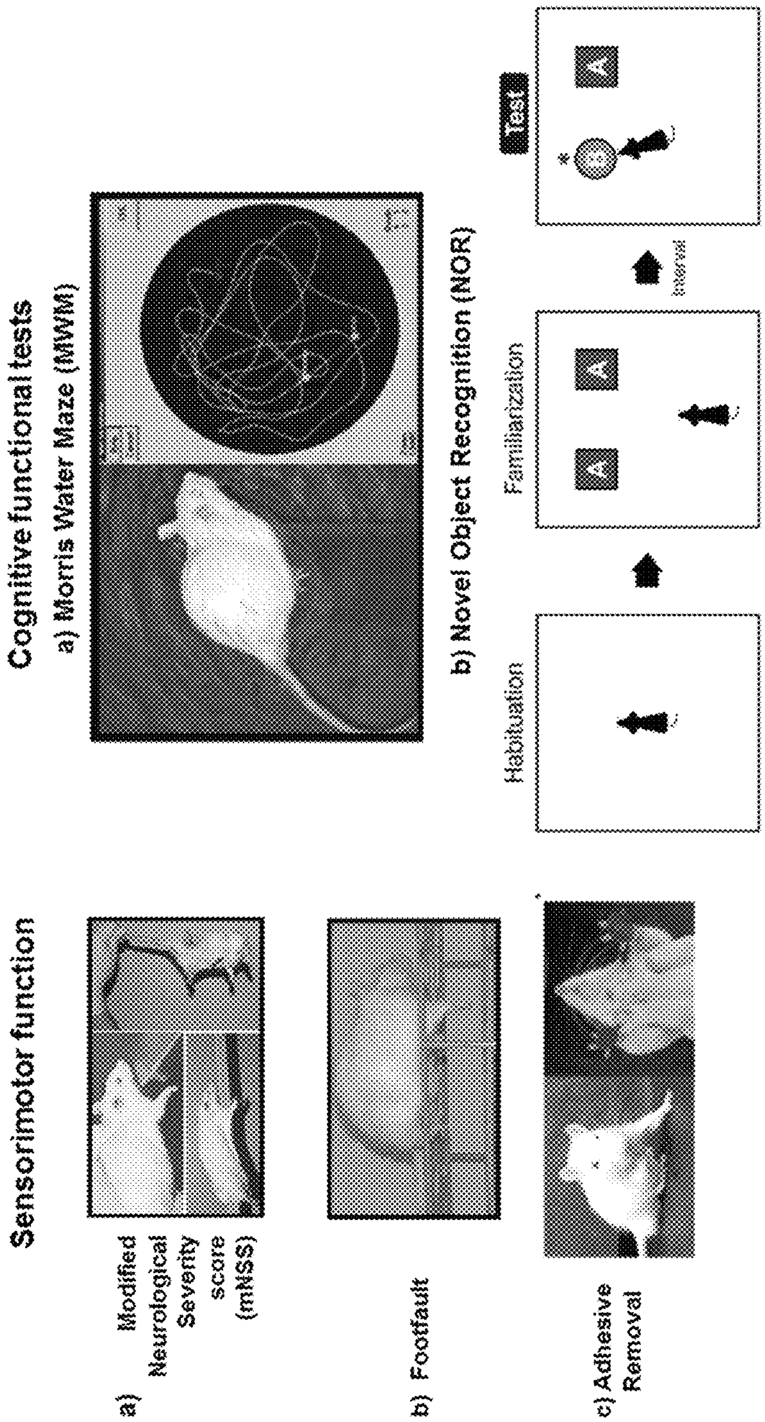

FIG. 2: Functional tests that are carried out on healthy, vehicle treated and ALPHA-1062 treated rats to assess sensorimotor and cognitive function after TBI.

Figure 3:
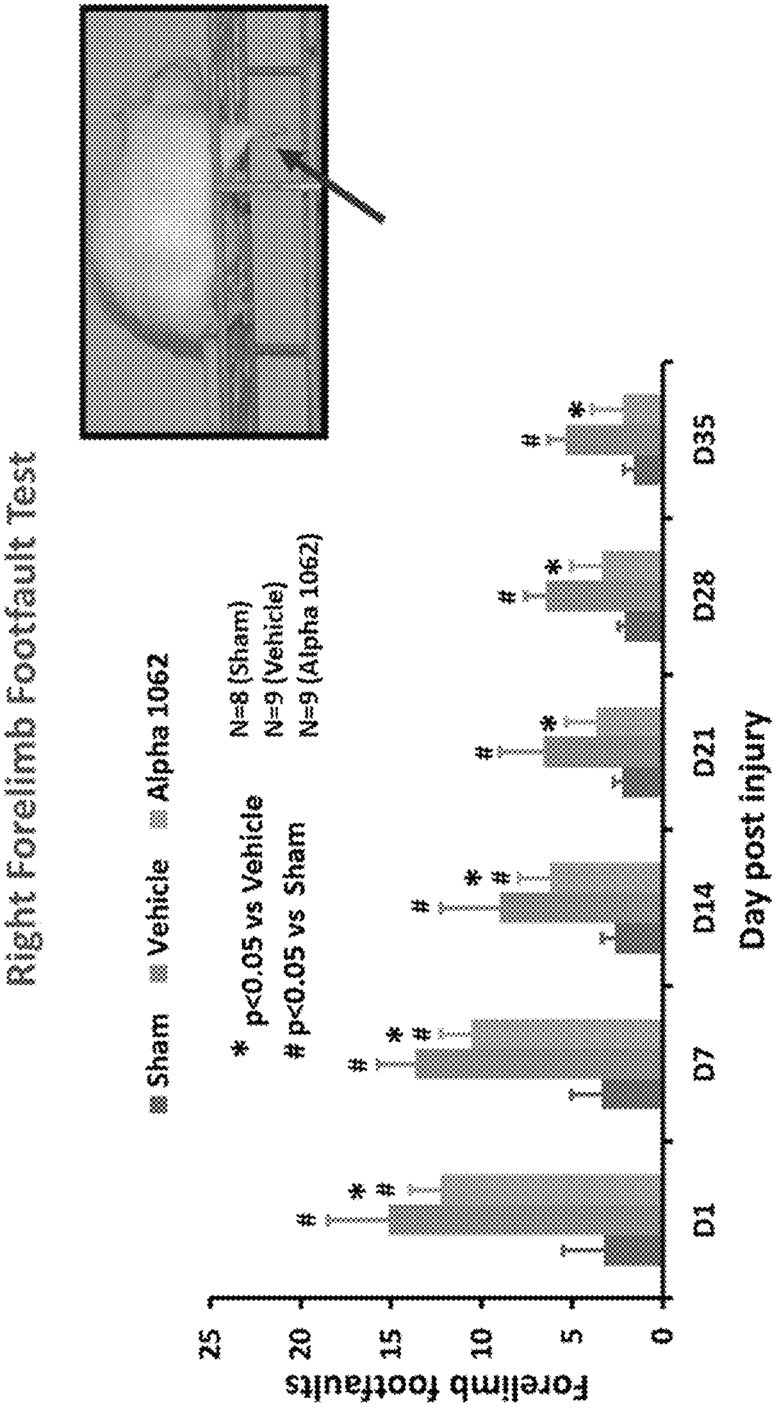

FIG. 3: Results of the sensorimotor function tests where events of the rat's right forelimb foot faults during the walk over a mesh were assessed.

Figure 4:
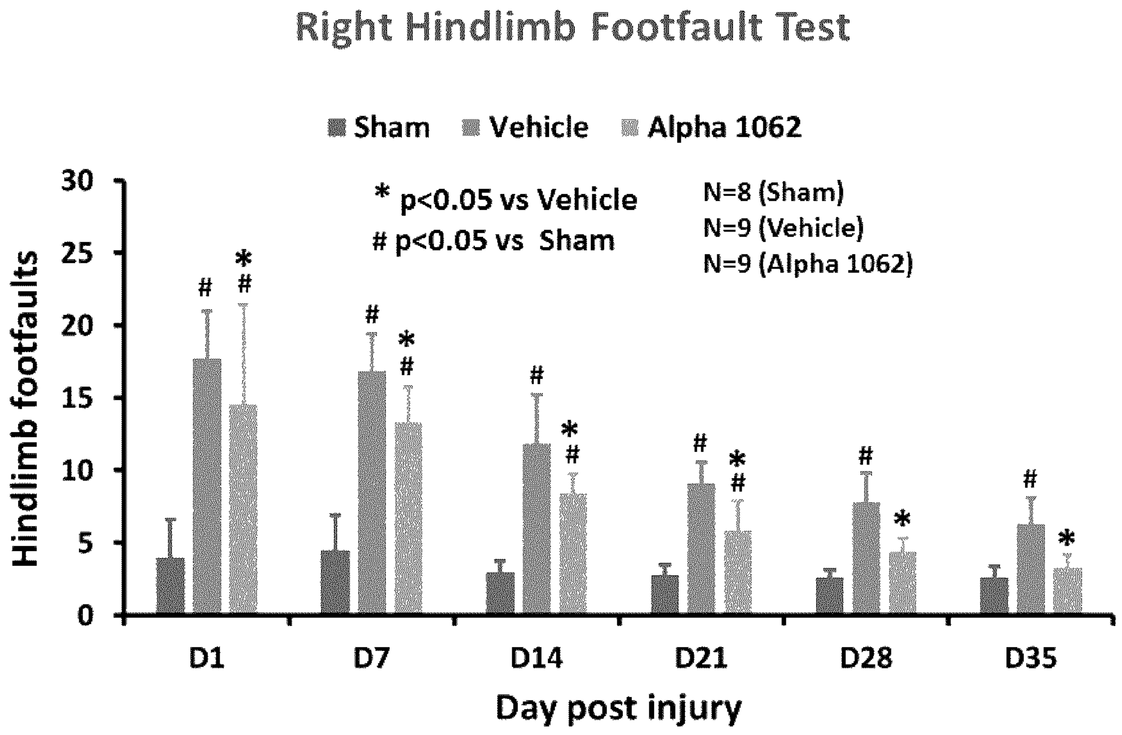

FIG. 4: Results of the sensorimotor function tests where events of the rat's right hindlimb foot faults during the walk over a mesh were assessed.

Figure 5:
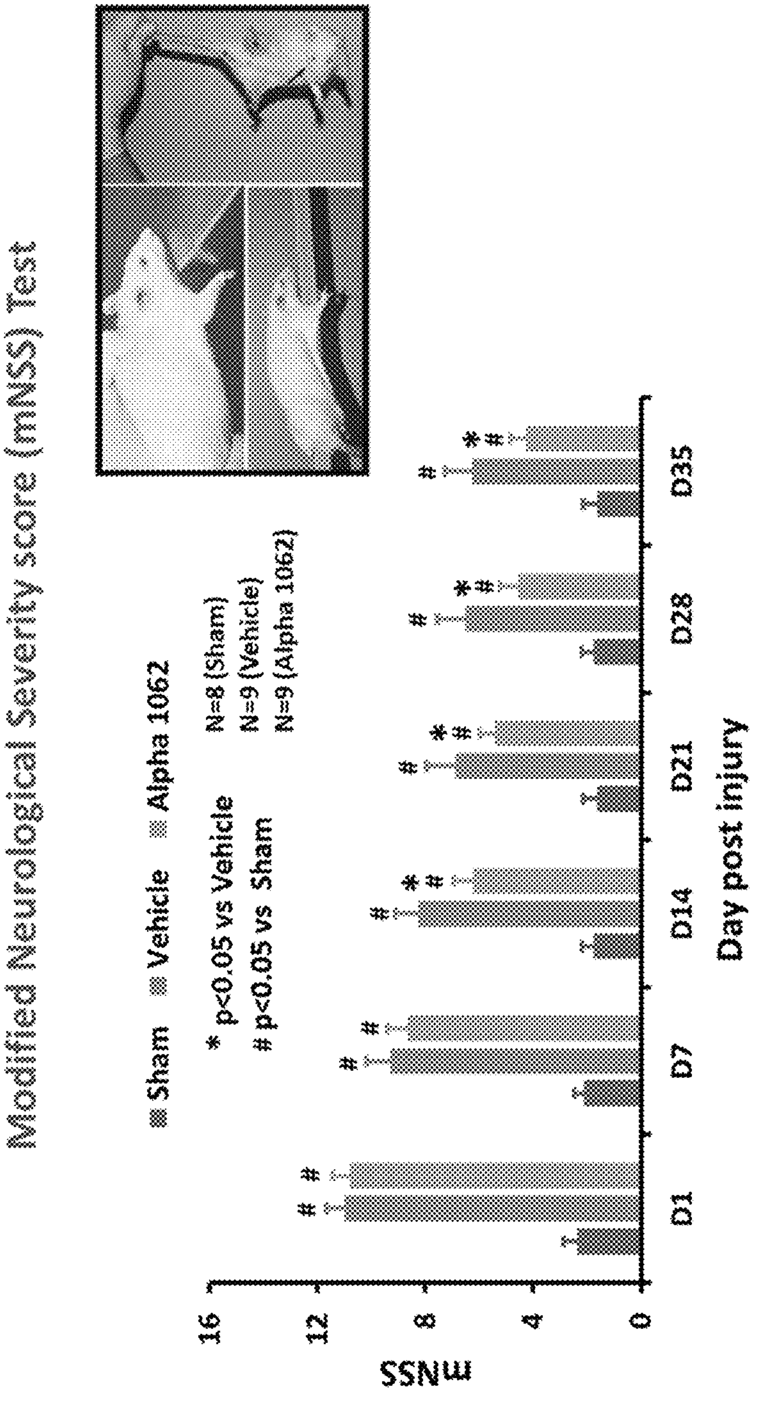

FIG. 5: Results of the sensorimotor tests depicting the results in the scaling of the modified neurological severity score (mNSS).

FIG. 6: Results of the adhesive removal test for the right forelimb.

Figure 7:
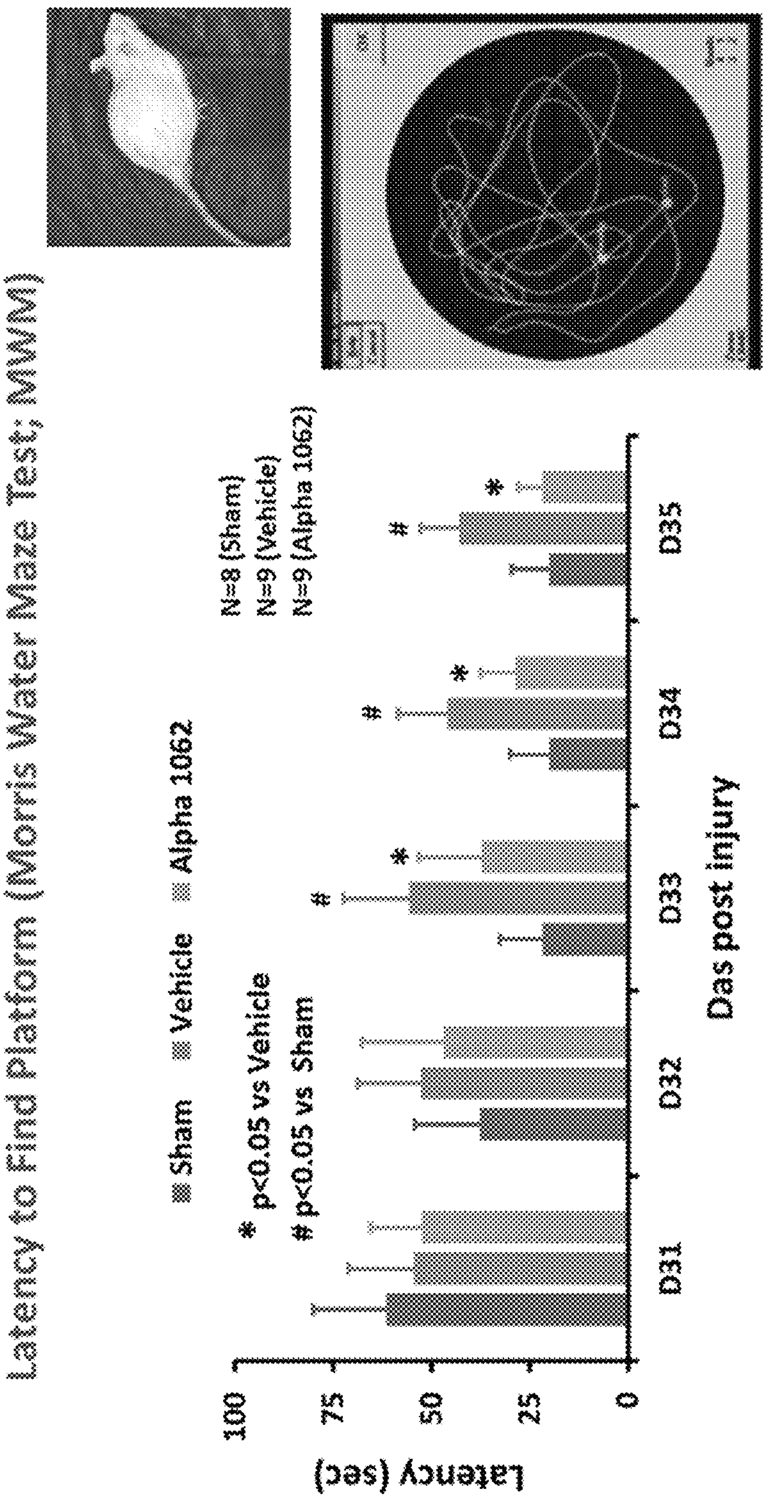

FIG. 7: Results of the Morris water maze test.

Figure 8:
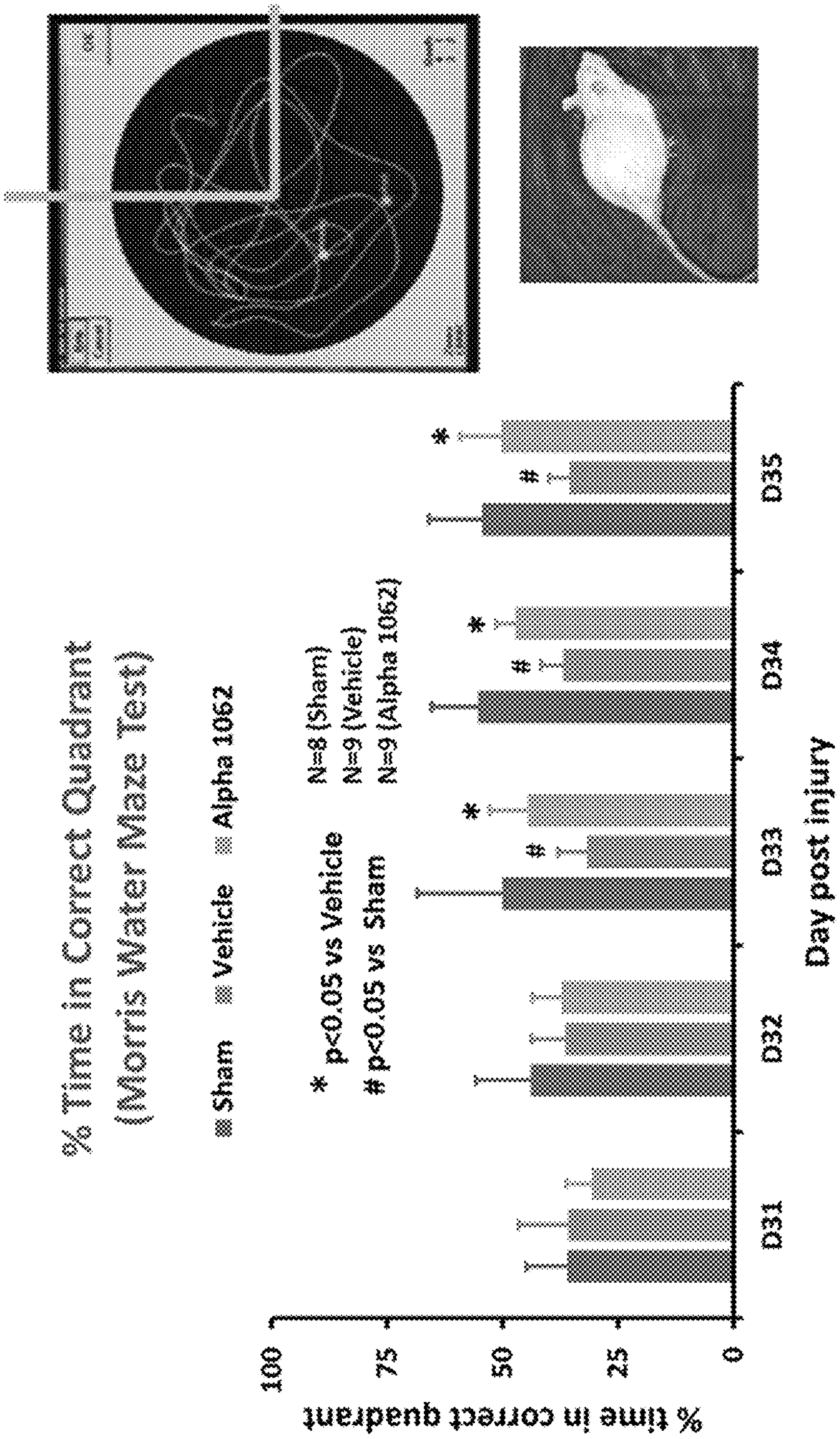

FIG. 8: Further results of the Morris water maze test.

Figure 9:
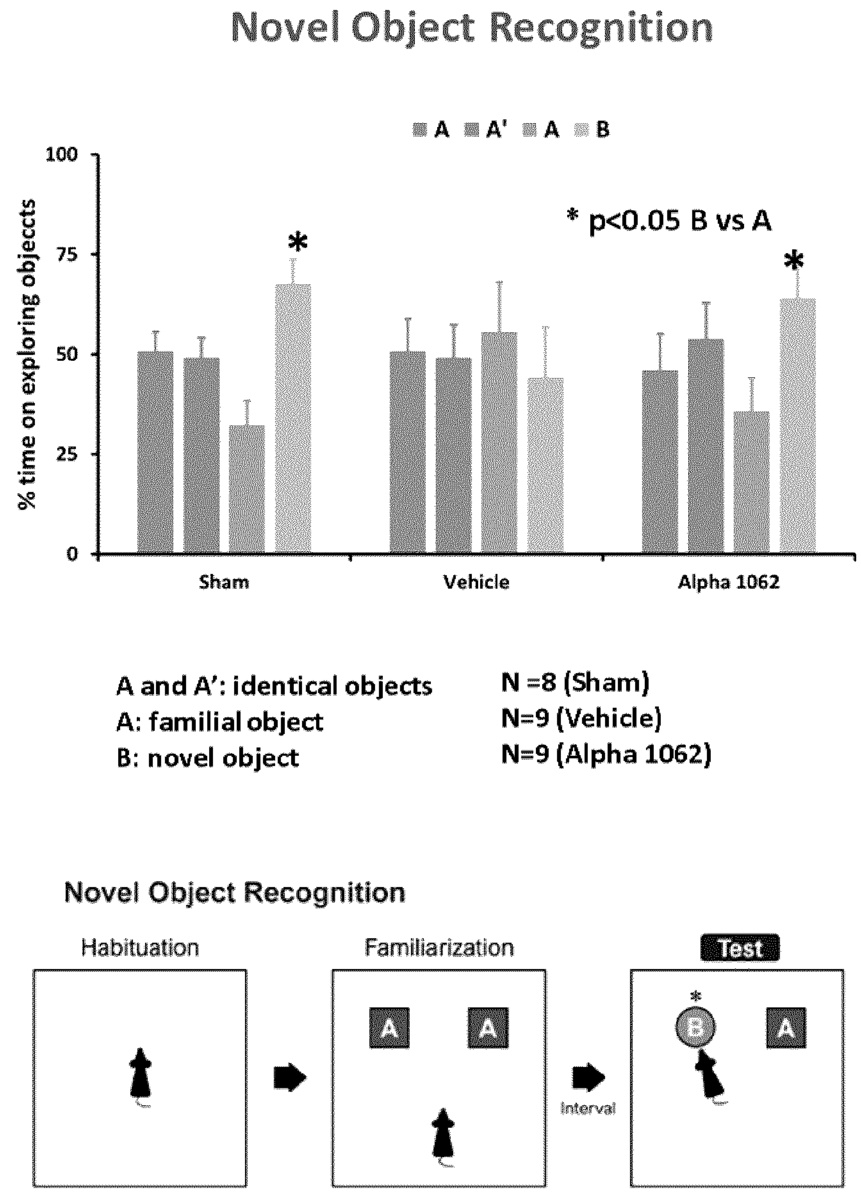

FIG. 9: Results of the new object recognition test.

Figure 10:
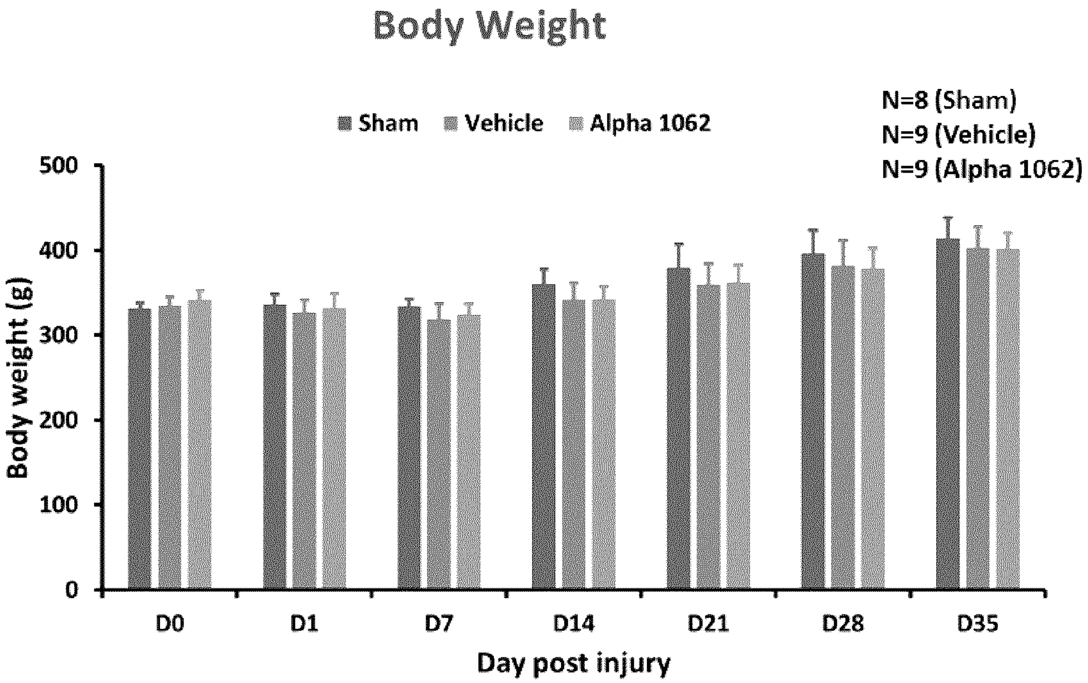

FIG. 10: Weight of the test animals throughout the study (day D0-D35).

Figure 11:
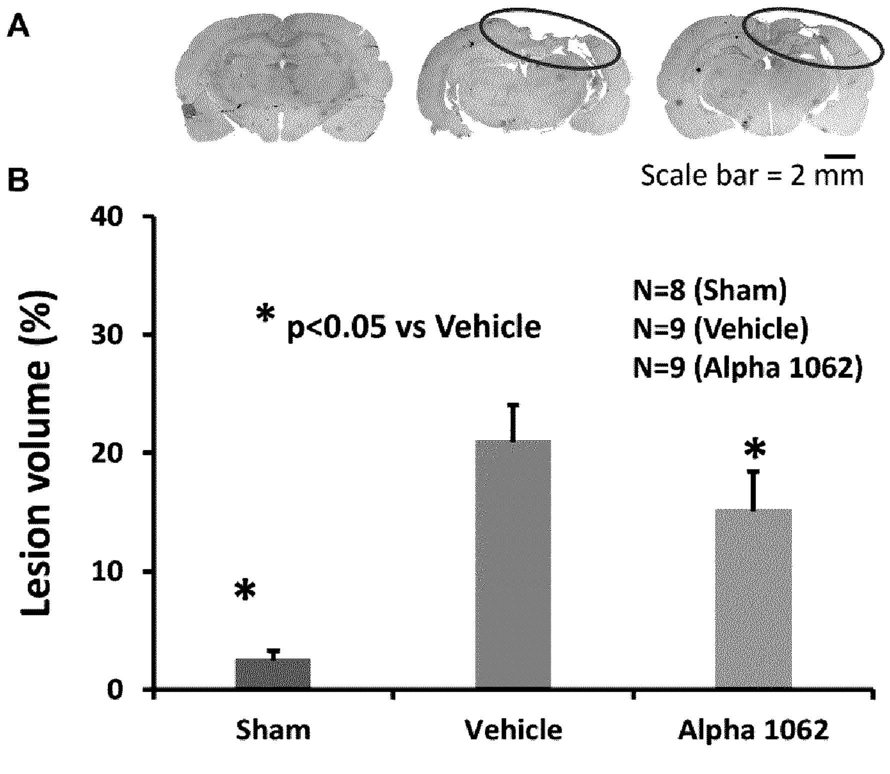

FIG. 11: ALPHA-1062 significantly reduces the lesion volume at 35 days post-TBI.

Figure 12:
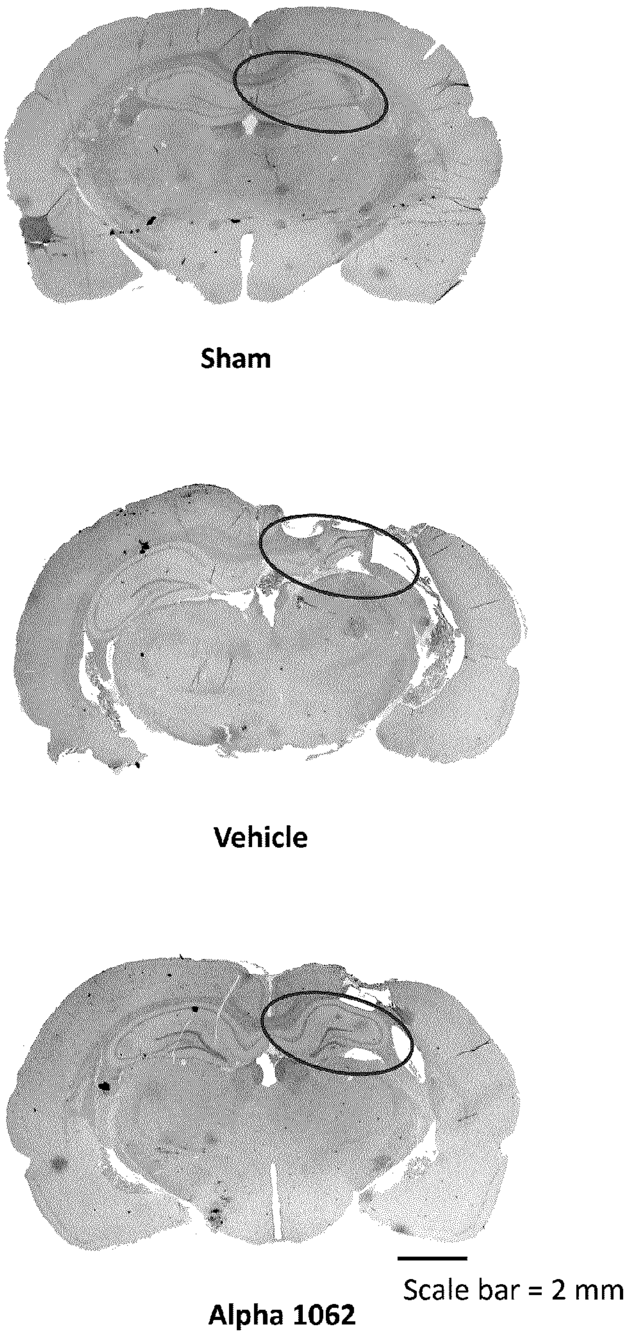

FIG. 12: ALPHA-1062 is neuroprotective and maintains hippocampal structure at 35 days post-TBI.

Figure 13:
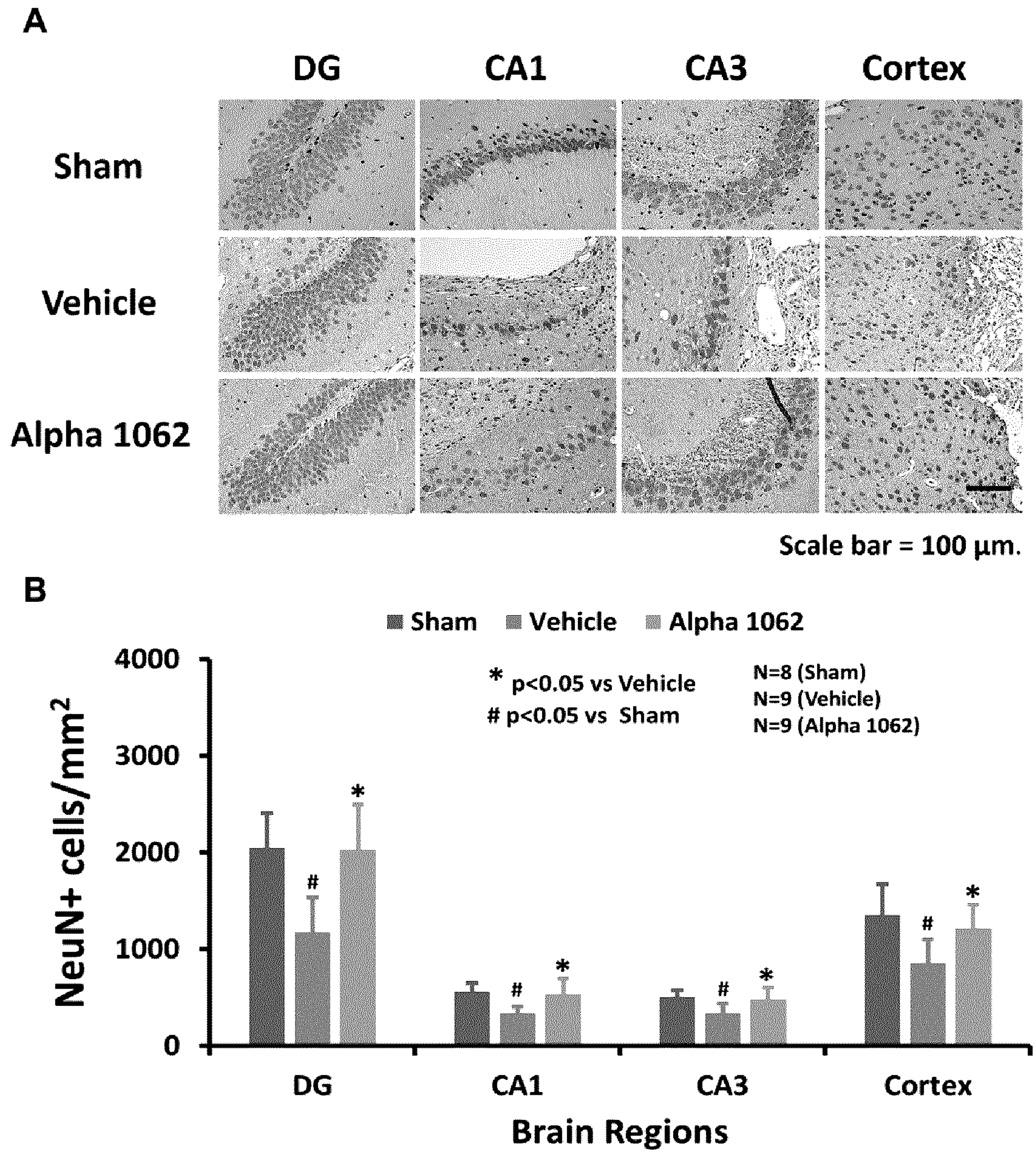

FIG. 13: ALPHA-1062 is neuroprotective and significantly reduces neuronal cell loss: NeuN positive cells quantitated at 35 days post TBI.

Figure 14:
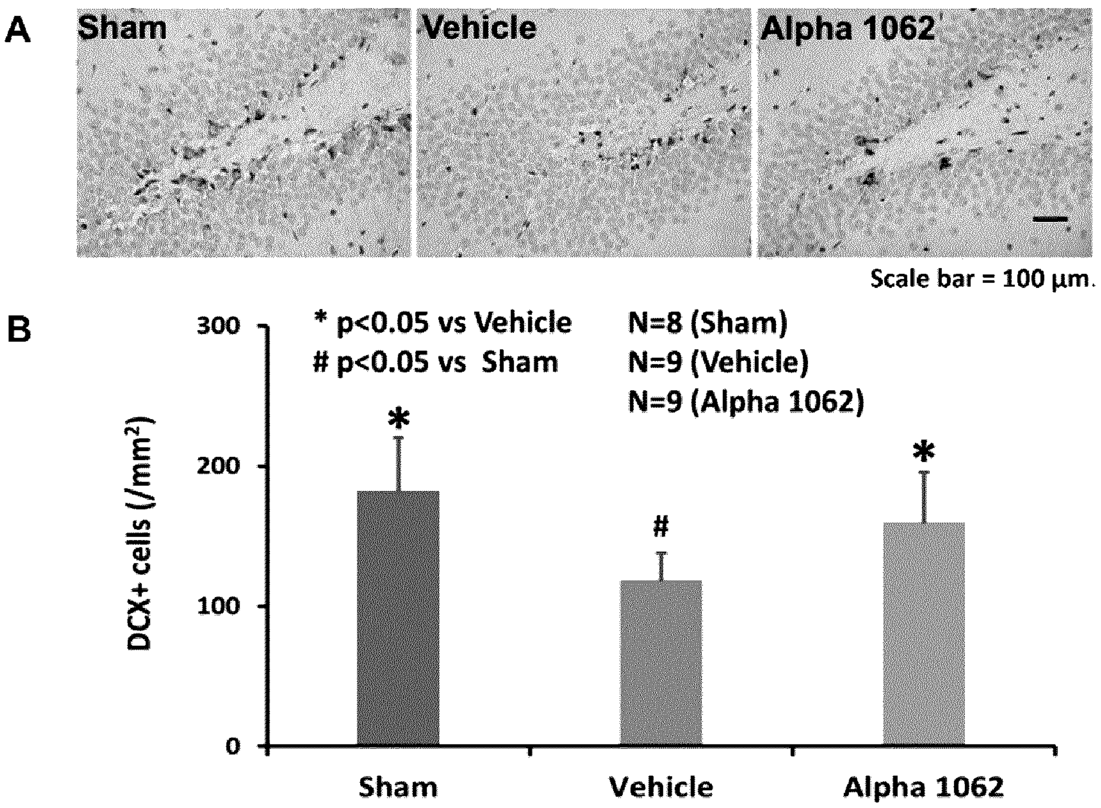

FIG. 14: ALPHA-1062 significantly enhances dcx+ neuroblasts in the dentate gyrus of the hippocampus (35 days after a TBI event).

Figure 15:
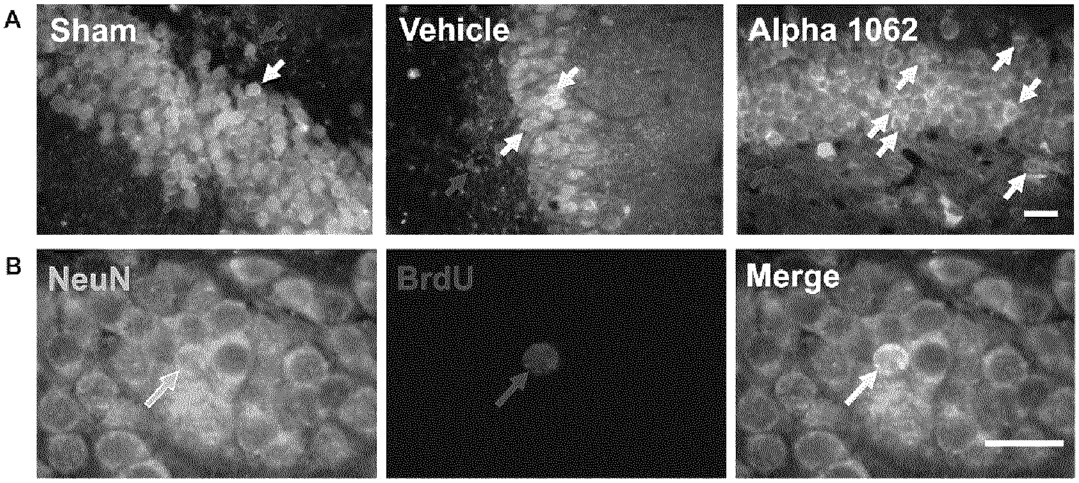

FIG. 15: ALPHA-1062 enhances neurogenesis in the dentate gyrus of the hippocampus-IHC (35 days post TBI).

Figure 16:
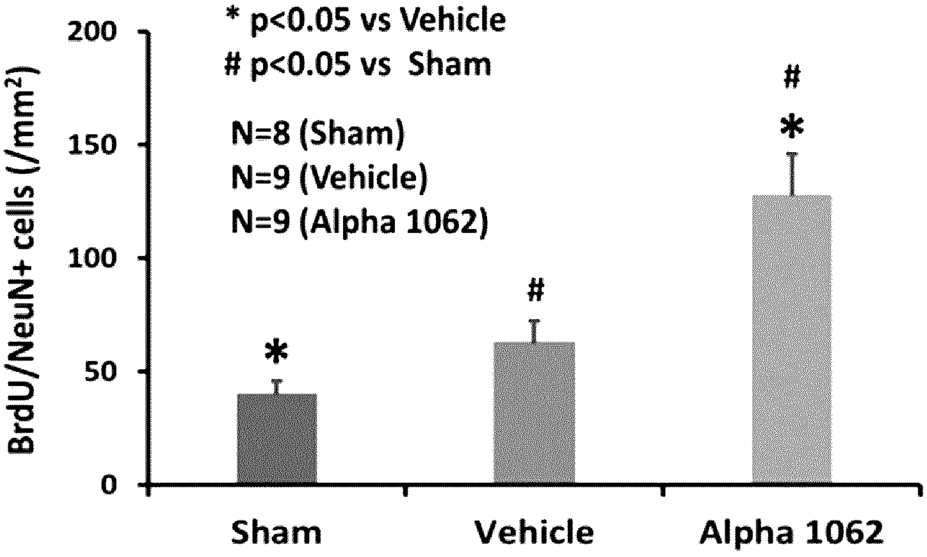

FIG. 16: ALPHA-1062 enhances neurogenesis in the dentate gyrus of the hippocampus-cell counts (35 days post TBI).

Figure 17:
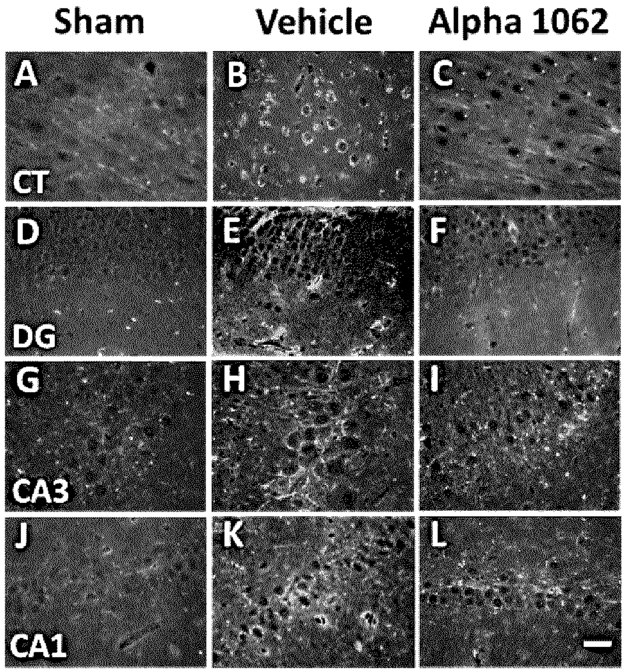
Figure 17:
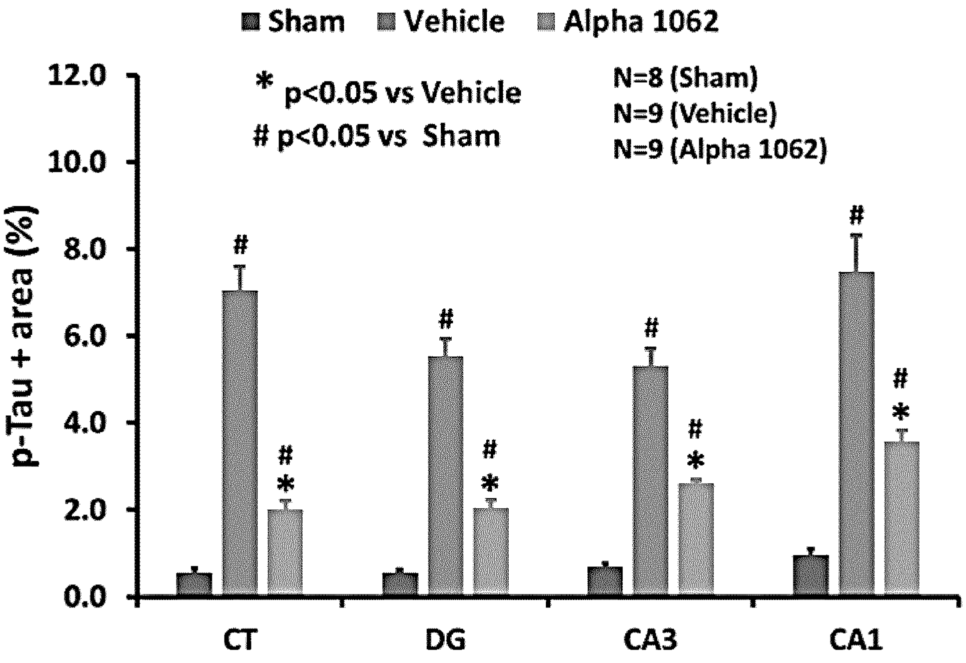

FIG. 17: ALPHA-1062 significantly reduces p-Tau protein (35 days post TBI).

Figure 18:
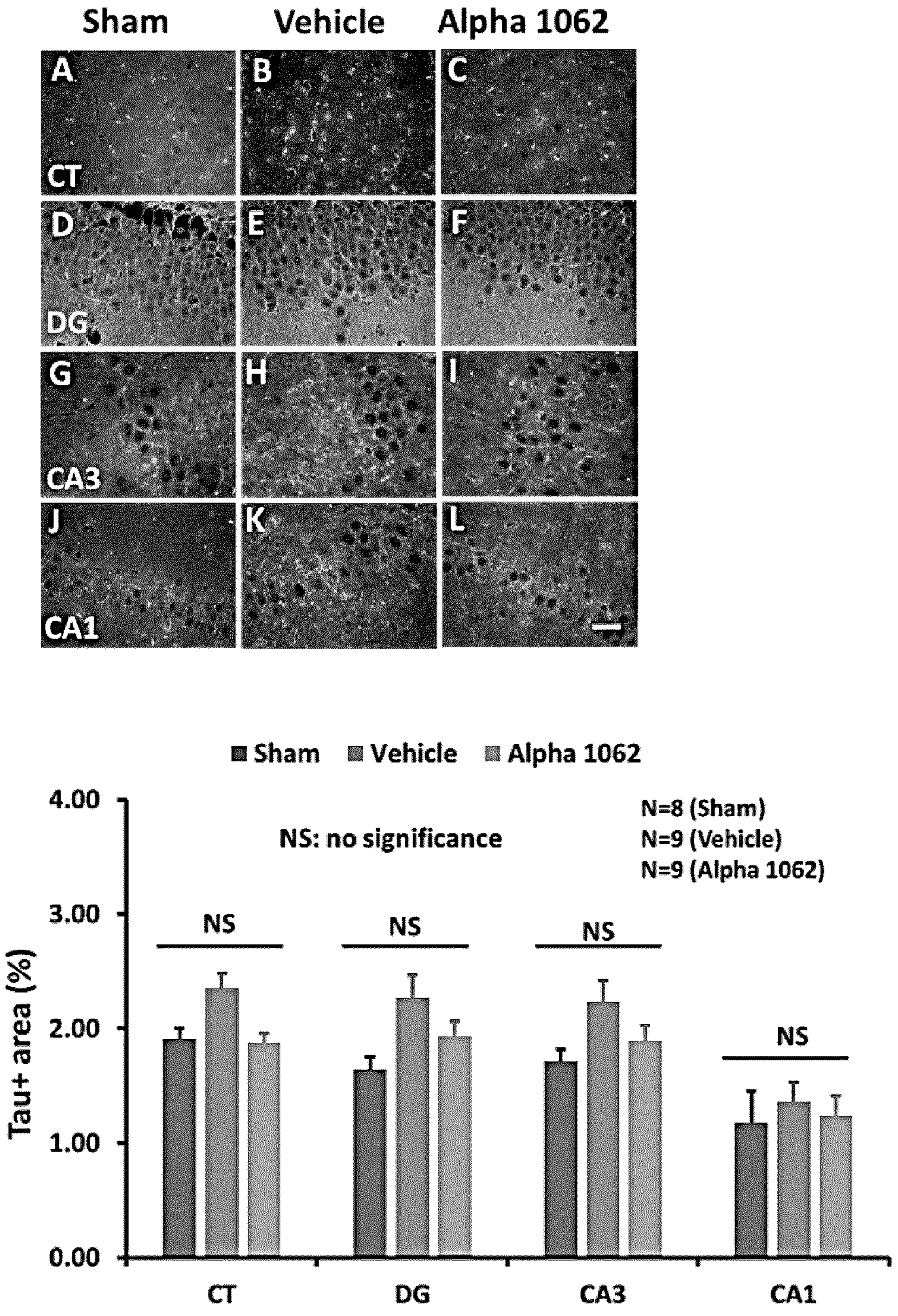

FIG. 18: ALPHA-1062 does not alter total Tau protein (35 days post TBI).

DETAILED DESCRIPTION OF THE FIGURES

FIG. 1: The figure illustrates the location and effects of a controlled cortical impact (CCI) on the brain of rats, which are alive but anesthetized during the intervention. This experiment serves as a simulation of TBI and its effects on the brain. A) Anatomy scheme illustrating a rat skull bone structure and the injury that was induced in the left parietal cortex to simulate a moderate TBI in a rat (red circle). B) Distribution of the strain caused by the impact of an object on the rat brain, depicted in fringe levels. C) Pathologic overview of the damage caused by an TBI on a rat brain. D) The photograph on the top shows a healthy rat brain (sham surgery). The photograph on the bottom illustrates the size and location of the injury that was induced in the left parietal cortex of a rat's brain to simulate TBI, wherein the rat was sacrificed 7 days after the TBI. E) Haematoxylin and eosin staining of slices of a healthy rat brain (top row) and slices of a rat's brain (bottom row) 7 days after an TBI simulating injury (controlled cortical impact CCI) was induced.

FIG. 2: The figure illustrates functional tests that are carried out on healthy (sham surgery) no treatment, vehicle treated and ALPHA-1062 treated rats to assess sensorimotor and cognitive function after TBI. Sensimotor function tests. a) The figure depicts tests to assess the modified neurological severity score (mNSS). B) The figure shows a test used for assessing the "foot fault" of an animal. The animal is required to balance over a grid and the frequency of steps missing the grid are counted. This test assesses the functionality of the injured parietal cortex of the rat's brain. c) The adhesive removal test consists of applying adhesive tape on each forepaw of the animal and measuring the time-to-contact and the time-to-remove them. This behavior requires correct paw and mouth sensitivity (time-to-contact) and correct dexterity (time-to-remove). Cognitive function tests: a) This picture illustrates the Morris water maze that comprises that a rat is placed in a large circular pool (picture on the left) and is required to find an invisible platform that allows it to escape the water by using various visuo-spatial cues. This test is used to study spatial learning and memory and assesses hippocampal and select cortical brain region function. Usually, the path of the rat through the pool is tracked (picture on the right) and the time spend in the proximity of the platform as well as the time needed until the platform is found by the rat are measured. b) For the new/novel object recognition (NOR) test, after a habituation time in the test space (picture on far left) rats are given the opportunity to explore two identical objects (A) for a predetermined period of time (picture in the middle). After a delay, the animals are then presented with two objects to explore, one of which is the same as in the first exploration trial (A), the other a new object (B) (picture on the right). Depending on the length of the delay between the two trials or depending on the extend of cortical damage, the rats will either explore the novel object for a greater time period, indicating memory for the familiar object, or will explore the novel and familiar objects for the same amount of time, indicating a lack of recall or loss of memory for the familiar object presented during the initial trial.

FIG. 3: The graph shows the results of the sensorimotor function tests where misstep events of the rat's right forelimb foot faults during the walk over a mesh were assessed. The tests were performed as described in Example 1, wherein rats received either, no TBI and no treatment, vehicle treatment or ALPHA-1062 treatment after a TBI event. The graph shows that animals treated with ALPHA-1062 after experiencing TBI exhibited significantly fewer foot faults than animals that received vehicle treatment after TBI. This indicates a significant acute preservation of and persistently improved rate and extent of recovery of locomotor skills in rats that were treated with ALPHA-1062 after a TBI event, in comparison to rats that received only vehicle treatment following TBI. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 4: The graph shows the results of the sensorimotor function tests where misstep events of the rat's right hindlimb foot faults during the walk over a mesh were assessed. The tests were performed as described in Example 1, wherein rats received either sham surgery and no treatment, vehicle treatment or ALPHA-1062 treatment after a TBI event. The graph shows that animals treated with ALPHA-1062 after experiencing TBI exhibited significantly fewer foot faults than animals that received vehicle treatment after TBI. This indicates a significant acute preservation of locomotor skill and persistently improved rate and extent of locomotor skills in rats that were treated with ALPHA-1062 after a TBI event in comparison to rats that received only vehicle treatment. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 5: The graph shows the results of the sensorimotor tests and depicts the results in the scaling of the modified neurological severity score (mNSS). The tests were performed as described in Example 1, wherein rats received either no TBI and no treatment, vehicle treatment or ALPHA-1062 treatment after a TBI event. From day 14 (D14) onwards, the ALPHA-1062 treated animals performed statistically significantly better than vehicle treated animals. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 6: The graph shows the results of the adhesive removal test for the right forelimb. The tests were performed as described in Example 1, wherein rats received either no TBI and no treatment, vehicle treatment or ALPHA-1062 treatment after a TBI event. The graph shows that animals that received ALPHA-1062 after the TBI event performed from day 7 (D7) on significantly better than the vehicle treated animals. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 7: The graph shows the results of the Morris water maze test. The tests were performed as described in Example 1, wherein rats received either no TBI and no treatment, vehicle treatment or ALPHA-1062 treatment after a TBI event. The graph shows that animals that received ALPHA-1062 after a TBI performed from day 33 (D33, the first day of assessment), and onward significantly better than the vehicle treated animals. From day 34 on The ALPHA-1062 treated rats found the submerged platform as well as the healthy (sham surgery) animals. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 8: The graph shows the results of the Morris water maze test, wherein the time spent in the correct quadrant (green line), the quadrant of the pool comprising the platform, was measured. The tests were performed as described in Example 1, wherein rats received either no TBI and no treatment, vehicle treatment or ALPHA-1062 treatment after a TBI event. The graph shows that animals that received ALPHA-1062 following TBI performed from day 33 (D33) onward significantly better than the vehicle treated animals. From days 33 on the ALPHA-1062 treated animals spend an equivalent amount of time in the correct quadrant as the healthy (sham) animals. Both groups performed statistical significantly better than the vehicle treated animals who failed to show any preference for the correct quadrant. The left bars represent the healthy sham rats that experienced no TBI. Middle bars represent rats that experienced TBI and were subsequently treated with vehicle control treatment. Right bars represent the rats that were treated with ALPHA-1062 after experiencing TBI. The detailed treatment regimen and experimental setup can also be found in Example 1. The sham group comprised 8 rats, the vehicle and ALPHA-1062 treatment groups comprised each 9 rats.

FIG. 9: The graph (top panel) shows the results of the novel object recognition test. A schematic overview of the test is depicted on the bottom of the figure. Briefly, after habituation to the test room animals were confronted with two identical objects (A; left bars, and A'; center-left bars) where they became “familiar” with these objects. The same animals were later exposed to two objects (A=same as before; right bars, and B*=a novel/different object; yellow bars). Rats are naturally inquisitive and will, when healthy, spend more time exploring the new object (B*). Cognitively impaired animals fail to demonstrate this preference. Both ALPHA-1062 treated animals (bars on the right side of the graph) and the healthy animals (sham surgery; bars on the left of graph) demonstrated a statistically significant preference for the novel object. In contrast, the TBI animals that received only vehicle treatment (bars in the middle of the graph), failed to demonstrate any preference for the novel object. The detailed treatment regimen and experimental setup can also be found in Example 1. The sham group comprised 8 rats, the vehicle and ALPHA-1062 treatment groups comprised each 9 rats.

FIG. 10: The graph shows the weight of the test animals throughout the study (day D0-D35). There was no significant difference in body weight among the three treatment groups at each time point during the study ($p>0.05$). The group of untreated animals (sham surgery) shows from D20-35 vs D0 a significant body weight gain (within the group $p<0.05$). The group of TBI vehicle treated animals shows from D1-6 compared to D0 a significant body weight loss and from D28-35 compared to D0 a significant body weight gain (within the group $p<0.05$). The group of ALPHA-1062 treated animals shows from D1-7 compared to D0 a significant body weight loss and from D29-35 compared to D0 a significant body weight gain (within the group $p<0.05$). The detailed treatment regimen and experimental setup can also be found in Example 1. The sham group comprised 8 rats, the vehicle and ALPHA-1062 treatment groups comprised each 9 rats.

FIG. 11: ALPHA-1062 treatment significantly reduces the lesion volume at 35 days post-TBI. Panel A: Coronal sections of rat brains from healthy sham surgery animals (left image) or subjected to TBI and vehicle treated (middle image) or ALPHA-1062 treated (right image). The TBI-associated lesions are indicated by a circle, the scale bar represents the length of 2 mm. Panel B: The graph depicts the lesion volume in percent of brain volume. The ALPHA-1062 treated animals (bar on the right) showed a significant ($p<0.05$) reduction of lesion volume compared to the vehicle treated mice (middle bar) at 35 days following TBI.

FIG. 12: ALPHA-1062 is neuroprotective and maintains hippocampal structure at 35 days post-TBI. The hippocampal region is indicated by a circle. The same coronal sections shown in FIG. 11A are depicted at higher magnification, to demonstrate the ALPHA-1062 enabled preservation of the hippocampus on the injured side of the brain (circles). The scale bar represents the length of 2 mm.

FIG. 13: ALPHA-1062 is neuroprotective and significantly reduces neuronal cell loss at 35 days following TBI. Results are shown for tissues treated with anti-NeuN immunohistochemistry (IHC) to quantitate neuronal cell numbers. NeuN, which is also known as the mRNA splicing regulator Fox-3, is predominantly found in the nucleus of mature neurons. Panel A: coronal images of brain regions with IHC with for NeuN protein (Fox-3) 35 days following TBI or from healthy animals (sham surgery). The images depict the hippocampal regions DG, CA1, CA3 and cortex (left to right columns respectively) for either sham animals (healthy, untreated), or rats that suffered a TBI and were treated with either vehicle or ALPHA-1062 (top to bottom rows respectively) f. Panel B: depicts the quantification of NeuN positive cells/mm2 for each of said brain regions. Animals treated with ALPHA-1062 (bars on the right) following TBI showed comparable neuronal cell numbers to healthy sham surgery animals (bars on the left), whereas vehicle treated animals (bars in the middle) suffered significant ($p<0.05$) neuronal cell loss post TBI when compared to either sham animals (#) or ALPHA-1062 treated animals (*).

FIG. 14: ALPHA 1062 significantly enhances DCX+ (doublecortin positive) neuroblasts in the dentate gyrus of the hippocampus (35 days following TBI). Doublecortin (DCX) is a endogenous marker of adult neurogenesis. Panel A: The Figure shows the iIHC of dentate gyrus sections of untreated sham surgery animals (left image) or of animals 35 day following TBI, which were treated with either vehicle (middle image) or ALPHA-1062 (right image). ALPHA-1062 treated animals demonstrate a higher number of DCX positive stained cells compared to vehicle treated animals, indicative of increased cytogenesis. ALPHA-1062 treatment resulted in a comparable number of DCX positive cells to to that observed in sham surgery animals. Panel B: The quantitation of DCX positive cells per square millimetre of DG from either sham surgery animals, or from animals 35 days following TBI, treated t with either vehicle (middle bar) or ALPHA-1062 (right bar) . . . . A significantly higher number of DCX positive cells were present in ALPHA-1062 treated animals compared to vehicle treated animals (*) and a significantly reduced number of DCX positive cells were present in vehicle treated animals compared to healthy sham surgery animals (#).

FIG. 15: ALPHA-1062 enhances neurogenesis in the dentate gyrus of the hippocampus (35 days following TBI). Panels A: Depict representative images of double label IHC detection of NeuN and BrdU to detect mitotic cells (dark grey arrows) in tissue samples from the dentate gyrus of untreated sham surgery animals, or animals treated with either vehicle or ALPHA-1062 for 35 days following TBI (top panels from left to right). ALPHA-1062 treated animals (right image) exhibit higher numbers of NeuN and BrdU (double) positive neurons (light grey arrows, merge) compared to vehicle treated animals (centre picture). Panels B:

The bottom panels depict the DG from an ALPHA-1062 treated animal 35 days after TBI, with double labelling (merge; light grey arrow) of a mature granule cell neuron for both NeuN and BrdU, BrdU labeling indicates the cell was generated from a cycling stem cell population in the days following TBI.

FIG. 16: ALPHA 1062 treatment following TBI enhances neurogenesis in the dentate gyrus of the hippocampus Quantitation of double positive IHC for NeuN and BrdU: untreated sham surgery animals (left bar), or animals treated with either vehicle (middle bar) or ALPHA-1062 (right bar) for 35 days following TBI (of the experiment shown in FIG. 15). The number of new granule cell neurons was significantly increased ($p<0.05$) in animals treated with ALPHA-1062 in comparison to both, vehicle (*) treated and healthy sham surgery (#) animals. This observation is indicative of increased neurogenesis providing improved tissue recovery following TBI when ALPHA-1062 treatment is administered.

FIG. 17: ALPHA 1062 treatment significantly reduces pathological p-Tau accumulation (35 days post TBI). The upper panel shows brain sections from sham surgery, ALPHA-1062, or vehicle-treated animals labelled with an antibody against p-Tau. p-Tau immunoreactive areas including cortex (CT), dentate gyrus (DG), CA3 and CA1 regions of the hippocampus of the ipsilateral hemisphere were imaged and quantified by Image J software (NIH). The lower panel shows quantification of the IHC intensity. Sham surgery animals (left bars) show relatively low levels of p-Tau, whereas TBI animals treated with vehicle (control) (central bars) show high levels of p-Tau. TBI animals treated with ALPHA-1062 (right bars) show significantly reduced levels of p-Tau compared to vehicle controls. Numbers of animals in each group are shown.

FIG. 18: ALPHA 1062 treatment does not alter total Tau protein (35 days post TBI). The upper panel shows brain sections from untreated sham surgery, ALPHA-1062 treated or vehicle-treated animals labelled with an antibody against total Tau. Tau immunoreactivity in cortex (CT), dentate gyrus (DG), CA3 and CA1 regions of the hippocampus of the ipsilateral hemisphere were imaged and quantified by Image J software (NIH). The lower panel demonstrates quantitation of the signals obtained. No significant differences in levels of total Tau were observed between any of the groups of animals. Numbers of animals in each group are shown.

EXAMPLES

The invention is further described by the following examples. The examples are intended to further describe the invention by way of practical example and do not represent a limiting description of the invention.

Example 1: Evaluating Efficacy of ALPHA-1062 in Rats Following Traumatic Brain Injury In the present example the efficacy and use of the substances and pharmaceutical compositions according to one embodiment of the invention was performed in an exemplary 35-day study in a controlled cortical impact injury model. The aim of this study was to determine the efficacy of ALPHA-1062 (galantamine benzoate gluconate salt) on functional and histological outcomes in young adult male rats after moderate traumatic brain injury (TBI) induced by controlled cortical impact (CCI).

SUMMARY

As compared to the Vehicle (purified water) treatment control, ALPHA-1062 treatment initiated 2 h post injury (4.5 mg/kg IN), twice daily (6 h interval) for 35 days:

1) Significantly improved motor sensory functional recovery measured by foot-fault, adhesive removal and mNSS tests.
2) Significantly improved cognitive functional recovery measured by NOR and MWM tests at 5 weeks after injury.
3) Did not significantly alter the body weight over the 35-day study (no evidence of overt toxicity).
4) Significantly reduced the lesion size measured at 35 days after injury.
5) Significantly reduced the neuronal cell loss in the cortex and hippocampus of ipsilateral side.
6) Significantly enhanced neurogenesis including augmentation of DCX+ neuroblasts and BrdU/NeuN+new neurons in the DG.
7) Significantly reduced pathological p-Tau accumulation in the injured cortex and hippocampus at 35 days after injury, suggesting that ALPHA-1062 reduces neurodegeneration in rats after moderate TBI induced by CCI.

Acute IN administration (2 hr post injury) with twice daily treatment of ALPHA 1062 provides neuroprotection, reduces pathological p-Tau accumulation, and stimulates neurogenesis as well as significantly improves sensorimotor and cognitive functional recovery in a rat contusion model of TBI compared to the Vehicle treatment. These data suggest that ALPHA 1062 has potential as a treatment for TBI.

Methods:

Young adult (2-3 months) male Wistar rats were subjected to a moderate traumatic brain injury (TBI) induced by controlled cortical impact (CCI). Animal models of TBI including the CCI model and functional tests have been described in detail in peer reviewed publications (Xiong et al., 2013, Nat Rev Neurosci.; Zhang et al., 2016, J Neurosurg.; Zhang et al., 2016, Neurochem Int.; Zhang et al., 2021, J Neurotrauma). Injury consisted of a single impact at 4.0 m/sec, 2.5 mm deformation to the left parietal cortex. In addition, a group of animals was left healthy/not injured to serve as a healthy control.

The animals were divided into 3 groups:

1) TBI+Vehicle (purified water, n=10)
2) TBI+ALPHA-1062 (4.5 mg/kg) (n=10)
3) Healthy/not injured and not treated (Sham surgery) (n=10)

To have 8 rats per study group, 10 rats (8/0.8=10) were included considering a 20% mortality. The total number of male rats used as planned were 30 male rats.

The substance used in this study was ALPHA-1062 at 4.5 mg/kg. As control treatment (vehicle) purified water was administered intranasally (IN). The ALPHA-1062 and the control treatment were initiated 2 hours after injury and continued twice daily (with a 6-hour interval) for 35 consecutive days.

In addition to the ALPHA-1062 or vehicle control treatment, 1 day post injury Bromodeoxyuridine (BrdU) was administrated at 100 mg/kg via Intraperitoneal injection for 7 consecutive days, to enable the monitoring of cell proliferation. Bromodeoxyuridine (BrdU) is a thymidine analog that is incorporated into the DNA of dividing cells during the S-phase of the cell cycle.

Data were evaluated for normality applying the following statistical analyses: Data transformation was considered if the data was abnormal. The data was analyzed with GraphPad Prism Software 9.0. All data herein is presented as the mean±standard deviation (SD) and were analyzed with one-way analysis of variance (ANOVA) or two-way ANOVA (treatment×time) followed by post hoc Tukey's multiple comparison test (more than two groups). Differences between means are considered statistically significant when p is <0.05.

During the in vivo part of the study cognitive functional tests were performed by conducting Morris water maze (MWM) tests and novel object recognition tests on all animals at 5 weeks after TBI, with the MWM test being performed on days 31-35 following TBI (see Table 1).

In addition, neurological functional tests were performed by conducting footfault tests and observations to determine the modified neurological severity score (mNSS) at 1, 7, 14, 21, 28, 35 days after TBI (see Table 1). The mNSS is a composite score assessing motor, sensory, balance, and reflex functions. Details of the tests and scoring system can be found in Table 2.

TABLE 1

Tests performed at the primary endpoint of the study.

| | Test/Day post TBI (moderate) | | | | | |
|---|---|---|---|---|---|---|
| | 1 d | 7 d | 14 d | 21 d | 28 d | 31-35 d |
| Motor (Behavior: mNSS, footfault) | x | x | x | x | x | x |
| Spatial Cognition (MWM) | | | | | | x |
| Novel Object Recognition (NOR) | | | | | | x |

mNSS: modified neurological severity score; MWM: Morris water maze; Experiments were performed in a blinded study regarding the treatment groups.

The Morris water maze (MWM) is a test used in behavioral neuroscience to study spatial learning and memory, for example in rats. It enables spatial learning and memory to be studied, and can also be used to assess damage to hippocampus and select cortical regions of the brain. The MWM can be used to assess the effect of lesions to the brain in areas concerned with memory, cognitive function and spatial learning. In the Morris water maze test a rat, for example, is placed in a circular pool and is required to find an invisible, submerged platform that allows it to rest and leave the water. Usually, the rat is tracked while swimming in the pool and parameters, such as the time spend swimming in the quadrant of the pool comprising the platform or the time spend swimming in proximity to the platform and the total time spend until finding the platform (escape latency) are measured.

In the adhesive removal test, an adhesive tape is applied to the right forepaw of an animal. Both the time-to-contact the adhesive (sensory perception), as well as the time-to-remove the adhesive (locomotor skill) are assessed by this test.

The rat novel/new object recognition (NOR) assay is a relatively high-throughput, robust, and sensitive procedure for evaluating compounds for cognition-enhancing activity. For the test, rats are given the opportunity to explore two identical objects for a predetermined period of time. After a delay, the animals are then presented with two objects to explore, one of which is the same as in the first exploration trial, the other a new object. Depending on brain functionality, the rats will either explore the novel object for a greater time period, indicating memory for the familiar object, or will explore the novel and familiar objects for the same amount of time, indicating a lack of recall or loss of memory for the familiar object presented during the initial trial.

The modified neurological severity score (mNSS) is a rating scale for neurological functionality and includes a composite of motor (muscle status and abnormal movement), sensory (visual, tactile and proprioceptive), reflex and balance tests. The test is used to assess neurologic deficits and the grade of neurologic damage on the aspects of motor, ground walking, sensory, coordination of movements, reflex, and abnormal movements. It is usually performed with rodents, e.g. rats and the testers are blind to the treatment groups. Four aspects are observed, including abnormal movements or absence of reflex, beam balance test, sensory function, and locomotor function. The baseline for the normal animals is 0 points.

*A score value of 1 was given for the inability to perform a test, or for the lack of a tested reflex, or for abnormal movement.

TABLE 2

Modified Neurological Severity Score (mNSS): Tests & Scoring Values.

| | |
|---|---|
| **Motor test score values and descriptions (Normal score = 0; maximum possible summary score = 6)** | |
| 0 or 1* | Flexion of forelimb after raising rat by the tail |
| 0 or 1* | Flexion of hindlimb after raising rat by the tail |
| 0 or 1* | Head moved >10° to vertical axis within 30 seconds after raising rat by the tail |
| 0 | Normal walk after placing rat on the floor |
| 1 | Inability to walk straight after placing rat on the floor |
| 2 | Circling toward paretic side after placing rat on the floor |
| 3 | Falls down to paretic side after placing rat on the floor |
| **Sensory test score values and descriptions (Normal score = 0; maximum possible summary score = 2)** | |
| 0 or 1* | Placing test (visual and tactile test) |
| 0 or 1* | Procioceptive test (deep sensation, pushingpaw against table to stimulate limb muscles) |
| **Beam and balance test score values and descriptions (Normal score = 0; maximum possible summary score = 6)** | |
| 0 | Balances with steady posture |
| 1 | Grasps side of beam |
| 2 | Hugs beam and 1 limb falls down from beam |
| 3 | Hugs beam and 2 limbs fall down from beam, or spins on beam (60 seconds) |
| 4 | Attempts to balance on beam, but falls off (>40 seconds) |
| *Score value | of 1 was given for the inability to perform a test, or for the lack of a tested reflex, |
| 5 or for abnormal | Attempts to balance on beam, but falls off (>20 seconds) movement. |
| 6 | Falls off; no attempt to balance or hang on to beam (<20 seconds) |
| **Reflex absence and abnormal movements test score values and descriptions (Normal score = 0; maximum possible summary score = 4)** | |
| 0 or 1* | Pinna reflex (head shakes when auditory meatus is touched with cotton) |
| 0 or 1* | Corneal reflex (eye blink when cornea is lightly touched with cotton) |
| 0 or 1* | Startle reflex (motor response to a brief noise from snapping a clipboard paper) |
| 0 or 1* | Seizure, myoclonus, myodystony |

*A score value of 1 was given for the inability to perform a test, or for the lack of a tested reflex, or for abnormal movement.

Histological assessment was performed including quantitative image analysis protocols; followed by statistical analysis of the data. Histology: All rats were sacrificed after the last Morris water maze (MWM) test 35 days after TBI for the following histological analyses: lesion volume (H&E), neuronal cell loss in injured cortex and hippocampus (NeuN), doublecortin (DCX, neuroblasts), NeuN/BrdU (newborn neurons), pathological p-Tau (AT8) and total Tau IHC.

For tissue preparation rats were anesthetized and perfused trans-cardially with saline solution, followed by 4% paraformaldehyde in 0.1 M PBS, pH 7.4. Rat brains were removed and immersed in 4% paraformaldehyde for 2-4 days. Using a rat brain matrix (Activational Systems Inc.), each forebrain was cut into 2-mm thick coronal blocks for a total 7 blocks from bregma 5.2 mm to bregma −8.8 mm per animal. The tissues were embedded in paraffin and a series of 6 μm-thick slides were cut.

For immunohistochemistry (IHC) antigen retrieval procedure was performed by boiling sections in 10 mM citrate buffer (pH 6.0) for 10 minutes. After washing with PBS, sections were incubated with 0.3% H2O2 in PBS for 10 minutes, blocked with 1% BSA containing 0.3% Triton-X 100 at room temperature for 1 hour, and incubated with mouse anti-doublecortin antibody (1:200; DCX, Santa Cruz Biotechnology, Santa Cruz, CA), and monoclonal mouse anti-NeuN antibody (1:400; Chemicon, Millipore) at 4° C. overnight. For negative controls, primary antibodies were omitted. After washing, sections were incubated with biotinylated anti-mouse antibodies (1:200; Vector Laboratories, Inc.) at room temperature for 30 minutes. After an additional washing, sections were incubated with an avidin-biotin-peroxidase system (ABC kit, Vector Laboratories, Inc.), visualized with diaminobenzidine (Sigma), and counterstained with hematoxylin (Results are shown, for example, in FIGS. 13 and 14).

For immunofluorescent staining (e.g. results are shown in FIGS. 15 and 16) the brain sections, after being deparaffinized and rehydrated, were boiled in 10 mM citric acid buffer (pH 6) for 10 minutes. After washing with PBS, sections were incubated in 2.4 N HCl at 37° C. for 20 minutes. Sections were incubated with 1% BSA containing 0.3% Triton-X-100 in PBS. Sections were then incubated with mouse antibody against BrdU (1:200) at 4° C. overnight. For negative controls, primary antibodies were omitted. Cy3-conjugated anti-mouse antibody (1:400; Jackson ImmunoResearch, West Grove, PA) was added to sections at room temperature for 2 hours. Each of the steps was followed by three 5-minute rinses in PBS. Then, the sections were incubated with different rabbit antibodies against NeuN (1:200), and after washing, incubated with FITC-conjugated goat anti-rabbit antibody at room temperature for 2 hours. Tissue sections were mounted with Vectashield mounting medium (Vector laboratories, Burlingame, CA).

Immunofluorescent staining for Tau and p-Tau (results shown in FIGS. 17 and 18) was carried out as follows: After being deparaffinized and rehydrated, brain sections were boiled in 10 mM citric acid buffer (pH 6) for 10 minutes. After washing with PBS, sections were incubated with 1% BSA in PBS. Sections were then incubated with chicken antibody against total TAU (1:100, Aves) or mouse anti-p-Tau (1:500, at Ser202/Thr205 Fisher, MN1020, AT8) at 4° C. overnight. After washing, sections were incubated with FITC-conjugated goat anti-chicken or mouse secondary antibody (1:400, Jackson ImmunoResearch Inc) at room temperature for 2 hours. After washing, sections were stained with DAPI for 2 min (1:10,000), and rinsed with water for 5 min. Tissue sections were mounted with Vectashield mounting medium (Vector laboratories, Burlingame, CA).

For cell counting and quantitation NeuN+ cells were examined in the ipsilateral cortex, DG, CA1, and CA3 regions of the ipsilateral hippocampus. For analysis of neurogenesis, neuroblasts were defined by DCX+ cells. The number of DCX+ cells were examined within the granule cell layer of DG of the ipsilateral hippocampus. The newly generated neurons were identified by cells with co-localization of NeuN and BrdU immunoreactivities. We focused on the DG and its subregions, including the subgranular zone, granular cell layer, and the molecular layer. The number of BrdU+ cells (red-fluorophore) and NeuN (green-fluorophore)/BrdU-colabeled cells (yellow after merge) were counted. The fields of interest were digitized under the light microscope (Nikon, Eclipse 80i) at a magnification of either 200 or 400 using a CoolSNAP color camera (Photometrics) interfaced with MetaMorph image analysis system (Molecular Devices). The immune-positive cells were determined and divided by the measured areas and presented as numbers per square mm. Cell counting was performed by observers blinded to the individual treatment status of the animals. Tau or p-Tau immunoreactive areas including cortex, dentate gyrus, CA3 and CA1 regions of the ipsilateral hemisphere were imaged and quantified by Image J software (NIH).

In view of statistical analysis all data are presented as the mean±standard deviation (SD) and were evaluated for normality. Data transformation would be considered if data were abnormal. Data were analyzed with GraphPad Prism Software 9.0 with one-way analysis of variance (ANOVA) or two-way ANOVA (treatment×time) followed by post hoc Tukey's multiple comparison test (more than two groups). Differences between means were considered statistically significant when p was $<0.05$.

Results

ALPHA-1062 Administration Acutely Preserves and Persistently Improves Recovery of Locomotor Skills in Fore- and Hindlimb Foot-Fault Test Animals were monitored as they walked across a mesh for the number of times their right forelimb "missed" proper placement, indicating reduced locomotor skill. This is indicative of trauma in the left side of the brain. The results are depicted in FIG. 3. The tests were also carried out for the right hindlimb (FIG. 4).

ALPHA-1062 treatment (FIG. 3 and FIG. 4, gray bars) resulted in a statistically significant preservation of locomotor skill from the first day of treatment- and persistently statistically significantly improved recovery throughout the study, compared to the vehicle treated animals (FIG. 3 and FIG. 4, middle bars). By day 28 (D28) the performance of the ALPHA-1062 treated animals was statistically indistinguishable from that of the uninjured (sham) animals (FIG. 3 and FIG. 4, right vs. left bars). The acute preservation of locomotor skill suggests that the early administration of ALPHA-1062 post TBI, likely reduced the extent of the brain injury. Vehicle treated animals (FIG. 3 and FIG. 4, middle bars) show the inherent levels of functional recovery after TBI.

ALPHA-1062 Administration Improves Outcomes in the Modified Neurological Severity Score (mNSS)

The mNSS is a composite score assessing motor, sensory, balance, and reflex functions (details of the tests and scoring system are found in Table 2). From day 14 (D14) of recovery onwards, ALPHA-1062 treated animals performed statistically significantly better (FIG. 5, right bars) than vehicle treated animals (FIG. 5, middle bars), wherein this effect persisted throughout the duration of the study in comparison to vehicle treated animals.

ALPHA-1062 Administration Improves Motor Skill in the Right Forelimb Adhesive Removal Test The results of the adhesive removal tests are shown in FIG. 6. Starting on day 7 (D7) of recovery, and throughout the remainder of the study, ALPHA-1062 treated animals (FIG. 6, right bars) performed this motor skill as well as the uninjured (sham) animals (FIG. 6, left bars).

ALPHA-1062 Administration Improves Spatial Learning and Memory in MWM Test

The impact of ALPHA-1062 treatment after TBI was assessed using the Morris water maze (MWM). The Morris water maze is a test of spatial learning for rodents that relies on distal cues to navigate from start locations around the perimeter of an open swimming arena to locate a submerged escape platform. Spatial learning is assessed across repeated trials and reference memory is determined by preference for the platform area ("correct quadrant") when the platform is absent. FIG. 7 depicts the result of the final testing day of the MWM tests in which the rats swam in a pool of water and the latency (time from start to goal=platform) to find the platform was assessed. On days 33 to 35 of (D33-D35) testing the ALPHA-1062 treated animals (FIG. 7, right bars) were able to find a hidden escape platform as well as the uninjured (sham) animals (FIG. 7, left bars). Both groups performed statistically significantly better than the vehicle treated animals (middle bars).

In addition, the percentage of the time (% time) the rats spend in the "correct" quadrant of the pool, namely the quadrant where the platform was submerged in previous sessions, was also assessed. The results can be found in FIG. 8. On days 33 to 35 of testing the ALPHA-1062 treated animals (FIG. 8, right bars) spent an equivalent amount of time in the correct quadrant (enclosed by the green lines) as the uninjured (sham surgery) animals (FIG. 8, left bars). Both groups performed statistically significantly better than the vehicle treated animals (FIG. 8, middle bars), who failed to show any preference for the correct quadrant throughout the test.

ALPHA-1062 Administration Enables Cognitive Functional Recovery Post TBI

Object recognition tests were performed to assess the recovery of cognitive function after TBI. The test workflow is depicted at the bottom of FIG. 9, the results, namely the percentage of time spend exploring each object, are depicted at the top of FIG. 9. Animals were placed in a room with two identical objects (A (left bars in top graph of FIG. 9) & A' (middle bars) where they became "familiar" with these objects. The same animals were later exposed to two objects (A=same as before (right bars) and B=a novel/different object (yellow bars)). Rats are naturally inquisitive and will, when healthy, spend more time exploring the new object (B), which would be represented in the graph of FIG. 9 by a high value for B (rights bars shown at top graph of FIG. 9). Cognitively impaired animals fail to demonstrate this preference, as they do not remember the known object. Hence, a cognitive impairment could be assumed if a rat spends the same time exploring known and new objects. Both ALPHA-1062 treated animals (FIG. 9, bars on right side of top graph) and the uninjured animals (FIG. 9, bars on left side) demonstrated a statistically significant preference for the novel object (B). In contrast, the injured animals that received only vehicle treatment (FIG. 9, bars in the middle), failed to demonstrate any preference for the novel object.

TABLE 3

Summary of the performance of ALPHA-1062 treatment after TBI in functional motor, sensory and cognitive tests in comparison to either vehicle treatment or healthy sham animals.

| | TEST | over VEHICLE | over SHAM |
|---|---|---|---|
| Cognitive Functional Tests | Morris Water Maze (MWM) | superior | equivalent to |
| | Novel Object Recognition | superior | equivalent to |
| Motor and Sensory | Modified Neurological Severity Score (mNSS) | superior | |
| Functional Recovery | Footfault | superior | equivalent to |
| | Adhesive Removal | superior | equivalent to |

ALPHA-1062 Administration does not Alter Body Weight-No Overt Toxicity

As can be derived from FIG. 10, rats treated with ALPHA-1062 (FIG. 10, right bars) experienced no significant alterations in body weight compared to vehicle treated or untreated animals (FIG. 10, middle and left bars; no significant difference (P>0.05) in body weight among the 3 groups were detected at each time point). Only when compared to day zero of their own treatment group vehicle and ALPHA-1062 treated animals showed a significant weight loss in the first week of treatment. Vehicle treated animals showed in comparison to day zero (D0) on days 1-6 (D1-6) significant body weight loss (p<0.05) but from days 28-35 (D28-35) a significant gain of body weight in comparison to day zero (p<0.05). ALPHA-1062 treated animals showed in comparison to day zero (D0) on days 1-7 (D1-7) a significant body weight loss (p<0.05) but from days 29-35 (D29-35) a significant body weight gain in comparison to day zero. Untreated (sham) animals showed in comparison to their weight on day zero (D0) a significant (P<0.05) body weight gain between days 20-35 (D20-35) compared to day zero (D0).

Accordingly, ALPHA-1062 administration did not show overt toxicity in treated animals when compared to vehicle animals.

ALPHA-1062 Significantly Reduces the Lesion Volume at 35 Days Post-TBI.

Following sacrifice at 35 days after TBI, and quantitation of tissue loss, ALPHA-1062 treated animals showed a significant (p<0.05) reduction of lesion volume compared to the vehicle treated mice (see also FIG. 11). As shown in FIG. 12 in detail, ALPHA-1062-treatment enabled the preservation of hippocampal structure on the injured side of the brain. Hence it can be concluded that ALPHA-1062-treatment shows neuroprotective effects and leads to the maintenance of brain structure at 35 days after TBI.

ALPHA 1062 is Neuroprotective and Significantly Reduces Neuronal Cell Loss.

IHC with anti-NeuN antibodies to quantitate the numbers of neurons. revealed that ALPHA-1062 treatment reduced loss of neurons in the analyzed brain regions DG, CA1, CA3 and cortex at 35 days following TBI when compared to animals that were treated with vehicle. Importantly, ALPHA-1062 treatment resulted in neuronal cell numbers that did not differ significantly from sham surgery animals. Vehicle treated animals, however, suffered significant (p<0.05) neuronal cell loss post TBI when compared to either sham animals or ALPHA-1062 treated animals (see also FIG. 13).

ALPHA 1062 Significantly Enhances Doublecortin Positive Neuroblasts in the Dentate Gyrus of the Hippocampus.

IHC for doublecortin (DCX), an endogenous marker of adult neurogenesis, demonstrated that ALPHA-1062 treated animals exhibited a higher number of DCX positive cells when compared to samples from vehicle treated animals and comparable numbers to the sham surgery cohort of animals. Vehicle treated animals subjected to TBI showed a significantly reduced number of DCX positive cells when compared to sham surgery animals (see also FIG. 14). Hence it can be concluded that ALPHA-1062 treated animals showed increased cell renewal when assessed at 35 days following TBI.

ALPHA-1062 Enhances Neurogenesis in the Dentate Gyrus of the Hippocampus.

In addition, double label IHC for NeuN and BrdU was performed to detect mature, newly born granule neurons. ALPHA-1062 treated animals exhibited significantly higher ($p<0.05$) numbers of NeuN and BrdU double positive granule neurons compared to both vehicle-treated animals and sham surgery animals. The higher number of IHC double positive cells observed in the ALPHA-1062 treated animals is indicative of increased neurogenesis in the dentate gyrus compared to vehicle treated animals (see also FIG. 15) suggesting that ALPHA-1062 treatment increased neuronal recovery and neurogenesis in brain tissue.

ALPHA 1062 Significantly Reduces Pathological p-Tau Accumulation in the Injured Cortex and Hippocampus.

IHC for total Tau and p-Tau (results shown in FIGS. 17 and 18) was carried out. Tissue from sham surgery, ALPHA-1062 treated or vehicle treated animals was labelled with antibodies against p-Tau or Tau. Immunoreactive areas including cortex (CT), dentate gyrus (DG), CA3 and CA1 regions of the ipsilateral hemisphere were imaged and quantified by Image J software (NIH). As shown in FIG. 17, sham treatments (left bars) show relatively low levels of p-Tau, whereas TBI animals treated with vehicle (control) (central bars) show high levels of p-Tau. TBI animals treated with ALPHA-1062 (right bars) show significantly reduced levels of p-Tau compared to vehicle controls. Furthermore, as shown in FIG. 18, ALPHA 1062 treatment does not alter total Tau protein. This data indicates that ALPHA-1062 treatment reduces the accumulation pathological p-TAU after moderate TBI induced by CCI.

CONCLUSIONS

As compared to the vehicle control, ALPHA-1062 treatment significantly improved motor and sensory functional recovery in treated rats after TBI, measured by foot-fault, adhesive removal and mNSS tests.

Also, NOR and MWM tests at 5 weeks after TBI showed significantly improved cognitive functional recovery in rats when ALPHA-1062 treatment was administered. ALPHA-1062 treatment did not significantly alter the body weight over the 35-day study, in comparison to untreated or vehicle treated animals. Accordingly, no evidence of overt toxicity in ALPHA-1062 treated rats could be observed.

Further ALPHA-1062 treatment significantly reduced the lesion size measured at 35 days after injury and significantly reduced the neuronal cell loss in the cortex and hippocampus of ipsilateral side. Surprisingly, the degree of neuroprotection afforded by ALPHA-1062 treatment preserved neurons in regions affected by the TBI to the extent that their numbers were indistinguishable from those determined for sham (non-TBI) control animals.

ALPHA-1062 treatment also significantly enhanced neurogenesis including augmentation of DCX+ neuroblasts and BrdU/NeuN+new neurons in the DG.

In conclusion, acute intranasal (IN) administration (e.g. 2 hours post injury) after TBI followed by regular administration of ALPHA-1062 (e.g. daily) provides neuroprotection and stimulates neurogenesis as well as significantly improves sensorimotor and cognitive functional recovery in a rat contusion model of TBI compared to the vehicle treatment.

ALPHA-1062 also significantly reduce pathological p-Tau accumulation, reducing the likelihood of further tissue damage driven by p-Tau.

These data suggest that ALPHA-1062 has potential as a treatment for acute TBI, for example via intranasal administration.

Example 2: Antimicrobial Properties of ALPHA-1062

In order to assess the anti-microbial properties of ALPHA-1062, the USP (US Pharmacopeia) Chapter 51 Preservative Challenge Test (USP 51) was employed. The USP 51 is a common method used to gauge preservative effectiveness. Much like a Preservative Challenge Screen, it is used to evaluate the effect of preservatives in cosmetics, personal care products, and drug products. Preservatives are typically antimicrobial ingredients that are added to aqueous product formulations to help maintain the safety of the product by inhibiting the growth and reducing the number of microbial contaminants.

In the context of the present invention, ALPHA-1062 (in the form of the gluconate salt) was assessed in place of (as) a preservative. No additional preservative was added to the ALPHA-1062 gluconate preparation, rather an anti-microbial effect of the agent itself (ALPHA-1062) was assessed. ALPHA-1062 is therefore the anti-microbial agent in the assay and experiments described below.

The USP 51 challenge test utilizes 5 microorganisms (3 bacteria and 2 fungi) for challenge testing. Each of the microorganisms are known strains of pathogenic microorganisms and they represent a wide range of microbial physiologies.

Cultures of the following microorganisms were applied, as per standard guidelines for USP 51: *Candida albicans* (ATCC No. 10231), *Aspergillus brasiliensis* (ATCC No. 16404), *Escherichia coli* (ATCC No. 8739), *Pseudomonas aeruginosa* (ATCC No. 9027), and *Staphylococcus aureus* (ATCC No. 6538).

The test was conducted in five sterile, capped bacteriological containers of suitable size into which a sufficient volume of product has been transferred. Each container was inoculated with one of the prepared and standardized inoculums and was mixed accordingly. The volume of the suspension inoculum used was between 0.5% and 1.0% of the volume of the product. The concentration of test microorganisms that was added to the product was such that the final concentration of the test preparation after inoculation was between $1\times10^5$ and $1\times10^6$ CFU per mL of the product, according to standard guidelines for Category 2 products.

The initial concentration of viable microorganisms in each test preparation was estimated based on the concentration of microorganisms in each of the standardized inoculums, as determined by the plate-count method.

The inoculated containers were incubated at 22.5±2.5° C. and each container was sampled at the appropriate intervals, as specified in Table 3. Any changes observed in the appearance of the culture was recorded at these intervals. By using the plate-count procedure, the number of CFU present in each test preparation was determined for the applicable intervals.

An inactivator (neutralizer) of the specific antimicrobial was incorporated in the plate count or in the appropriate dilution prepared for plating. These conditions were determined in the validation study for that sample based upon the conditions of media and microbial recovery incubation times listed in Table 2. Using the calculated concentrations of CFU per mL present at the start of the test, the change in log 10 values of the concentration of CFU per mL for each microorganism was calculated at the applicable test intervals, and the changes were expressed in terms of log reductions.

TABLE 4

Antimicrobial Effectiveness Report for ALPHA-1062 Gluconate:

| Organism | Initial CFU/mL | Initial $Log_{10}$ | Day 14 CFU/mL | Day 14 Log Reduction | Day 28 CFU/mL | Day 28 Log Reduction |
|---|---|---|---|---|---|---|
| *E. coli* ATCC 8739 | $9.1 \times 10^5$ | 6.0 | <10 | 5.0 | <10 | 5.0 |
| *P. aeruginosa* ATCC 9027 | $2.9 \times 10^5$ | 5.5 | <10 | 4.5 | <10 | 4.5 |
| *S. aureus* ATCC 6538 | $4.0 \times 10^5$ | 5.6 | <10 | 4.6 | <10 | 4.6 |
| *C. albicans* ATCC 10231 | $6.7 \times 10^5$ | 5.8 | <10 | 4.8 | <10 | 4.8 |
| *A. brasiliensis* ATCC 16404 | $2.2 \times 10^5$ | 5.3 | $1.6 \times 10^2$ | 3.1 | $1.5 \times 10^2$ | 3.1 |

As can be seen from the data provided, the gluconate salt of ALPHA-1062 exhibits a strong anti-microbial effect against all 5 organisms tested in the USP 51. The USP Criteria for Category 2 were employed in order to determine the presence of an anti-microbial effect. For bacteria, an antimicrobial effect is evident when at least a 2.0 log reduction from the initial count is evident at 14 days and no increase is evident from the 14-day count at 28 days. For yeast and molds, an antimicrobial effect is evident when no increase from the initial calculated count is determined at 14 and 28 days. With respect to the data above, the effect against bacteria and fungi therefore exceeded the requirements to demonstrate an anti-microbial effect for a Category 2 product.

The invention claimed is:

1. A method for treating a confirmed or suspected traumatic brain injury (TBI) in a subject, comprising administering compound ALPHA-1062 or salt thereof to said subject.

2. The method according to claim 1, wherein the compound ALPHA-1062 is in a composition in liquid form.

3. The method according to claim 2, wherein the composition is administered intranasally.

4. The method according to claim 2, wherein the composition is self-preserving and anti-microbial, wherein the composition is absent of additional antimicrobial preservatives.

5. The method according to claim 2, wherein the composition is present in a multi-use dispenser configured for intranasal administration.

6. The method according to claim 1, wherein the subject that has or is suspected to suffer from TBI shows one or more symptoms selected from the group consisting of dizziness, balance problems, headaches, nausea, vomiting, light sensitivity, impaired memory, sleep abnormalities, impaired concentration and impaired vision.

7. The method according to claim 1, wherein the subject that has or is suspected to suffer from moderate or severe TBI shows one or more symptoms selected from the group consisting of weakness in arms and legs, balance and coordination problems, severe or increasing headaches, impaired sensory perception, impaired cognitive skills, impaired memory, impaired communication and learning, personality changes, behavior abnormalities and impaired vision and hearing.

8. The method according to claim 1, wherein the subject that has or is suspected to suffer from severe TBI shows one or more symptoms selected from the group consisting of paralysis, coma, loss of consciousness, dilated pupils, loss of cerebrospinal fluid from the ears or nose, loss of bowel and/or bladder control, breathing problems, slow pulse, breathing problems, slow breathing rate with an increase in blood pressure and droopy eyelid or facial weakness.

9. The method according to claim 1, wherein the traumatic brain injury (TBI) leads to or is accompanied by one or more injuries selected from the group consisting of a hematoma, contusion, intracerebral hemorrhage, subarachnoid hemorrhage, diffuse injuries, diffuse axonal injury, ischemia, primary brain injury and secondary brain injury.

10. The method according to claim 1, wherein the traumatic brain injury (TBI) is caused by a closed head injury or penetrating head injury.

11. The method according to claim 1, wherein the traumatic brain injury (TBI) is caused by a head injury resulting from an incident selected from the group consisting of a fall, a motor vehicle-related incident, a strike or blow to the head from or against an object, an explosion (causing blast-related TBI), a sports-related incident, and interpersonal physical violence or violence by other means.

12. The method according to claim 1, wherein the subject that has or is suspected to suffer from TBI is an infant under the age of 4 years, a child from 4 to 12 years of age, or an adolescent from 12 to 17 years of age.

13. The method according to claim 1, wherein the subject that has or is suspected to suffer from TBI is an adult between 18 and 65 years of age, or an elderly adult of over 65 years of age.

14. The method according to claim 1, comprising stimulating and/or enhancing neurogenesis and/or neuronal recovery in the brain of a subject that is confirmed or suspected to have suffered traumatic brain injury (TBI).

15. The method according to claim 1, comprising preventing, inhibiting and/or reducing neuronal cell loss in the brain of a subject that is confirmed or suspected to have suffered traumatic brain injury (TBI).

16. The method according to claim 1, comprising reducing the size of one or more lesions and/or injuries in the brain of in a subject that is confirmed or suspected to have suffered traumatic brain injury (TBI).

17. The method according to claim 1, comprising preserving brain tissue and/or neuronal tissue in the brain of in a subject that is confirmed or suspected to have suffered traumatic brain injury (TBI).

18. The method according to claim 1, comprising reducing and/or preventing levels and/or formation of p-Tau in the brain of a subject that is confirmed or suspected to have suffered traumatic brain injury (TBI).

19. The method according to claim 1, wherein the traumatic brain injury (TBI) is associated with trauma to the nasal cavity and the method comprises treatment of traumatic brain injury (TBI) and concurrent treatment and/or prevention of microbial infection of the nasal cavity.

20. The method according to claim 1, wherein the traumatic brain injury (TBI) is associated with disruption of the blood brain barrier and the method comprises treatment of traumatic brain injury (TBI) and concurrent treatment and/or prevention of microbial infection of the central nervous system.

21. The method according to claim 2, wherein the compound ALPHA-1062 or salt thereof is present in the composition at a concentration of 1 to 500 mg/mL.

22. The method according to claim 2, wherein the compound ALPHA-1062 is present in the composition from a gluconate salt at a concentration of 50 to 100 mg/mL.

23. The method according to claim 1, wherein the compound ALPHA-1062 is administered at a dose of 0.1 to 200 mg, one to three times daily.

24. The method according to claim 1, wherein the compound ALPHA-1062 is administered within 24 hours of traumatic brain injury (TBI) in the subject.

25. The method according to claim 24, wherein the compound ALPHA-1062 is administered within 1 hour of traumatic brain injury (TBI) in the subject.

26. The method according to claim 2, wherein the composition is a solution comprising the compound ALPHA-1062 or salt thereof.

27. The method according to claim 2, wherein the composition is an emulsion or a suspension comprising the compound ALPHA-1062 or salt thereof.

* * * * *